United States Patent
Chang et al.

(10) Patent No.: US 9,423,396 B2
(45) Date of Patent: Aug. 23, 2016

(54) BODIPY STRUCTURE FLUORESCENCE PROBES FOR DIVERSE BIOLOGICAL APPLICATIONS

(71) Applicants: National University of Singapore, Singapore (SG); Agency for Science, Technology and Research, Singapore (SG)

(72) Inventors: Young-Tae Chang, Singapore (SG); Sung Chan Lee, Singapore (SG); Nam-Young Kang, Singapore (SG); Seong Wook Yun, Singapore (SG); Cheryl Kit Mun Leong, Singapore (SG); Hyung Ho Ha, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 126 days.

(21) Appl. No.: 14/367,596

(22) PCT Filed: Dec. 20, 2012

(86) PCT No.: PCT/SG2012/000483
§ 371 (c)(1),
(2) Date: Jun. 20, 2014

(87) PCT Pub. No.: WO2013/095305
PCT Pub. Date: Jun. 27, 2013

(65) Prior Publication Data
US 2014/0359794 A1 Dec. 4, 2014

Related U.S. Application Data

(60) Provisional application No. 61/579,461, filed on Dec. 22, 2011.

(51) Int. Cl.
| | |
|---|---|
| *G01N 33/53* | (2006.01) |
| *C07F 5/02* | (2006.01) |
| *G01N 33/569* | (2006.01) |
| *G01N 33/58* | (2006.01) |
| *A61K 49/00* | (2006.01) |

(52) U.S. Cl.
CPC ......... *G01N 33/5306* (2013.01); *A61K 49/006* (2013.01); *A61K 49/0021* (2013.01); *C07F 5/02* (2013.01); *C07F 5/022* (2013.01); *G01N 33/56966* (2013.01); *G01N 33/582* (2013.01); *G01N 2458/00* (2013.01)

(58) Field of Classification Search
CPC ........ G01N 33/53; C07F 5/022; A61K 49/00
See application file for complete search history.

(56) References Cited

U.S. PATENT DOCUMENTS

| | | |
|---|---|---|
| 9,267,949 B2 | 2/2016 | Chang et al. |
| 2010/0291547 A1 | 11/2010 | Chen et al. |
| 2011/0054187 A1 | 3/2011 | Rurack et al. |
| 2014/0121129 A1 | 5/2014 | Chang et al. |

FOREIGN PATENT DOCUMENTS

| | | |
|---|---|---|
| CN | 101020787 | 8/2007 |
| CN | 101565554 | 10/2009 |
| JP | 2002025635 A | 1/2002 |
| JP | 2008239615 A | 10/2008 |
| WO | WO 2012/173575 A1 | 12/2012 |

OTHER PUBLICATIONS

Gregor Jung et al. Solvent-dependent steady-state fluorescence spectroscopy for searching ESPT-dyes: solvatochromism of HPTS revisited, Phys. Chem. Chem. Phys, 2009, 11, 1416-1426.*

(Continued)

*Primary Examiner* — Michael G Hartley
*Assistant Examiner* — Jagadishwar Samala
(74) *Attorney, Agent, or Firm* — Hamilton, Brook, Smith & Reynolds, P.C.

(57) ABSTRACT

The present invention is directed to a fluorescence compound represented by structural Formula (I), with specificity to neural stem cells: (I), or a pharmaceutically acceptable salt thereof. The variables for structural Formula (I) are defined herein. Also described are methods for detection of beta cells, pancreatic islets and microglia cells, comprising using a compound of structural Formula (I) or pharmaceutically acceptable salts thereof. Compounds of structural Formula (I) can also differentiate healthy pancreatic islet cells from diabetic pancreatic islet cells.

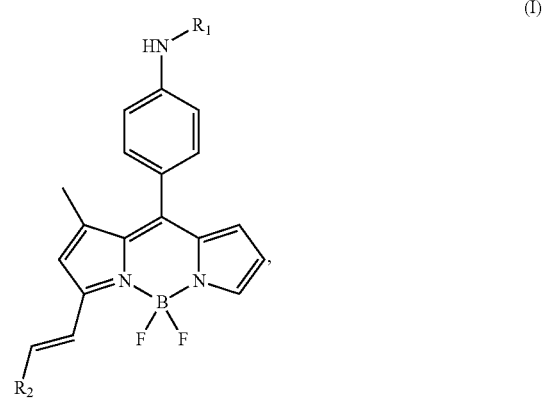

20 Claims, 11 Drawing Sheets

(56) References Cited

OTHER PUBLICATIONS

Marc Vendrell et al. Solid-phase synthesis of BODIPY dyes and development of an immunoglobulin fluorescent sensor, Chem. Commun. 2011, 47, 8424-8426.*

Bozdemir O.A., et al., "Selective manipulation of ICT and PET processes in styryl-Bodipy derivatives: applications in molecular logic and fluorescence sensing of metal ions"., *Journal of American Chemical Society*, 132(23): 8029-8036 (2010).

Cui, A., et al., "Synthesis, spectral properties and photostability of novel boron-dipyrromethene dyes", *Journal of Photochemistry and Photobiology A: Chemistry*, 186(1): 85-92 (2007).

Das, R.K., et al., "Target Identification: A Challenging Step in Forward Chemical Genetics", IBC, 3(3):1-16 (2011).

Descalzo, A.B., et al., "Red/near-infrred boron-dipyrromethene dyes as strongly emitting fluorophores", *Annals of the New York Academy of Sciences*, pp. 164-171 (2008).

Dumont, Y., et al., "Bodipy-conjugated neuropeptide Y ligands: new fluorescent tools to tag Y1, Y2, Y4 and Y5 receptor sybtypes", *British Journal of Pharmacology*, 146(8): 1069-1081 (2005).

Hoogendoorn et al., "Synthesis of pH-Activatable Red Fluorescent BODIPY Dyes With Distinct Functionalities," Organic Letters, 13(20): 5656-5659 (Sep. 26, 2011), See Abstract, Compounds of Schemes 1 and Figure 2.

International Preliminary Report on Patentability for Int'l Application No. PCT/SG2012/00483, entitled: "Bodipy Structure Fluorescence Probes for Diverse Biological Applications," Date of Mailing: Jul. 3, 2014.

International Search Report for Int'l Application No. PCT/SG2012/000483, entitled: "Bodipy Structure Fluorescence Probes for Diverse Biological Applications," Date of Mailing: Feb. 8, 2013.

Johnson, I.D., et al., "Fluorescent membrane probes incorporating dipyrrometheneboron difluoride fluorophores", 198(2): 228-237 (1991).

Kang, N.Y., et al., "Diversity-driven chemical probe development for biomolecules: beyond hypothesis-driven approach", *Chem So. Rev.*, 40: 3613-3626 (2011).

Karolin, J., et al., "Fluorescence and Absorption Spectroscopic Properties of Dipyrrometheneboron Difluoride (BODIPY) Derivatives in Liquids, Lipid Membranes, and Proteins", *J. Am. Chem. Soc.* 1994, 116: 7801-7806.

Kim, Y.K., et al., "Control of Muscle Differentiation by a Mitochondria-Targeted Fluorophore" *J. Am. Chem. Soc.*, 132: 576-579 (2010).

Lee et al., "Bodipy-diaerylate Imaging Probes for Targeted Proteins Inside Live Cells," Chem. Commun., 47: 4508-4510 (Mar. 8, 2011), See Abstract, Scheme 1.

Lee et al., "Synthesis of BODIPY Library and Its Application to the Development of Live Cell Glucagon Imaging Probe," J. Am. Chem. Soc., 131(29): 10077-10082 (2009), See Abstract, Scheme 1.

Lee, H.Y., "BODIPY-functionalized gold nanoparticles as a selective fluoro-chromogenic chemosensor for imaging Cu2+ in living cells", *Analyst*, 135(8): 2022-2027 (2010).

Li, Q., et al., "Styryl-based compounds as potential in vivo imaging agents for beta-amyloid plaques", Chembiochem, 8(14): 1679-87 (Sep. 24, 2007).

Loudet et al., "Bodipy Dyes and Their Derivatives: Synthesis and Spectroscopic Properties," Chem. Rev., 107: 4891-4932 (2007), See whole document.

Lukowiak, B., et al., "Identification and Purification of Functional Human β-cells by a New Specific Zinc-Fluorescent Probe", *J. Histochem. Cytochem.*, 49: 519-528 (2001).

Mula, S., et al., "Dual Bodipy Fluorophores Linked by Polyethyleneglycol Spacers", Tetrahedron Letters, 50(46): 6383-6388 (2009), See Abstract, Compounds 1-18.

Ono, M., "Development of dual functional SPEC/fluorescent probes for imaging cerebral beta-amyloid plaques", *Bioorganic & Medicinal Chemistry Letters* 20(13): 3885-3888 (2010).

Polazzi, E., "Microglia and Neuroprotection: from in vivo studies to therapeutic applications", Prog. Neurobiol., 92(3): 293-315 (Nov. 2010) (Epub. Jul. 4, 2010).

Qin, W., et al., "Synthesis, spectroscopy, crystal structure, electrochemistry, and quantum chemical and molecular dynamics calculations of a 3-anilino difluoroboron dipyrromethene dye", *Journal of Physical Chemistry A.*, 113(2): 439-447 (2009).

Takahashi, N., et al., "Two-photon excitation imaging of pancreatic islets with various fluorescent probes", Diabetes, Suppl 1, S25-S28 (2002).

Ulrich et al., "The Chemistry of Fluorescent BODIPY Dyes: Versatility Unsurpassed," Angew. Chem. Tm. Ed., 47: 1184-1201 (2008), See whole document.

Vendrell, M., et al., "Diversity-oriented fluorescence library approaches for probe discovery and development", *Current Opinion in Chemical Biology*, 14(3): 383-389 (2010).

Wang, Yan-Wei, et al., "A colorimetric and fluorescent turn-on chemosensor for $Al^{3+}$ and its applicant in bioimaging", *Tetrahedron Letters*, 50(45): 6169-6172 (2009).

Written Opinion for International Application No. PCT/SG2012/000483, entitled: "Bodipy Structure Fluorescence Probes for Diverse Biological Applications," Date of Mailing: Feb. 8, 2013.

Wüstner, D., et al., "Quantitative assessment of sterol traffic in living cells by dual labeling with dehydroergosterol and BODIPY-cholesterol", *Chemistry and Physics Lipids*, 164(3) 221-235 (2011).

Yu, Y.H., et al., "Mono- and di(dimethylamino)styryl-substituted borondipyrromethene and borondi indomethene dyes with intense near-infrared fluorescence", *Chemistry, an Asian Journal*, 1(1-2): 176-197 (2006).

Aijun, C., "Synthesis, spectral properties and photostability of novel boron-dipyrromethene dyes", *Journal of Photochemistry and Photobiology A: Chemistry*, 186(1): 85-92 (2007).

Coskun, A. et al., "Ion Sensing Coupled to Resonance Energy Transfer: A Highly Selective and Sensitive Ratiometric Fluorescent Chemosensor for Ag(I) by a Modular Approach", *J. Am. Chem. Soc.*, 127, p. 10464-10465 (2005).

Gomez-Duran, C.F., et al.,"8-PropargylaminoBODIPY: unprecedented blue-emitting pyrromethene dye. Synthesis, photophysics and laser properties", *Chem. Commun.*, 46: 5103-5105 (2010).

Han., J., et al., 3- and 5-Functionalized BODIPYs via Liebeskind-Srogl reaction, *Org. Biomol. Chem*, 7: 34-36 (2009).

Jung, G. et al., "Solvent-dependent steady-state fluorescence spectroscopy for searching ESPT-dyes: solvatochromism of HPTS revisited", *Physical Chemistry Chemical Physics*, 11(9): 1416-1426 (2009).

Kang, N.Y., et al., "Visualization and Isolation of Langerhans Islets by a Fluorescent Probe PiY", *Angew Chem Int Ed.*, ., 52:1-5 (2013).

Kollmannsberger M., et al., "Ultrafast Charge Transfer in Amino-Substituted Boron Dipyrromethene Dyes and Its Inhibition by Cation Complexation: A New Design Concept for Highly Sensitive Fluorescent Probes", *J. Phys. Chem. A.*, 102: 10211-10220 (1998).

Lager, E., et al., "Novel meso-Polyarylamine-BODIPY Hybrids: Synthesis and Study of Their Optical Properties", *J. Org. Chem.*, 74: 2053-2058 (2009).

Lavis, L. D., et al., "Bright Ideas for Chemical Biology", *ACS Chem. Biol.*, 3(3): 142-155 (2008).

Lee, J. S., et al., "Accelerating fluorescent sensor discovery: unbiased screening of a diversity-oriented BODIPY library", *Chem Commun.*, 47: 2339-2341 (2011).

Leen, V., et al., "Direct functionalization of BODIPY dyes by oxidative nucleophilic hydrogen substitution at the 3- or 3,5-positions", *Chem. Commun.*, 46: 4908-4910 (2010).

Leen, V., et al., "A versatile, modular synthesis of monofunctionalized BODIPY dyes", *W. Chem. Commun.*, 45: 4515-4517 (2009).

Leong, C., et al., "Microglia Specific Fluorescent Probes for Live Cell Imaging", *Chem Commun*, 50:1089-1091 (2014).

Li Z., et al., "First Synthesis of Free Cholesterol-BODIPY Conjugates", *J. Org. Chem.*, 71:1718-1721 (2006).

Nicolaou, K. C., et al., "A Mild Method for the Synthesis of 2-Ketopyrroles from Carboxylic Acids", *Tetrahedron Lett.*, 22: 4647-4650 (1981).

Peng X., et al., "A Selective Fluorescent Sensor for Imaging $Cd^{2+}$ in Living Cells", *J. Am. Chem. Soc.*, 129, 1500-1501 (2007).

(56) References Cited

OTHER PUBLICATIONS

Qin, W., et al., "Solvent-dependent photophysical properties of borondipyrromethene dyes in solution", *Chem. Phys. Lett.*, 420: 562-568 (2006).

Ramachary, D. B., et al., "Towards Organo-Click Chemistry: Development of Organocatalytic Multicomponent Reactions Through Combinations of Aldol, Wittig, Knoevenagel, Michael, Diels-Alder and Huisgen Cycloaddition Reactions", *Chemistry*, 10: 5323-5331 (2004).

Rich, R. L., et al., "Survey of the year 2007 commercial optical biosensor literature", *J. Mol. Recognit.*, 21: 355-400 (2008).

Rohand, T. et al., "Functionalisation of Fluorescent BODIPY dyes by nucleophilic substitution", *Chem. Commun.* 42: 266-268 (2006).

Rohand, T. et al., "Palladium-Catalyzed Coupling Reactions for the Functionalization of BODIPY Dyes with Fluorescence Spanning the Visible Spectrum", *J. Org. Chem*, p. 4658-4663 (2006).

Rurack, K., et al., "Molecular-Switching in the Near Infrared (NIR) with a Functionalized Boron-Dipyrromethene Dye", *Angew. Chem. Int. Ed.*, 40(2): 385-387 (2001).

Sunahara, H., et al., "Design and Synthesis of a Library of BODIPY-Based Environmental Polarity Sensors Utilizing Photoinduced Electron-Transfer-Controlled Fluorescence ON/OFF Switching", *J. Am. Chem. Soc.*, 129: 5597-5604 (2007).

Supplemental European Search Report for EP 12 85 9000, "Bodipy Structure Fluorescence Probes for Diverse Biological Applications," date of mailing Jul. 31, 2015.

Thivierge, C., et al., "Spectral Dispersion and Water Solubilization of BODIPY Dyes via Palladium-Catalyzed C-H Functionalization", *American Chemical Society*, 9(11): 2135-2138 (2007).

Vendrell, M. et al., "Solid-phase synthesis of BODIPY dyes and development of an immunoglobulin Fluorescent sensor", *Chemical Communications*, 47(29): 8424-8426 (2011).

Yogo, T. et al., "Highly Efficient and Photostable Photosensitizer Based on BODIPY Chromophore", *J. Am. Chem. Soc.*, 127, p. 12162-12163 (2005).

* cited by examiner

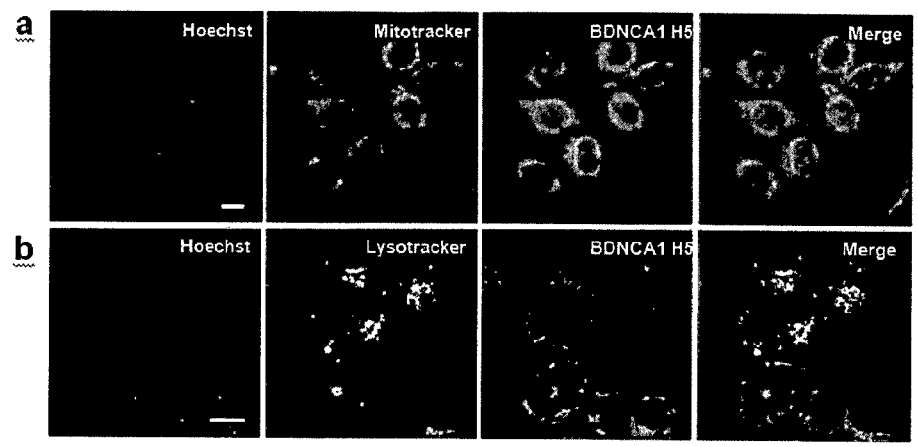
FIG. 10a
FIG. 10b
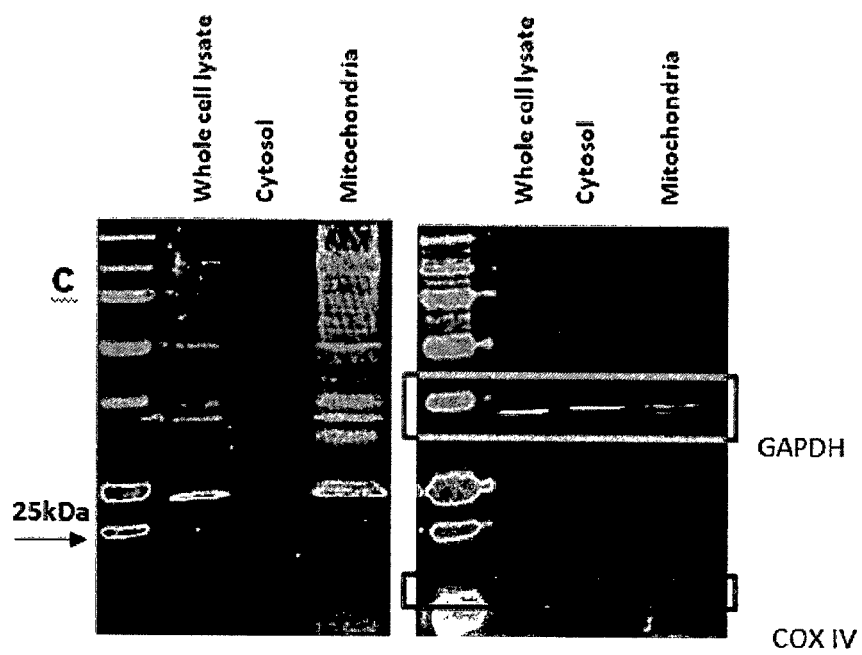
FIG. 10c

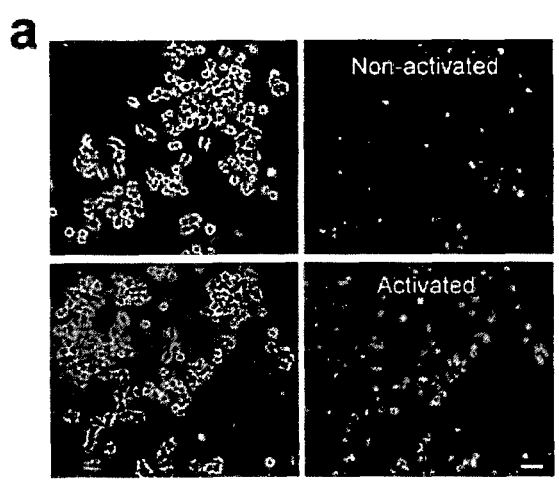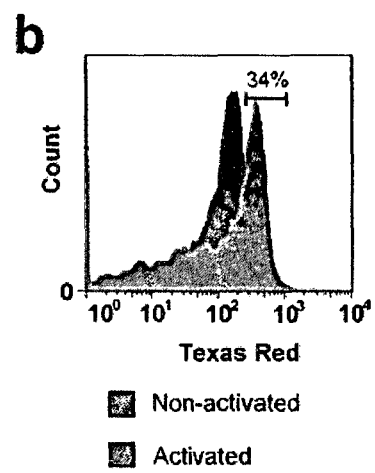
FIG. 11a
FIG. 11b

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: mGAPDH-F1

<400> SEQUENCE: 1
aagggctcat gaccacagtc                                                  20

<210> SEQ ID NO 2
<211> LENGTH: 20
<212> TYPE: DNA
<213> ORGANISM: Artificial Sequence
<220> FEATURE:
<223> OTHER INFORMATION: mGAPDH-R1

<400> SEQUENCE: 2
ggatgcaggg atgatgttct                                                  20

<210> SEQ ID NO 3
<211> LENGTH: 20
<212> TYPE: DNA
<213> ORGANISM: Artificial Sequence
<220> FEATURE:
<223> OTHER INFORMATION: mTNFalpha-F1

<400> SEQUENCE: 3
tagccaggag ggagaacaga                                                  20

<210> SEQ ID NO 4
<211> LENGTH: 20
<212> TYPE: DNA
<213> ORGANISM: Artificial Sequence
<220> FEATURE:
<223> OTHER INFORMATION: mTNFalpha-R1

<400> SEQUENCE: 4
ttttctggag ggagatgtgg                                                  20

<210> SEQ ID NO 5
<211> LENGTH: 20
<212> TYPE: DNA
<213> ORGANISM: Artificial Sequence
<220> FEATURE:
<223> OTHER INFORMATION: MIL-6-F1

<400> SEQUENCE: 5
ccggagagga gacttcacag                                                  20

<210> SEQ ID NO 6
<211> LENGTH: 20
<212> TYPE: DNA
<213> ORGANISM: Artificial Sequence
<220> FEATURE:
<223> OTHER INFORMATION: MIL-6-R1

<400> SEQUENCE: 6
tccacgattt cccagagaac                                                  20
```

BODIPY STRUCTURE FLUORESCENCE PROBES FOR DIVERSE BIOLOGICAL APPLICATIONS

RELATED APPLICATION(S)

This application is the U.S. National Stage of International Application No. PCT/SG2012/000483, filed on Dec. 20, 2012, which designates the U.S., published in English, and claims the benefit of U.S. Provisional Application No. 61/579,461, filed on Dec. 22, 2011. The entire teachings of the above application(s) are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 44591040002_FINALSEQUENCELISTING.txt; created Jun. 18, 2014, 2 KB in size.

BACKGROUND OF THE INVENTION

Fluorescent probe molecules have been widely used in bioimaging and medicinal applications for several decades due to their high sensitivity and easy visibility. During the past few decades, a number of small molecule fluorescent chemosensors have been developed for use in biological analyses, which typically are elaborately designed to selectively detect a target substance or phenomenon.

Most fluorescent chemosensors employ increase or decrease in their emission intensity as a sensing signal in response to the surrounding medium or through specific molecular recognition events. Due to their simplicity and high sensitivity, fluorescent sensors have been widely utilized as popular tools in chemical, biological, and medical applications.

The conventional bioprobe design is based upon a hypothesis-driven approach. The conventional bioprobe usually consists of three parts: a target recognition motif, a linker and a fluorophore. The target recognition motif is designed based on the identity and structure of the target, and then is paired with any number of fluorophores to generate a bioprobe that will efficiently and selectively allow visualization or staining of a target. The basic assumption of this hypothesis-driven approach is that the scientist knows the target in advance, and then designs the recognition motif tailored specifically for the target. Therefore, the scope of bioprobe development is intrinsically limited by the available knowledge for the target. An alternative to this process is combinatorial dye library synthesis, which enables a scientist to arrive at a library of diversity directed sensors.

There remains a need to develop a library of fluorescent sensors that may be used in crucial biomedical applications, such as the selective imaging of pancreatic islets or microglia cells.

SUMMARY OF THE INVENTION

The present invention is directed to novel BODIPY compounds represented by structural Formula (I) or pharmaceutically acceptable salts thereof:

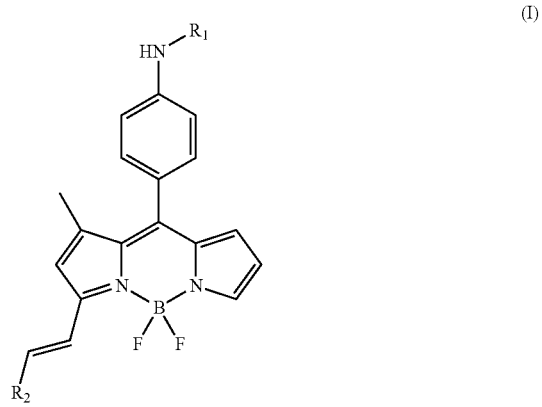

wherein:

$R_1$ is hydrogen or —$COR_3$;

$R_2$ is ($C_6$-$C_{16}$)aryl, ($C_3$-$C_{10}$)heteroaryl, ($C_1$-$C_6$)alkyl, ($C_1$-$C_6$)cycloalkyl, ($C_2$-$C_6$)alkenyl, or C≡CH;

$R_2$ is optionally substituted with 1-5 substituents independently selected from ($C_1$-$C_6$)alkyl, halogen, amino, cyano, —COOH, halo($C_1$-$C_6$)alkyl, hydroxy($C_0$-$C_6$)alkyl, ($C_6$-$C_{10}$)aryl, ($C_3$-$C_{10}$)heteroaryl, halo($C_6$-$C_{10}$)aryl, hydroxy($C_6$-$C_{10}$)aryl, ($C_1$-$C_6$)alkoxy, halo($C_1$-$C_6$)alkoxy, ($C_6$-$C_{16}$)aryloxy, ($C_3$-$C_8$)cycloalkyl, halo($C_6$-$C_{10}$)aryl($C_1$-$C_6$)alkoxy, ($C_1$-$C_6$)alkoxy($C_6$-$C_{10}$)aryl($C_1$-$C_6$)alkoxy, nitro, ($C_0$-$C_6$)alkyl($C_6$-$C_{10}$)aryl($C_0$-$C_6$)alkoxy, ($C_5$-$C_{10}$)heterocycle, —$OCHF_2$, —$OCF_3$, —$SCF_3$, —OBn, cyano($C_1$-$C_6$)alkylene, ($C_1$-$C_6$)alkoxyamino, ($C_6$-$C_{10}$)aryl($C_2$-$C_6$)alkenyl, ($C_2$-$C_6$)alkenyl($C_1$-$C_6$)alkoxy, ($C_2$-$C_6$)alkenyl, ($C_2$-$C_6$)alkenyl($C_6$-$C_{10}$)aryl, —N(($C_0$-$C_6$)alkyl)(($C_1$-$C_6$)alkyl), —N(($C_1$-$C_6$)alkyleneOH)(($C_1$-$C_6$)alkyleneOH), —N(($C_0$-$C_6$)alkyl)(($C_1$-$C_6$)alkyleneOH), —N(($C_1$-$C_6$)alkyleneOCO($C_1$-$C_6$)alkyl)(($C_1$-$C_6$)alkyleneOCO($C_1$-$C_6$)alkyl), —NCO($C_1$-$C_6$)alkyl, —$NPh_2$, —OPh(halogen)$_{0-3}$, —OPhO($C_1$-$C_6$)alkyl, —OPhO($C_1$-$C_6$)alkyl, —OCO($C_1$-$C_6$)alkyl, —OCO($C_1$-$C_6$)alkoxy, —O($C_1$-$C_6$)alkyl($C_6$-$C_{10}$)aryl, —O($C_2$-$C_6$)alkenyl, —O($C_2$-$C_6$)alkyleneN($CH_3$)$_2$, ($C_0$-$C_6$)alkylCOO($C_1$-$C_6$)alkyl, —$B(OH)_2$ or —S($C_1$-$C_6$)alkyl; and wherein any of the substituents selected from ($C_1$-$C_6$)alkyl, ($C_1$-$C_6$)alkoxy, ($C_6$-$C_{10}$)aryl, ($C_6$-$C_{16}$)aryloxy or ($C_5$-$C_{10}$)heteroaryl is further optionally substituted with 1-4 substituents selected from halogen, ($C_1$-$C_6$)alkyl, halo($C_1$-$C_6$)alkyl, amino, nitro, cyano, hydroxy($C_0$-$C_6$)alkyl, ($C_1$-$C_6$)alkoxy, —COO($C_0$-$C_6$)alkyl, or —CHO; and $R_3$ is ($C_1$-$C_{15}$)alkyl, ($C_2$-$C_{15}$)alkenyl, ($C_2$-$C_{15}$)alkynyl, ($C_6$-$C_{10}$)aryl or ($C_5$-$C_{10}$)heteroaryl, wherein $R_3$ is optionally substituted with 1-4 substituents independently selected from halogen, amino, cyano or hydroxyl.

In one embodiment of the invention, $R_2$ is $(C_6\text{-}C_{10})$aryl, and in another embodiment, $R_2$ is phenyl, optionally substituted with 1-4 substituents selected from —C(CH$_3$)$_3$ and —O—(C$_1$-C$_3$)alkyl. In a preferred embodiment of the invention, the compound has the structure of formula (II):

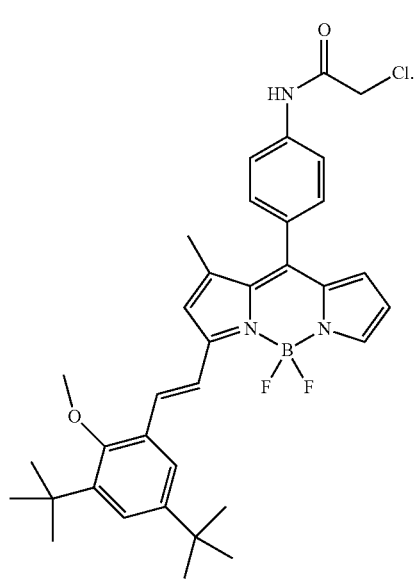

(II)

In another preferred embodiment of the invention, the compound has the structure of formula (III):

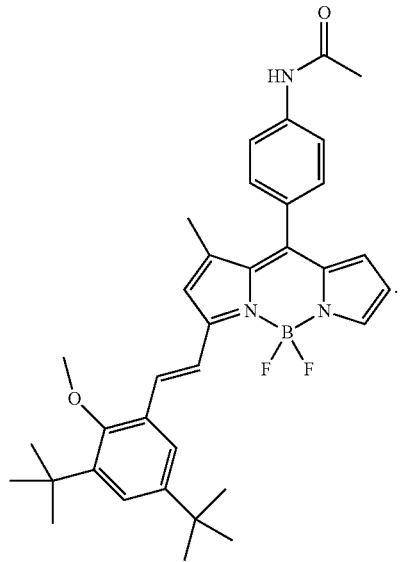

(III)

In another preferred embodiment of the invention, the compound has the structure of formula (IV):

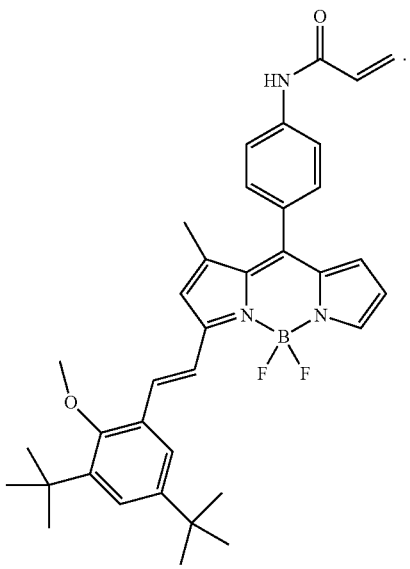

(IV)

In another preferred embodiment of the invention, the compound has the structure of formula (V):

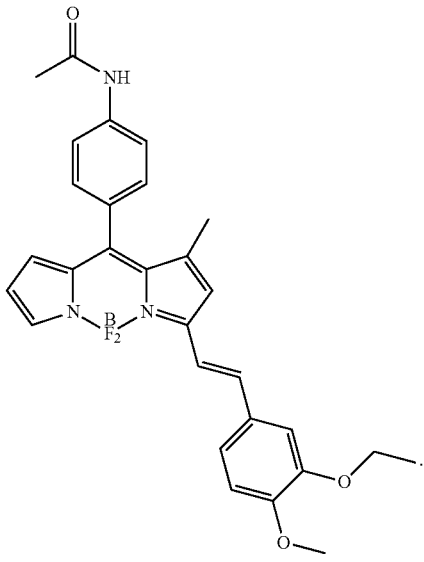

(V)

In another preferred embodiment of the invention, the compound has the structure of formula (VI):

(VI)

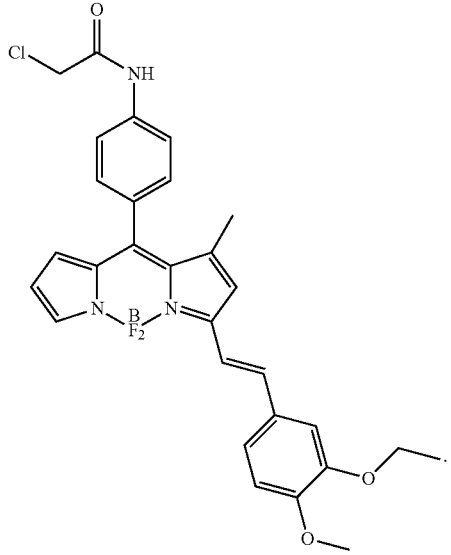

The invention is further directed to pharmaceutical compositions comprising a compound of any of formulae (I) through (VI) and one or more pharmaceutically acceptable carriers and/or one or more pharmaceutically acceptable diluents.

The present invention further provides methods for the solid phase synthesis of compounds of structural formulae (I) through (VI), comprising:

(a) reacting a compound of structural Formula (VII):

(VII)

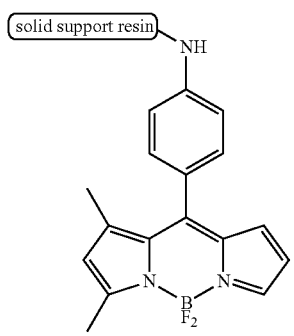

with a base and an aldehyde, such that the activated $C_3$-methyl group of Formula (VII) is modified in a solid-phase Knoevenagel-type, reaction to produce a compound of Formula VIII:

(VIII)

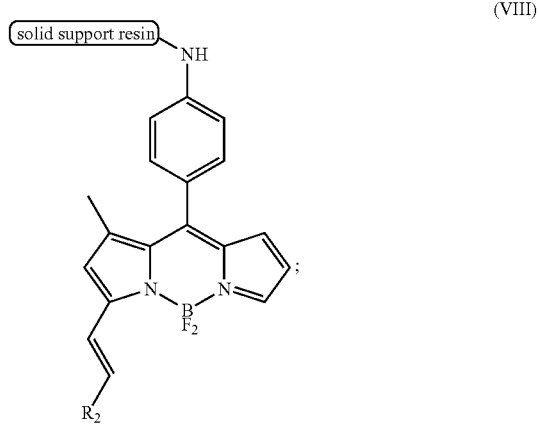

b) removing the solid support resin from the compound of structural Formula (VIII) produced in step (a) to generate a BODIPY structure of Formula (IX):

(IX)

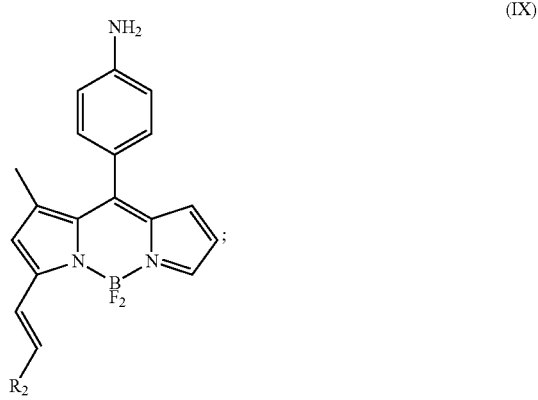

and c) optionally reacting the compound of structural Formula (IX) with an acid chloride of the formula $R_1(CO)Cl$ to generate a compound having the structure of one of formulae (I) through (VI).

The present invention further describes methods for detecting beta cells using image based screening. The methods comprise (a) contacting a sample comprising cells with a compound of structural Formula (I) or pharmaceutically acceptable salts thereof; (b) incubating the sample and the compound of step (a) together for a period of time sufficient to stain the cells; and (c) analyzing the incubated stained cells by spectroscopy to detect a fluorescence signal, wherein the presence of a fluorescence signal is indicative of the presence of the beta cells. In a preferred embodiment of the invention, the method utilizes a compound of formula (II) in the detection of beta cells. In another preferred embodiment of the invention, the method utilizes a compound of formula (III) in the detection of beta cells.

The present invention further describes methods for detecting microglia cells comprising (a) contacting a sample comprising cells with a compound of structural Formula (I) or a pharmaceutically acceptable salt thereof; (b) incubating the sample and compound of step a) together for a period of time sufficient to stain the cells; and (c) analyzing the incubated stained cells by spectroscopy to detect a fluorescence signal, wherein the presence of a fluorescence signal is indicative of the presence of microglia cells. In a preferred embodiment of the invention, the method utilizes a compound of formula (VI) in the detection of microglia cells. The invention further provides for methods of detecting microglia cells, in which activated microglia cells are distinguished from resting microglia cells by intensity of their fluorescence signals.

The present invention is further directed to methods for fluorescence imaging of pancreatic islet cells to determine health status, comprising (a) contacting the pancreatic islet cells with a compound of structural Formula (I) or pharmaceutically acceptable salts thereof; (b) incubating the cells and compound of step (a) together for a period of time sufficient for to stain the cells; (c) analyzing the incubated stained pancreatic islet cells by spectroscopy to detect a fluorescence signal; and (d) comparing the signal from step (c) to a fluorescence signal from reference sample of healthy pancreatic islet cells, to determine health status of the pancreatic islet cells. In a preferred embodiment of the invention, a compound having the structure of formula (III) is utilized in the fluorescence imaging of pancreatic islet cells.

The present invention provides that the fluorescence signal that is analyzed in the detection of beta cells, microglia cells, or pancreatic islet cell imaging is measured by fluorometer, UV/VIS spectrometer, Gemini XS fluorescence plate reader, a flow cytometry or a confocal microscope. Further, each of these methods are applied in vitro or alternately, in vivo.

The novel BODIPY dyes described herein are chemical compounds with fluorescence emission properties that enable staining of specific cell types and organs. Candidate compounds have high potential for the development of an in vivo islet imaging probe for pancreatic transplanted patient and microglia related inflammation imaging probe.

BRIEF DESCRIPTION OF THE DRAWINGS

The foregoing will be apparent from the following more particular description of example embodiments of the invention, as illustrated in the accompanying drawings.

FIG. 1a shows the chemical structure of BDNCA325. FIG. 1b shows the selective detection of a Beta TC-6 cell by BDNCA325 in contrast to Hoechst 33342 for nuclei staining. Specifically, the upper panel shows fluorescent (FL) images for Texas Red filter and the lower panel shows fluorescent (FL) images for DAPI filter. FIG. 1c shows the visualization of a pancreas section by BDNCA325 in vitro tissue staining. The same images for BDNCA325 were acquired before immunostaining with insulin and merged for identification of islets. Scale bar, 100 μm.

FIG. 2a shows islets of pancreas cryo-tissues after administration of PiY observed under low magnification fluorescent microscopy. Scale bar, 200 μm. The fluorescent image was taken by TRITC filter and the areas of islets were marked by red dots in bright field (B.F) and fluorescence panel. FIG. 2b shows the chemical structure of PiY. FIG. 2c shows PiY-stained tissues that were immunostained using insulin and then co-localized for confirmation. Scale bar, 100 um.

FIG. 3a shows comparative fluorescent images to exhibit differences between undamaged and damaged islets with PiY. These were used for analysis and the intensity size was examined using ROI software program. Scale bar, 100 μm. FIG. 3b shows that islets obtained from STZ mice have few cells. This is demonstrated by decreasing fluorescent intensity of PiY and confirmed with insulin antibody. Each fluorescent image was merged for identification of islets. FIG. 3d shows the diabetic animal model for type 1, generated by STZ administration.

FIG. 7A shows that BDNCA1 H5 has minimal cytotoxicity when used at concentrations of 1 uM and above. FIG. 7B is a measure of cell proliferation in the presence of compound staining. BDNCA1 H5 does not appear to affect cell proliferation as reflected by the robust increase in cell numbers over 48 hours.

FIG. 10a-10c show BV2 microglia that were co-stained with Mitotracker and BDNCA1H5 (FIG. 10a) or Lysotracker and BDNCA1 H5 (FIG. 10b). The compound shows good co-localization with Mitotracker. FIG. 10c shows an SDS-PAGE gel run with BV2 cell lysate extracts with the target band appearing as a strong fluorescence signal at the 25 kDa marker size (left). GAPDH was used as a loading control and COX IV was used as mitochondrial loading control to show that the signal is coming predominantly from the mitochondrial fraction.

FIGS. 11a and 11b show BV2 microglia activated with LPS showing brighter BDNCA1 H5 staining intensity as compared to their non-activated counterparts.

DETAILED DESCRIPTION OF THE INVENTION

Figure 1:
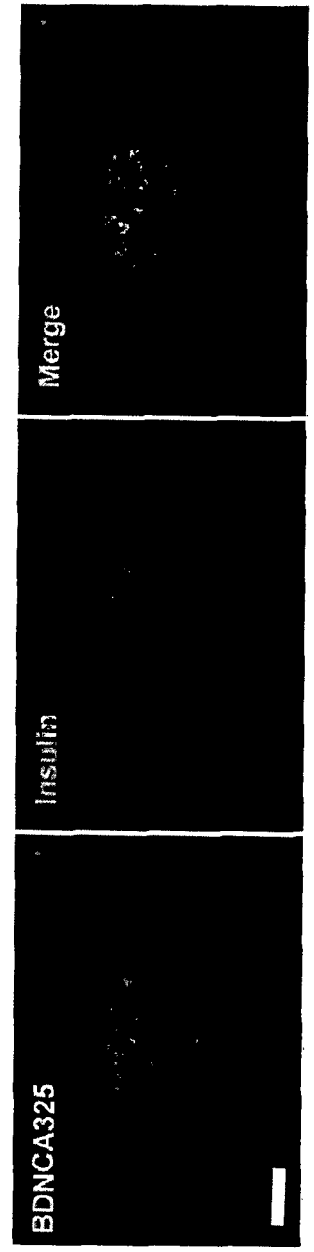
FIGS. 1a-1c show images of cellular detection utilizing the beta cell probe BDNCA325.
Figure 1:
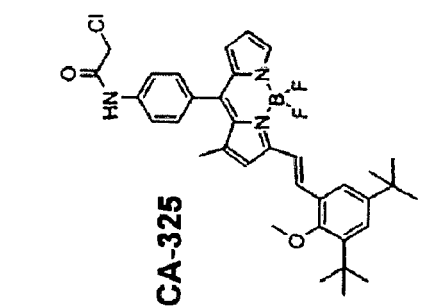

A description of example embodiments of the invention follows.

A novel class of dyes having a core structure of 4,4-difluoro-4-bora-3a,4a-diaza-s-indacene (BODIPY) is described herein. BODIPY fluorescent dyes are known in the art for outstanding photophysical properties as a fluorescent scaffold, such as high photostability, high fluorescent quantum yield, high extinction coefficient, and narrow emission bandwidth (Karolin, J.; Johansson, L.; Strandberg, L.; Ny, T. *J. Am. Chem. Soc.* 1994, 116, 7801-7806). The synthesis of a BODIPY-based library on solid support, and the subsequent discovery of pancreatic islet in vivo sensor and microglia sensor is disclosed.

Synthesis of BODIPY Fluorescent Sensors.

Scheme I, shown below, depicts a general synthetic scheme for the compounds of the invention.

One embodiment of the invention are compounds represented by structural Formula (I) or pharmaceutically acceptable salts thereof:

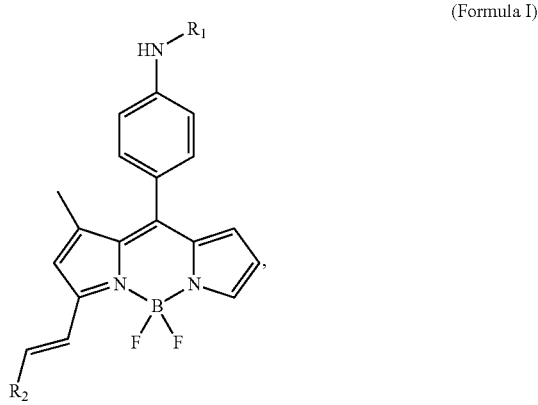

(Formula I)

Scheme 1.

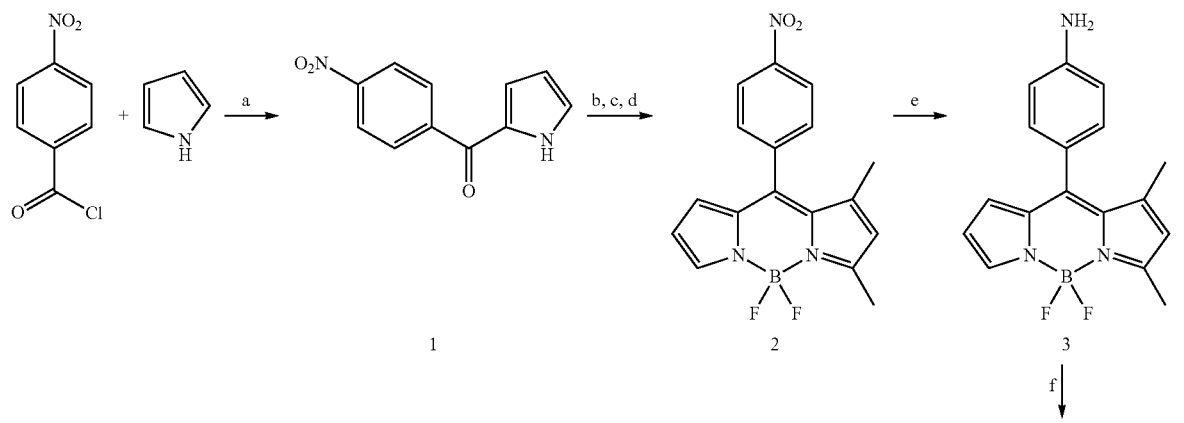

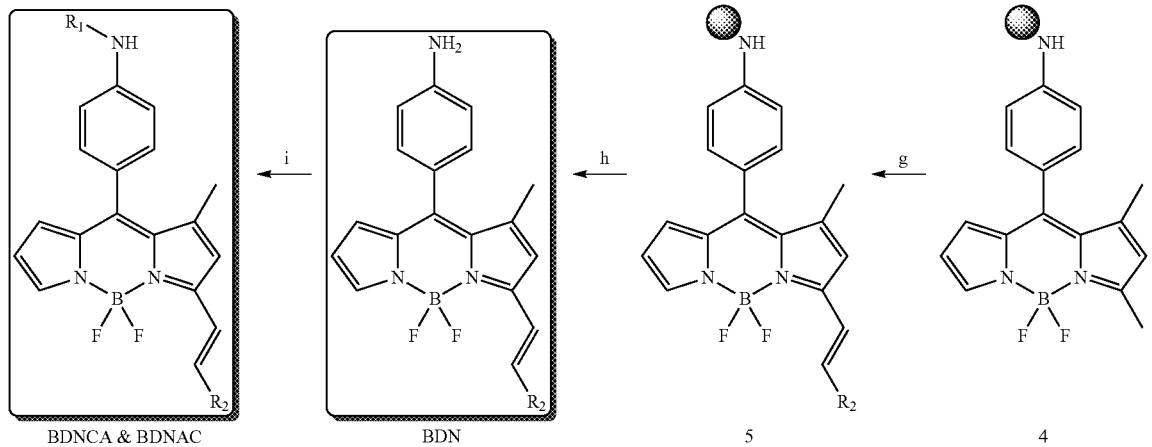

a. MeMgBr, THF, -78-25° C., overnight; b. NaBH$_4$, 0-25° C., THF:MeOH (10:1), 2 h; c. 2,4-Dimethyl pyrrole, InCl$_3$, DCM; d. DDQ in DCM, then BF$_3$·Et$_2$O, TEA; e. Pd/C, hydrazine, monohydrate, EtOH, reflux, 2 h; f. 2-Chlorotrityl resin, pyridine; g. pyrrolidine, R$_2$CHO, 300 W μ-wave, 2 min, NMP:nBuOH (4:1); h. 0.5% TFA in DCM; i. R$_1$(CO)Cl, NaHCO$_3$ sat. soln.

wherein:

R₁ is hydrogen or —COR₃;

R₂ is (C₆-C₁₆)aryl, (C₃-C₁₀)heteroaryl, (C₁-C₆)alkyl, (C₁-C₆)cycloalkyl, (C₂-C₆)alkenyl, or C≡CH;

R₂ is optionally substituted with 1-5 substituents independently selected from (C₁-C₆)alkyl, halogen, amino, cyano, —COOH, halo(C₁-C₆)alkyl, hydroxy(C₀-C₆)alkyl, (C₆-C₁₀)aryl, (C₃-C₁₀)heteroaryl, halo(C₆-C₁₀)aryl, hydroxy(C₆-C₁₀)aryl, (C₁-C₆)alkoxy, halo(C₁-C₆)alkoxy, (C₆-C₁₆)aryloxy, (C₃-C₈)cycloalkyl, halo(C₆-C₁₀)aryl(C₁-C₆)alkoxy, (C₁-C₆)alkoxy(C₆-C₁₀)aryl(C₁-C₆)alkoxy, nitro, (C₀-C₆)alkyl(C₆-C₁₀)aryl(C₀-C₆)alkoxy, (C₅-C₁₀)heterocycle, —OCHF₂, —OCF₃, —SCF₃, —OBn, cyano(C₁-C₆)alkylene, (C₁-C₆)alkoxyamino, (C₆-C₁₀)aryl(C₂-C₆)alkenyl, (C₂-C₆)alkenyl(C₁-C₆)alkoxy, (C₂-C₆)alkenyl, (C₂-C₆)alkenyl(C₆-C₁₀)aryl, —N((C₀-C₆)alkyl)((C₁-C₆)alkyl), —N((C₁-C₆)alkyleneOH)((C₁-C₆)alkyleneOH), —N((C₀-C₆)alkyl)((C₁-C₆)alkyleneOH), —N((C₁-C₆)alkyleneOCO(C₁-C₆)alkyl)((C₁-C₆)alkyleneOCO(C₁-C₆)alkyl), —NCO(C₁-C₆)alkyl, —NPh₂, —OPh(halogen)₀₋₃, —OPhO(C₁-C₆)alkyl, —OPhO(C₁-C₆)alkyl, —OCO(C₁-C₆)alkyl, —OCO(C₁-C₆)alkoxy, —O(C₁-C₆)alkyl(C₆-C₁₀)aryl, —O(C₂-C₆)alkenyl, —O(C₂-C₆)alkyleneN(CH₃)₂, (C₀-C₆)alkylCOO(C₁-C₆)alkyl, —B(OH)₂ or —S(C₁-C₆)alkyl; and wherein any of the substituents selected from (C₁-C₆)alkyl, (C₁-C₆)alkoxy, (C₆-C₁₀)aryl, (C₆-C₁₆)aryloxy or (C₅-C₁₀)heteroaryl is further optionally substituted with 1-4 substituents selected from halogen, (C₁-C₆)alkyl, halo(C₁-C₆)alkyl, amino, nitro, cyano, hydroxy(C₀-C₆)alkyl, (C₁-C₆)alkoxy, —COO(C₀-C₆)alkyl, or —CHO; and R₃ is (C₁-C₁₅)alkyl, (C₂-C₁₅)alkenyl, (C₂-C₁₅)alkynyl, (C₆-C₁₀)aryl or (C₅-C₁₀)heteroaryl, wherein R₃ is optionally substituted with 1-4 substituents independently selected from halogen, amino, cyano or hydroxyl.

In another embodiment, compounds of the present invention are represented by Formula (I), wherein:

R₁ is hydrogen or —COR₃;

R₂ is (C₆-C₁₀)aryl, (C₅-C₁₀)heteroaryl or (C₁-C₆)alkyl;

R₂ is optionally substituted with 1-4 substituents independently selected from (C₁-C₆)alkyl, halogen, amino, cyano, halo(C₁-C₆)alkyl, hydroxy(C₀-C₆)alkyl, (C₆-C₁₀)aryl, (C₅-C₁₀)heteroaryl, halo(C₆-C₁₀)aryl, hydroxy(C₆-C₁₀)aryl, (C₁-C₆)alkoxy, halo(C₁-C₆)alkoxy, (C₃-C₈)cycloalkyl, halo(C₆-C₁₀)aryl(C₁-C₆)alkoxy, (C₁-C₆)alkoxy(C₆-C₁₀)aryl(C₁-C₆)alkoxy, nitro, (C₀-C₆)alkyl(C₆-C₁₀)aryl(C₀-C₆)alkoxy, (C₅-C₁₀)heterocycle, —OCHF₂, —OCF₃, —OBn, cyano(C₁-C₆)alkylene, (C₁-C₆)alkoxyamino, (C₆-C₁₀)aryl(C₂-C₆)alkenyl, (C₂-C₆)alkenyl(C₁-C₆)alkoxy, (C₂-C₆)alkenyl, (C₂-C₆)alkenyl(C₆-C₁₀)aryl, —N(C₀-C₆)alkyl(C₁-C₆)alkyl, —N(C₁-C₆)alkyleneOH(C₁-C₆)alkyleneOH, —N(C₀-C₆)alkyl(C₁-C₆)alkylOH, —NPh₂, —OPh(halogen)₀₋₃, —OPhO(C₁-C₆)alkyl, —OPhO(C₁-C₆)alkyl, —OCO(C₁-C₆)alkyl, —O(C₁-C₆)alkyl(C₆-C₁₀)aryl, —O(C₂-C₆)alkenyl, —O(C₂-C₆)alkyleneN(CH₃)₂, (C₀-C₆)alkylCOO(C₁-C₆)alkyl, —B(OH)₂ or —S(C₁-C₆)alkyl; and wherein any of the substituents selected from (C₁-C₆)alkyl, (C₁-C₆)alkoxy, (C₆-C₁₀)aryl, or (C₅-C₁₀)heteroaryl is further optionally substituted with 1-4 substituents selected from halogen, (C₁-C₆)alkyl, amino, nitro, cyano, hydroxy(C₀-C₆)alkyl, (C₁-C₆)alkoxy, or —HC=O; and R₃ is (C₁-C₁₅)alkyl, (C₂-C₁₅)alkenyl, (C₂-C₁₅)alkynyl, (C₆-C₁₀)aryl or (C₅-C₁₀)heteroaryl, wherein R₃ is optionally substituted with 1-4 substituents independently selected from halogen, amino, cyano or hydroxyl.

In a preferred embodiment of the invention, R₂ is phenyl, optionally substituted to 1-4 substituents selected from (C₁-C₆)alkyl and (C₁-C₆)alkoxy. In a more preferred embodiment, a compound of the invention is a compound of formula (II):

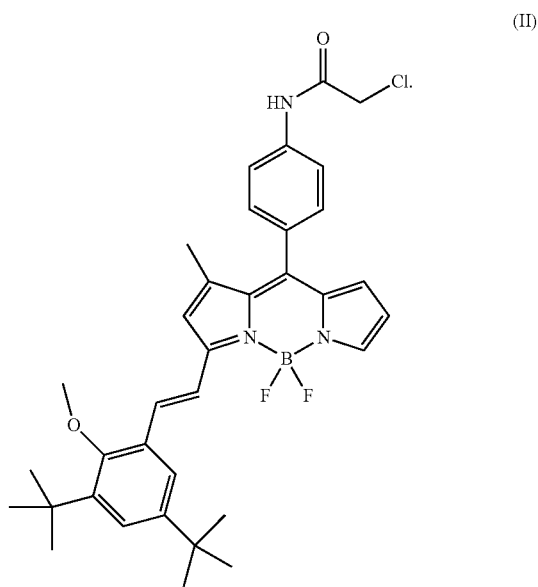

(II)

In another preferred embodiment of the invention, a compound of formula (III) is disclosed:

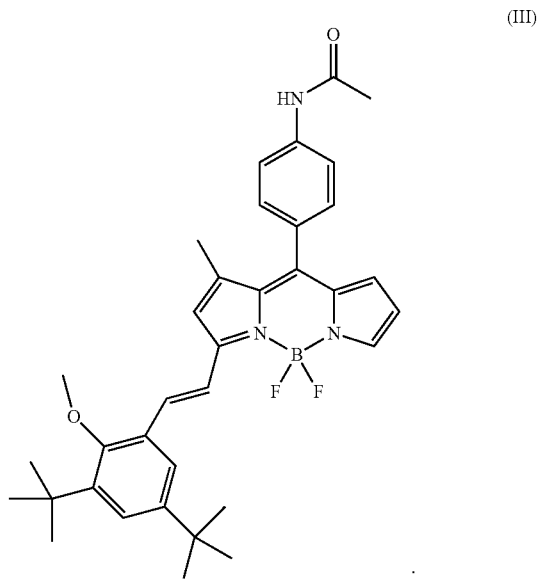

(III)

In another preferred embodiment, a compound of the invention is a compound of formula (IV):

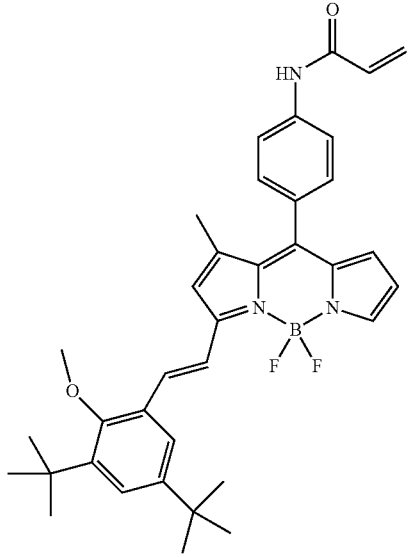

(IV)

In another preferred embodiment of the invention, the compound has the formula (V):

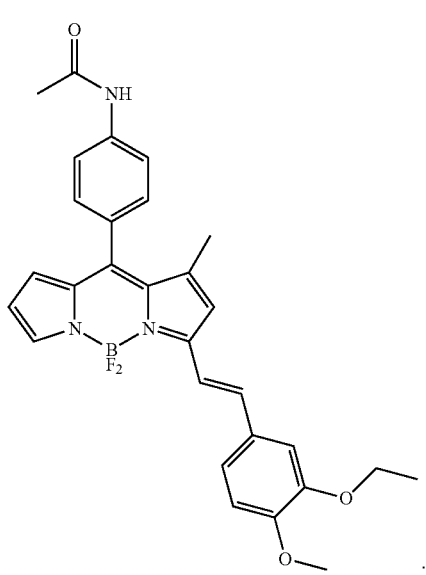

(V)

Alternately, the compound of formula (V) may be chlorinated, represented by formula (VI).

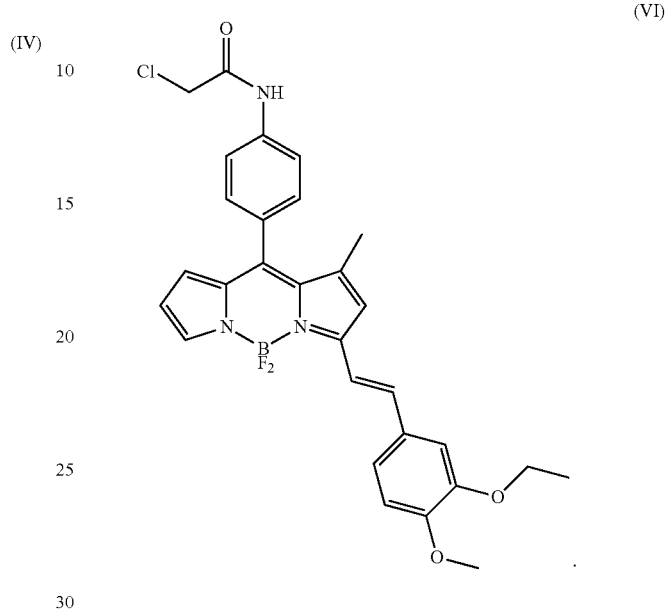

(VI)

Further, any combination of substituents set forth in Table 2 are embodiments of the present invention.

Also described herein are methods of synthesizing the BODIPY fluorescent sensors of the present invention. The invention provides solid-phase methods of synthesizing compounds of Formula (I), which comprises the steps:

(a) reacting a compound of structural Formula (VII):

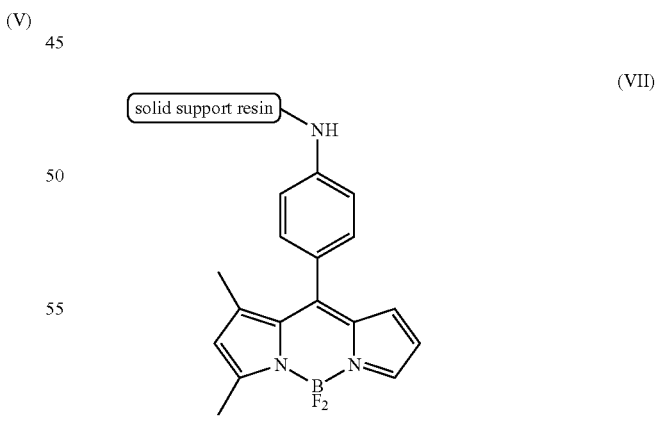

(VII)

with a base and an aldehyde, such that the activated C$_3$-methyl group of Formula (VII) is modified in a solid-phase Knoevenagel-type reaction to produce a compound of Formula VIII:

(VIII)

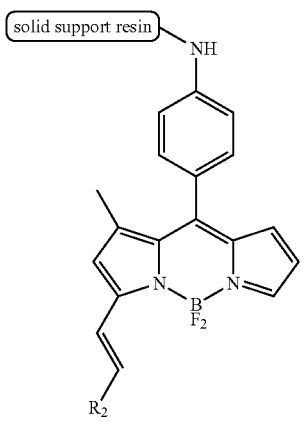

wherein R$_2$ is defined as it is in Formula (I);
b) removing the solid support resin from the compound of structural Formula (VIII) to generate a BODIPY structure of Formula (IX):

(IX)

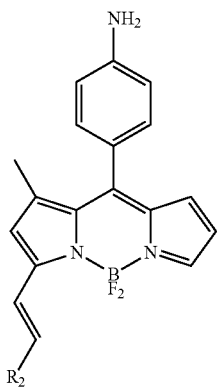

wherein R$_2$ is defined as it is in Formula (I);
c) optionally reacting the compound of structural Formula (IX) with an acid chloride of the formula R$_1$(CO)Cl to generate a compound of structural Formula (I), wherein R$_1$ is defined as in Formula (I).

In some embodiments of the invention, the solid support resin is 2-chlorotrityl polystyrene resin (CT-PS). The base in the Knoevenagel-type reaction is an amine base, such as pyrrole, piperidine, triethylamine, pyrrolidine, or pyridine. In a preferred embodiment of the invention, the base is pyrrolidine. Furthermore, the solvent that the Knoevenagel reaction is carried out in is N-Methyl-2-pyrrolidone, n-butanol, or any combination thereof. In some embodiments of the invention, the CT-PS resin is removed with an organic acid (e.g. R—COOH) or a mineral acid. In a preferred embodiment of the invention, the removal of the CT-PS resin is carried out with trifluoroacetic acid, and is carried out in a chlorinated solvent such as chloroform, methylene chloride, dichloroethane, and most preferably, methylene chloride.

The BODIPY structure of Formula (IX) is a compound of structural formula (I) and therefore a novel compound of the invention. The aniline moiety of Formula (IX) may be further substituted by reaction with an acid chloride (e.g. R$_1$COCl), to install the R$_1$ substituent of Formula (I). A compound of Formula (IX) is optionally reacted with an acid chloride to modify the aniline moiety. The aniline substitution reaction is carried out with aqueous base solution, preferably NaHCO$_3$.

Another embodiment of the invention are methods for detecting beta-cells using image based screening, comprising: a) contacting a sample comprising pancreas cells with a compound of structural Formula (I) or a pharmaceutically acceptable salt thereof, wherein the compound of Formula (I) is described above; b) incubating the sample and the compound of step a) together for a period of time sufficient to stain the cells; and c) analyzing the incubated dye-stained cells by spectroscopy to detect a fluorescence signal, wherein the presence of a fluorescence signal indicates the presence of beta-cells.

In one embodiment of the invention, the sample that is used in the method for detecting beta-cells is isolated mouse pancreas. In a preferred embodiment of the invention, the sample is a pancreatic tissue section or isolated pancreas islets. In another embodiment of the invention, the sample is thought to comprise beta-cells. The methods for detecting beta-cells described herein are selective for the detection of beta-cells over other cell types. The methods for detecting beta-cells are used in an in vitro application. Alternately, the methods of the invention are used in an in vivo application. When the methods of detecting beta-cells are for use in vitro analysis, a preferred embodiment of the invention utilizes a BODIPY dye of Formula (II), called BDNCA 325. When the methods of detecting beta-cells are for use in vivo analysis, a preferred embodiment of the invention utilizes a BODIPY dye of Formula (III), called BDNAC 325. Further, the beta-cells are preferably pancreatic islet cells. In some embodiments of the invention, the period of time in which the sample and BODIPY dye is incubated together is from about 1 hour to about 48 hours. In a preferred embodiment of the invention, the period of time in which the sample and BODIPY dye is incubated together is from about 1 hour to about 24 hours. In some embodiments of the invention, the incubated mixture is analyzed by fluorescence microscope. The methods disclosed in the present invention analyze a sample by a fluorescent signal, wherein the presence of the signal is indicative of the presence of the beta-cells.

According to one embodiment of the invention, cells of interest can be screened using a negative control cell type to determine the selectivity of the specific compounds of the invention to cells that are being detected. Such negative control for detection of the beta-cell is, for example, an acinar cell.

Another embodiment of the invention provides methods for detecting microglia cells, comprising: a) contacting a sample comprising cells with a compound of structural Formula (I) or a pharmaceutically acceptable salt thereof; b) incubating the sample and compound of step a) together for a period of time sufficient to stain the cells; and c) analyzing the incubated stained cells by spectroscopy, wherein the presence of a fluorescence signal is indicative of the presence of the microglia cells In one embodiment of the invention, the sample that is used in the methods for detecting microglia cells is a primary neural cell culture or a microglia-derived cell line culture such as BV2 microglia cell line. In another embodiment of the invention, the sample is thought to comprise beta cells. The methods described herein for detecting microglia cells are selective for the detection of microglia cells over primary neural cells and other cell types. Further, BODIPY dye utilized in the methods for detecting microglia cells described herein does not affect cellular function and is not cytotoxic. The methods for detecting microglia cells are for use in vitro, or alternatively in vivo. In one aspect of the invention, the BODIPY dye is modified with a radioactive isotope such as $^{18}$F or $^{11}$C, enabling detection of the compound by PET analysis in vivo applications. A preferred compound of Formula (I) used in the detection of microglia cells is a BODIPY dye of Formula (VI), called BDNCA 164 or BDNCA1 H5. In a preferred embodiment of the invention, the sample and compound are incubated together for about one hour. In another aspect of the invention, the incubated mixture is washed in fresh media for about one hour. In some embodiments of the invention, the incubated mixture is analyzed by fluorescence microscope or flow cytometry. The methods disclosed in the present invention analyze a sample by a fluorescent signal, wherein the presence of the signal is indicative of the presence of microglia cells.

The negative control for microglia screening is, for example, neuronal stem cell, primary neuron cell or astrocyte cell. In the preferred embodiment the dye is BDNCA164. In one aspect of the invention, the BODIPY dye staining is localized in the mitochondria of the microglia cells. In a further embodiment of the invention, the method of detecting microglia cells can discriminate between resting and activated microglia cells. Utilizing BODIPY dye BDNCA 164, activated microglia cells are visualized with fluorescence intensity about 2-times greater than resting microglia cells. In some embodiments of the invention, the fluorescence intensity is measured by fluorescence microscopy or by flow cytometry.

Another embodiment of the invention provides methods for fluorescence imaging of pancreatic islet cells to determine health status of the pancreatic islet cells, comprising: a) contacting the pancreatic islet cells with a compound of structural Formula (I) or a pharmaceutically acceptable salt thereof; b) incubating the cells and the compound of step a) together for a period of time sufficient to stain the cells; c) analyzing the incubated stained pancreatic islet cells by fluorescent microscopy to detect a fluorescence signal; and d) comparing the signal from step c) to a signal from reference sample of healthy pancreatic islet cells, to determine health status of the pancreatic islet cells.

According to one embodiment of the invention, healthy pancreatic islet cells are preferentially stained with the fluorescent BODIPY dye compounds of the invention. Without being bound to theory, it is believed that healthy pancreatic islet cells are preferentially stained because the healthy pancreatic islet cells are surrounded by beta cells that are stainable, whereas the beta cells are broken down around the diseased cells and thereby the diseased cells are not stained. The methods for determining health status by imaging of pancreatic islets are used in an in vitro application. Alternately, the methods are used in an in vivo application. When the methods of imaging pancreatic islets are for use in an in vitro application, a preferred embodiment of the invention utilizes a BODIPY dye of Formula (II), called BDNCA 325. When the methods of detecting beta-cells are for use in an in vivo application, a preferred embodiment of the invention utilizes a BODIPY dye of Formula (III), called BDNAC 325, or PiY.

In some embodiments of the invention, the period of time in which the sample and the BODIPY dye is incubated together is from about 0.5 hours to about 4 hours. Preferably, the incubation time is from about 0.5 hour to about 1 hour. Health status of the pancreatic islets can be determined by comparing the fluorescence of the test sample to a reference sample. In one embodiment, the reference sample is a sample of healthy pancreatic cells. The signal characteristics that are compared can be, but are not limited to, fluorescence intensity, staining localization, selectivity among cell type and tissue, or quantification by signal intensity. A fluorescence signal and its signal characteristics are ascertained through spectroscopy or fluorescence microscopy using a fluorometer, UV/VIS spectrometer, Gemini XS fluorescence plate reader, flow cytometry or a confocal microscope.

The methods described herein can be performed in vitro or in vivo to ascertain, for example, the status or location of target cells, for example, the in vivo methods can be used to probe for pancreatic transplants in a patient or study microglia related inflammation. The methods can be performed on a mammal, preferably human.

Definitions

"Alkyl" means a saturated aliphatic branched or straight-chain monovalent hydrocarbon radicals, typically $C_1$-$C_{10}$, preferably $C_1$-$C_6$. "($C_1$-$C_6$) alkyl" means a radical having from 1-6 carbon atoms in a linear or branched arrangement. "($C_1$-$C_6$)alkyl" includes methyl, ethyl, propyl, butyl, tert-butyl, pentyl and hexyl.

"Alkylene" means a saturated aliphatic straight-chain divalent hydrocarbon radical. Thus, "($C_1$-$C_6$)alkylene" means a divalent saturated aliphatic radical having from 1-6 carbon atoms in a linear arrangement. "($C_1$-$C_6$)alkylene" includes methylene, ethylene, propylene, butylene, pentylene and hexylene.

"Heterocycle" means a saturated or partially unsaturated (3-7 membered) monocyclic heterocyclic ring containing one nitrogen atom and optionally 1 additional heteroatom independently selected from N, O or S. When one heteroatom is S, it can be optionally mono- or di-oxygenated (i.e., —S(O)— or —S(O)$_2$—). Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, or isothiazolidine 1,1-dioxide.

"Cycloalkyl" means saturated aliphatic cyclic hydrocarbon ring. Thus, "$C_3$-$C_7$ cycloalkyl" means (3-7 membered) saturated aliphatic cyclic hydrocarbon ring. $C_3$-$C_7$ cycloalkyl includes, but is not limited to cyclopropyl, cyclobutyl, cyclopentyl, cyclohexyl and cycloheptyl. Preferably, cycloalkyl is $C_1$-$C_6$ cycloalkyl.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$)alkyl and includes methoxy, ethoxy, propoxy, butoxy, pentoxy and hexoxy.

"Cycloalkoxy" means an cycloalkyl-O— group wherein the cycloalkyl is as defined above. Exemplary ($C_3$-$C_7$) cycloalkyloxy groups include cyclopropoxy, cyclobutoxy, cyclopentoxy, cyclohexoxy and cycloheptoxy.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

As used herein, an amino group may be a primary (—NH$_2$), secondary (—NHR$_x$), or tertiary (—NR$_x$R$_y$), wherein R$_x$ and R$_y$ may be any of the optionally substituted alkyls described above. An amino group may include cyclic amino groups such as piperidine and pyrrolidine.

The terms "haloalkyl", "halocycloalkyl" and "haloalkoxy" mean alkyl, cycloalkyl, or alkoxy, as the case may be, substituted with one or more halogen atoms. The term "halogen" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH═CH—.

The term "(C$_6$-C$_{16}$)aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-16 ring atoms. A "substituted aryl group" is substituted at any one or more substitutable ring atom. The term "C$_6$-C$_{16}$ aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like.

The term benzyl (Bn) refers to —CH$_2$Ph.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen total ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 total atoms of which, unless otherwise specified, one, two, three, four or five are heteroatoms independently selected from N, NH, N(C$_{1-6}$alkyl), O and S. (C$_3$-C$_{10}$)heteroaryl includes furyl, thiophenyl, pyridinyl, pyrrolyl, imidazolyl, and in preferred embodiments of the invention, heteroaryl is (C$_3$-C$_{10}$)heteroaryl.

The term "2-4 member polycyclyl" is a cyclic compound with 2-4 hydrocarbon loop or ring structures (e.g., benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these.

The term "Alkenyl" means a straight or branched hydrocarbon radical having a specified number of carbon atoms and includes at least one double bond. The (C$_6$-C$_{10}$)aryl(C$_2$-C$_6$)alkenyl group connects to the remainder of the molecule through the (C$_2$-C$_6$)alkenyl portion of (C$_6$-C$_{10}$)aryl(C$_2$-C$_6$)alkenyl.

Another embodiment of the present invention are a pharmaceutical compositions comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e., a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

"CT-PS resin" is a resin used in solid phase synthesis. Specifically, it is 2-chlorotrityl-polystyrene.

A "cellular extract" is lysed cells from which insoluble matter has been removed via centrifugation.

A "tissue section" is a portion of tissue suitable for analysis. A tissue section can refer to a single tissue section or a plurality of tissue sections.

As used herein, "spectroscopy" encompasses any method by which matter reacts with radiated energy. This includes, but is in no way limited to, microscopy, fluorescence microscopy, UV/Vis spectrometry, and flow cytometry.

EXAMPLES

The following examples are provided to illustrate one or more preferred embodiments of the invention, but are not limited embodiments thereof. Numerous variations can be made to the following examples that lie within the scope of the invention.

Example 1

Synthetic Protocol for the BODIPY Dye Compounds of the Invention

Using inexpensive starting materials (pyrrole and nitrobenzoyl chloride), Compound 1 was prepared according to the following method:

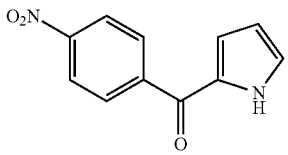

(4-nitrophenyl)(1H-pyrrol-2-yl)methanone (1). CH$_3$MgBr (3M) in diethylether (30 mL, 90 mmol) was added by dropwise to the solution of pyrrole (6.95 mL, 100 mmol) in THF (150 mL) at −78° C. and continued for 1 h at r.t. 4-nitrobenzoyl chloride (13 g, 70 mmol) in THF (200 mL) was added by dropwise to the solution and stirring was continued for 3 hours at r.t. The mixture was poured into saturated aqueous NH$_4$Cl, and the precipitate dissolved in DCM and added to the aqueous solution. The organic layer was washed with water, dried over MgSO$_4$ and concentrated under vacuum to give an oily product. Compound 1 was isolated by chromatography on silica gel flash column eluting with EtOAc/Hex to furnish a yellow solid (12.4 g, 81%). $^1$H-NMR (CDCl$_3$) δ 10.01 (bs, 1H, NH), 8.34 (d, J=8.4, 2H), 8.03 (d, J=8.7, 2H), 7.24 (bs, 1H), 6.86 (bs, 1H), 6.38 (bs, 1H); $^{13}$C-NMR (CDCl$_3$) δ 182.51, 149.61, 143.62, 130.57, 129.74, 126.67, 123.55, 120.37, 111.69. ESI-MS m/z (M+H) calc'd: 217.0 found 216.9.

Further condensation with 2,4-dimethylpyrrole and InCl$_3$, followed by in situ addition of the BF$_3$.OEt$_2$ yielded BODIPY derivative 2.

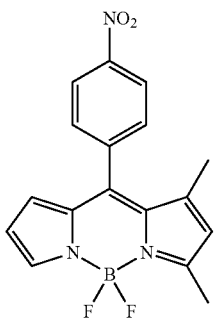

4,4-Difluoro-1,3-dimethyl-8-(4-nitrophenyl)-4-bora-3a,4a-diaza-s-indacene (2). A solution of compound 1 (8.64 g, 40 mmol) in THF/MeOH (110 mL, 10:1) was treated with NaBH$_4$ (3.03 g, 80 mmol) at r.t. for 1 h. The reaction mixture was poured in a mixture of saturated aqueous NH$_4$Cl (100 mL) and EtOAc (200 mL). The organic phase was separated, washed with water, dried (Na$_2$SO$_4$), and concentrated to dryness, affording crude yellow oil (8.38 g, 38.8 mmol). The crude reduced alcohol product was used directly without purification due to the instability.

A mixture of the resulting residue and 2,4-dimethylpyrrole (4.02 mL, 39 mmol) was dissolved in DCM (100 mL) and treated with InCl$_3$(858 mg, 3.88 mmol) at room temperature. After 3 hours, the reaction mixture was quenched with triethylamine (557 μL, 4 mmol). The organic layer was concentrated, and silica gel filtered with DCM, affording crude compound of coupled dipyrrole (7.37 g, 25 mmol), which was used directly in next step.

To a solution of dipyrrole (7.37 g, 25 mmol) in toluene (100 mL) was added DDQ (5.7 g, 25 mmol) in DCM (20 mL). The mixture was stirred 15 min at r.t. A solution of reaction mixture was cooled under N$_2$ to 0° C. Triethylamine (21 mL, 150 mmol) was added for neutralization. After 2 min of stirring, BF$_3$.OEt$_2$ (31 mL, 250 mmol) was added dropwise, over 10 min. Thereafter, the mixture was stirred for 8 h at rt. The reaction solution was filtered through short panel of silica gel with DCM-Hex (1:2) solution, affording crude compound 2. Compound 2 was purified by column chromatography on silica after removal of reaction solvent (8.21 g, 24.1 mmol).
$^1$H-NMR (CDCl$_3$) δ 8.38 (d, J=8.7, 2H), 7.71 (s, 1H), 7.57 (d, J=8.4, 2H), 6.39 (s, 1H), 6.30 (d, J=3.3, 1H), 6.18 (s, 1H), 2.64 (s, 3H), 1.49 (s, 3H); $^{13}$C-NMR (CDCl$_3$) δ 163.58, 148.59, 146.43, 140.67, 139.87, 139.67, 133.78, 130.07, 128.79, 126.69, 123.93, 123.74, 116.67, 29.67, 15.25, 15.15. ESI-MS m/z (M+H) calc'd: 342.1, found: 342.0.

The nitro group of 2 was converted to a primary amine under reductive conditions.

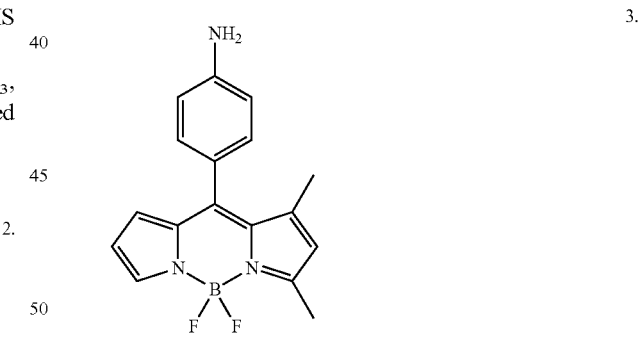

4,4-Difluoro-1,3-dimethyl-8-(4-aminoophenyl)-4-bora-3a,4a-diaza-s-indacene (3). A solution of compound 2 (8.21 g, 24.1 mmol) in EtOH (100 mL) was purged with N$_2$ for 10 min. Hydrazine monohydrate (5.81 mL) and 10% Pd/C (100 mg) were added. The mixture was refluxed under N$_2$ for 2 hours. Then Pd/C was removed under celite filtration. After evaporation of the solvent, the residue was dry-loaded onto a silica gel flash column and eluted using EtOAc/Hex to afford an orange solid (5.85 g, 18.8 mmol). $^1$H-NMR (CDCl$_3$) δ 7.65 (s, 1H), 7.13 (d, J=8.4, 2H), 6.75 (d, J=8.1, 2H), 6.52 (d, J=3.3, 1H), 6.37 (d, J=1.8, 1H), 6.12 (s, 1H), 2.61 (s, 3H), 1.67 (s, 3H); $^{13}$C-NMR (CDCl$_3$) δ 161.00, 147.64, 146.70, 144.44, 138.02, 135.01, 133.69, 130.39, 126.92, 123.77, 122.88, 115.74, 114.57, 29.65, 15.43, 15.03: ESI-MS m/z (M+H) calc'd: 312.1, found: 312.4.

Loading of BODIPY on 2-Chlorotrityl Resin.

The aminophenyl BODIPY (3) was loaded to 2-chlorotrityl resin. In DCM solvent aminophenyl BODIPY compound 3 and pyridine (5 equiv) were diluted and added to pre-swelled 3 equiv. of 2-chlorotrityl resin (1 mmol/g) and kept shaking 12 h. 20 equiv. methanol was added for quenching of extra chloride on resin. After 1 h shaking for quenching, resin was washed with DMF, MeOH, DCM and dried with high vacuum pump.

Condensation Reaction with Aldehyde and Cleavage.

The red bead (150 mg, 50 μmole) was placed in 20 mL capped vial swell with 4 mL of NMP/n-BuOH (4/1) and operated in microwave chamber with 300 W power for 2 minutes, monitoring the color change it was repeated until black color was appeared. The black color resin was washed with DMF, MeOH, DCM and directly cleaved by 0.5% of TFA in DCM solution for 10 minutes and repeated twice. Generated compounds were purified on silica packed syringe with EtOAc/Hex solvent.

Acylation of BDN Compounds:

Purified aniline BODIPY compound was diluted in DCM/ACN (2/1), 10 μL of NaHCO$_3$ saturated solution was added and acid chloride (5 equiv.) was added immediately. The organic layer was washed with NaHCO$_3$ saturated solution twice.

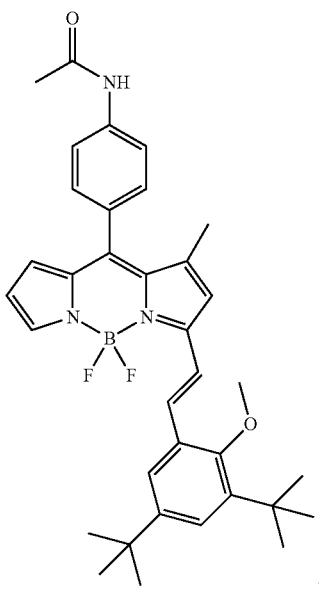

BDNAC 325

Characterization of BDNAC 325. $^1$H-NMR (CDCl$_3$) δ 7.72 (m, 6H), 7.60 (d, J=2.4 Hz, 1H), 7.42 (d, J=2.4 Hz, 1H), 7.30 (s, 1H) 6.81 (s, 1H), 6.43 (m, 2H), 3.8 (s, 3H), 2.27 (s, 3H), 1.45 (s, 9H), 1.39 (s, 9H); $^{13}$C-NMR (CDCl$_3$) δ 166.16, 164.25, 162.80, 157.87, 156.88, 151.60, 146.14, 145.84, 144.99, 142.19, 139.31, 138.02, 136.75, 135.87, 129.80, 129.63, 129.16, 127.46, 127.11, 126.34, 126.31, 126.24, 122.80, 119.49, 119.21, 118.75, 112.80, 104.96, 63.31, 60.39, 35.23, 34.64, 31.44, 30.93, 29.67, 24.67, 21.81, 15.50, 15.47, 14.18, 10.21.; ESI-MS m/z (M+H) calc'd: 584.31, found 584.30.

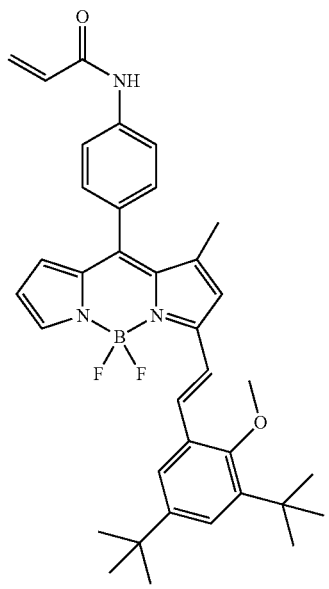

BDN 325-7

Characterization of BDN 325-7. $^1$H-NMR (CDCl$_3$) δ 7.72 (m, 6H), 7.57 (d, J=2.1 Hz, 1H), 7.38 (d, J=2.1 Hz, 1H), 7.32 (d, J=8.7 Hz, 2H), 6.77 (s, 1H), 6.45 (m, 1H), 6.39 (m, 2H), 6.30 (m, 1H), 5.78 (dd, J=1.2, 10.2, 1H), 3.78 (s, 3H), 1.64 (s, 3H), 1.41 (s, 9H), 1.35 (s, 9H); $^{13}$C-NMR (CDCl$_3$) 163.73, 159.93, 158.67, 156.91, 151.28, 146.16, 145.82, 143.42, 142.24, 141.10, 139.09, 138.04, 136.87, 135.04, 130.879, 129.95, 129.86, 129.13, 128.40, 126.37, 126.25, 122.79, 119.48, 119.45, 119.30, 118.72, 118.69, 116.096, 63.33, 35.24, 34.64, 31.44, 30.94, 29.68, 15.53, 14.10, ESI-MS m/z (M+H) calc'd: 596.32, found 596.30.

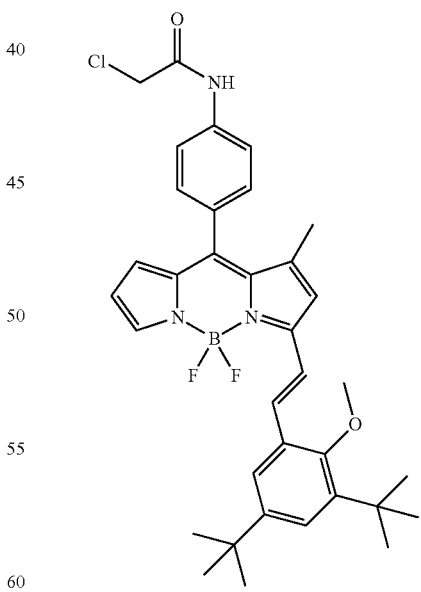

BDNCA 325

Characterization of BDNCA 325. $^1$H-NMR (CDCl$_3$) δ 8.40 (s, 1H), 7.72 (m, 5H), 7.57 (d, J=2.4 Hz, 1H), 7.39 (m, 3H), 6.78 (s, 1H), 6.40 (bs, 2H), 4.2 (s, 2H), 3.79 (s, 3H), 1.64 (s, 3H), 1.42 (s, 9H), 1.36 (s, 9H); $^{13}$C-NMR (CDCl$_3$) 163.98, 158.85, 156.92, 146.18, 145.69, 142.21, 140.66, 138.20, 137.83, 136.95, 134.87, 130.92, 129.99, 129.16, 126.38, 126.13, 122.84, 119.64, 119.34, 118.74, 116.09, 104.96, 102.33, 101.02, 63.35, 42.88, 35.26, 34.66, 31.46, 30.96, 29.69, 15.50, ESI-MS m/z (M+H) calc'd: 618.18, found 618.30

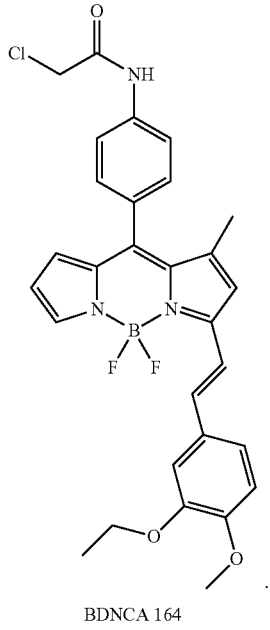

BDNCA 164

Characterization of BDNCA 164. $^1$H-NMR (CD$_3$OD+ CDCl$_3$) δ 8.36 (s, 1H), 7.71 (m, 3H), 7.55 (d, J=16.0 Hz, 1H), 7.39 (d, J=8.5 Hz, 2H), 7.33 (d, J=16.0 Hz, 1H), 7.17 (m, 2H), 6.88 (d, J=9.0 Hz, 1H), 6.72 (s, 1H), 6.38 (bs, 2H), 4.25 (s, 2H), 4.18 (m, 2H), 3.92 (s, 3H), 1.63 (s, 3H), 1.50 (t, J=7 Hz, 3H), $^{13}$C-NMR (CDCl$_3$) δ 165.35, 158.33, 150.99, 148.28, 145.69, 140.13, 138.52, 136.95, 134.65, 129.95, 129.49, 128.76, 122.30, 119.42, 119.12, 115.96, 111.15, 110.86, 64.30, 55.57, 42.66, 29.31, 15.01, 14.22; ESI-MS m/z (M+H) calc'd: 550.18, found 550.20, 530.20 (M−F)

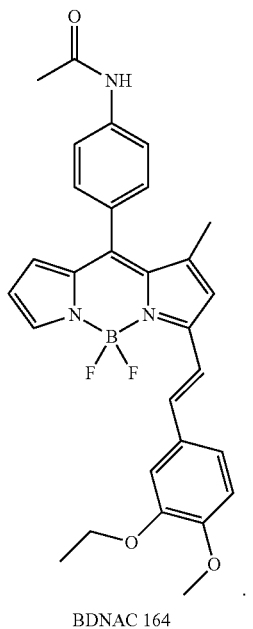

BDNAC 164

Characterization of BDNAC 164; $^1$H-NMR (CD$_3$OD+ CDCl$_3$) δ 8.46 (s, 1H), 7.76 (m, 3H), 7.65 (d, J=16.0 Hz, 1H), 7.43 (d, J=8.5 Hz, 2H), 7.32 (d, J=16.0 Hz, 1H), 7.19 (m, 2H), 6.89 (d, J=9.0 Hz, 1H), 6.75 (s, 1H), 6.39 (bs, 2H), 2H), 4.20 (m, 2H), 3.95 (s, 3H), 2.04 (s, 3H), 1.71 (s, 3H), 1.49 (t, J=7 Hz, 3H), $^{13}$C-NMR (CDCl$_3$) δ 165.45, 159.33, 151.99, 147.28, 146.69, 140.33, 138.55, 136.98, 134.65, 129.95, 129.49, 128.76, 123.30, 119.52, 119.82, 114.96, 112.15, 110.86, 64.30, 55.58, 42.66, 29.51, 15.01, 14.22; ESI-MS m/z (M+H) calc'd: 516.22, found 516.20.

TABLE 1

Spectral information summary of islet probes
Spectral Information

| | BDNAC 325 | BDN 325-7 | BDNCA 325 |
|---|---|---|---|
| Absorption Max | 558 nm | 558 nm | 558 nm |
| Emission Max | 585 nm | 586 nm | 585 nm |
| Quantum Yield | 0.05 | 0.06 | 0.06 |
| Extinction Coefficient | 27700 | 27900 | 27600 |

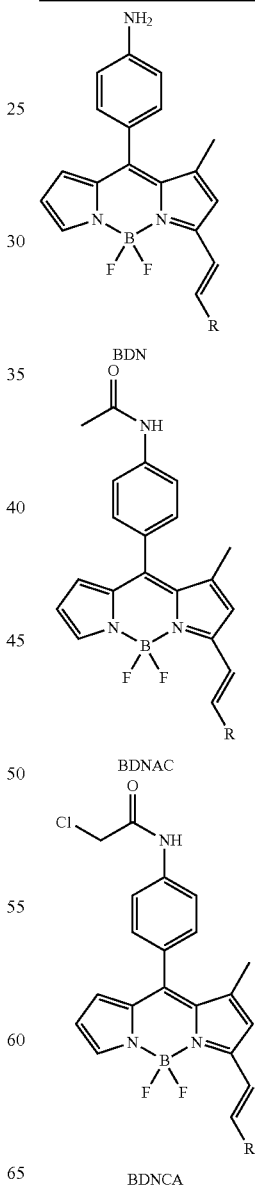

BDN

BDNAC

BDNCA

In each of the above structures, BDN, BDNAC and BDNCA, R is derived from commercially available aldehydes.

The following aldehydes were used in the preparation of the BDN, BDNCA, and BDNAC libraries.

TABLE 2

Aldehyde building blocks for BDN, BDNCA, BDNAC libraries

| ID | Structure |
|---|---|
| L1 | 3,4,5-trimethoxybenzaldehyde |
| L2 | 4-(dimethylamino)benzaldehyde |
| L3 | 4-[(2-cyanoethyl)(methyl)amino]benzaldehyde |
| L4 | 3,4-bis(benzyloxy)benzaldehyde |
| L5 | biphenyl-4-carbaldehyde |
| L6 | anthracene-9-carbaldehyde |
| L7 | 3-(benzyloxy)-4-methoxybenzaldehyde |
| L23 | 4-fluorobenzaldehyde |
| L25 | naphthalene-1-carbaldehyde |
| L27 | benzaldehyde |
| L29 | 3-chloro-4-hydroxy-5-methoxybenzaldehyde |
| L30 | 2,2'-bithiophene-5-carbaldehyde |
| L32 | 4-methoxynaphthalene-1-carbaldehyde |
| L34 | 2-methylnaphthalene-1-carbaldehyde |
| L8 | 4-(1H-imidazol-1-yl)benzaldehyde |
| L9 | 3-methylbenzaldehyde |
| L11 | 3-bromobenzaldehyde |
| L12 | 4-chlorobenzaldehyde |

TABLE 2-continued

Aldehyde building blocks for BDN, BDNCA, BDNAC libraries

| ID | Structure |
|---|---|
| L13 | 3,4-dihydroxy-5-methoxybenzaldehyde |
| L14 | 4-(N,N-diphenylamino)benzaldehyde |
| L15 | 4-cyanobenzaldehyde |
| L16 | 4-(benzyloxy)-3,5-dimethylbenzaldehyde |
| L17 | 4-(dibutylamino)benzaldehyde |
| L36 | 4-methyl-1-naphthaldehyde |
| L37 | benzo[b]thiophene-3-carbaldehyde |
| L38 | 2-chloro-3-hydroxy-4-methoxybenzaldehyde |
| L40 | biphenyl-2-carbaldehyde |
| L41 | 4-formylphenyl acetate |
| L42 | 3-(4-methoxyphenoxy)benzaldehyde |
| L43 | 5-tert-butyl-2-hydroxybenzaldehyde |
| L44 | 4-acetoxy-3-methoxycinnamaldehyde |
| L45 | 4-(hexyloxy)benzaldehyde |
| L18 | 4-(methylthio)benzaldehyde |
| L19 | 4-isopropylbenzaldehyde |
| L20 | 3-phenoxybenzaldehyde |
| L22 | furan-2-carbaldehyde |
| L52 | 4-((4-bromobenzyl)oxy)benzaldehyde |
| L53 | 3,4-diethoxybenzaldehyde |

TABLE 2-continued

Aldehyde building blocks for BDN, BDNCA, BDNAC libraries

| ID | Structure |
|----|-----------|
| L54 | 5-bromo-2-methoxybenzaldehyde |
| L57 | 3,5-dichloro-2-hydroxybenzaldehyde |
| L61 | 2-methoxy-1-naphthaldehyde |
| L46 | 4-butoxybenzaldehyde |
| L48 | 4-(allyloxy)benzaldehyde |
| L49 | 4-(diethoxymethyl)benzaldehyde |
| L51 | quinoline-4-carbaldehyde |
| L83 | 2,3-dimethoxybenzaldehyde |
| L85 | 3,3-diphenylacrylaldehyde |
| L88 | 4-(pyridin-2-yl)benzaldehyde |
| L89 | acenaphthylene-5-carbaldehyde (acenaphthene aldehyde) |
| L90 | 4-(benzyloxy)benzaldehyde |
| L62 | 3,4-dimethoxybenzaldehyde |
| L63 | 4-ethoxy-3-methoxybenzaldehyde |
| L65 | 5-phenylthiophene-2-carbaldehyde |
| L67 | 2,3,4,5,6-pentamethylbenzaldehyde |
| L68 | 4-(trifluoromethoxy)benzaldehyde |
| L69 | 4-styrylbenzaldehyde |
| L70 | 5,7-dimethoxynaphthalene-1-carbaldehyde |

TABLE 2-continued
Aldehyde building blocks for BDN, BDNCA, BDNAC libraries
| ID | Structure |
|---|---|
| L71 | 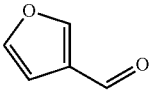 |
| L72 | 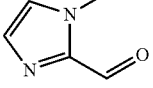 |
| L91 | 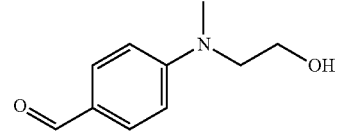 |
| L92 | 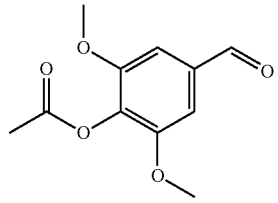 [SMILES: COc1cc(C=O)cc(OC)c1OC(C)=O] |
| L93 | 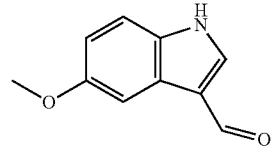 |
| L94 | 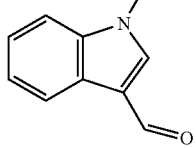 |
| L95 | 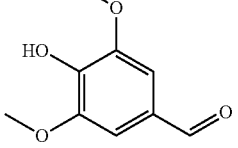 |
| L96 | 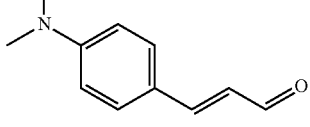 |
| L97 | 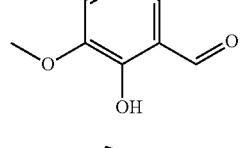 |
| L100 | 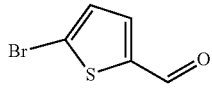 |
| L101 | 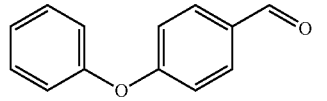 [SMILES: O=Cc1ccc(Oc2ccccc2)cc1] |
| L73 | 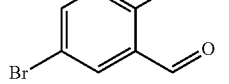 |
| L75 | 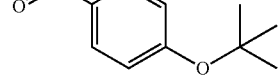 |
| L76 | 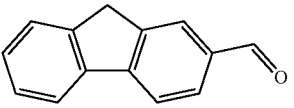 |
| L77 | 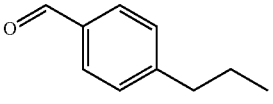 |
| L78 | 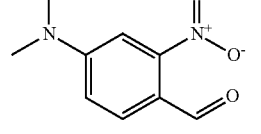 |
| L82 | 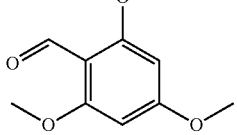 |
| L111 | 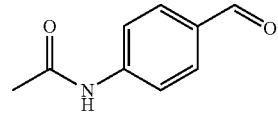 |
| L114 | 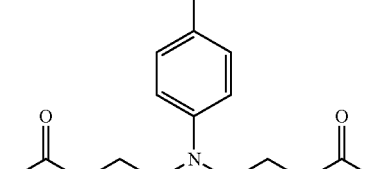 |
| L103 | 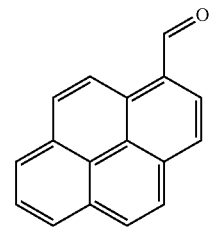 [SMILES: O=Cc1ccc2ccc3cccc4ccc1c2c34] |

TABLE 2-continued

Aldehyde building blocks for BDN, BDNCA, BDNAC libraries

| ID | Structure |
|---|---|
| L105 | 3-hydroxybenzaldehyde |
| L107 | 4-(diethylamino)benzaldehyde |
| L108 | 2,4,6-trimethylbenzaldehyde |
| L109 | 2,5-dimethyl-1-(3-(trifluoromethyl)phenyl)-1H-pyrrole-3-carbaldehyde |
| L110 | 4-methoxybenzaldehyde |
| L178 | 4-(4-methoxyphenoxy)benzaldehyde |
| L179 | methyl 4'-formyl-[1,1'-biphenyl]-4-carboxylate |
| L117 | 4-((tert-butoxycarbonyl)oxy)-3-methylbenzaldehyde |
| L121 | 5-chloro-2-hydroxybenzaldehyde |
| L126 | 3-ethoxy-2-hydroxybenzaldehyde |
| L128 | 2-(2-formylphenoxy)acetic acid |
| L131 | 4-hydroxy-3-nitrobenzaldehyde |
| L132 | 3-hydroxy-4-methoxybenzaldehyde |
| L134 | 5-methyl-1H-imidazole-4-carbaldehyde |
| L135 | 5-methylfuran-2-carbaldehyde |
| L137 | 2-naphthaldehyde |
| L180 | 4-bromothiophene-2-carbaldehyde |
| L182 | 3,4-dichlorobenzaldehyde |
| L185 | 5-bromo-1H-indole-3-carbaldehyde |
| L186 | 3-methoxybenzaldehyde |
| L190 | 2-hydroxybenzaldehyde |
| L191 | 2-formylbenzoic acid |

TABLE 2-continued

Aldehyde building blocks for BDN, BDNCA, BDNAC libraries

| ID | Structure |
|---|---|
| L192 | 2-hydroxy-4-methoxybenzaldehyde |
| L195 | 5-(3-chloro-4-methoxyphenyl)furan-2-carbaldehyde |
| L198 | 2-methoxybenzaldehyde |
| L139 | benzo[d][1,3]dioxole-5-carbaldehyde |
| L140 | 4-propoxybenzaldehyde |
| L143 | 2-methylbenzaldehyde |
| L144 | 2,4,5-trimethoxybenzaldehyde |
| L147 | 2,4-dichlorobenzaldehyde |
| L153 | 4-hydroxybenzaldehyde |
| L163 | 4-(3-(dimethylamino)propoxy)benzaldehyde |
| L164 | 3-ethoxy-4-methoxybenzaldehyde |
| L177 | 4-tert-butylbenzaldehyde |
| L199 | 4-(pyrimidin-5-yl)benzaldehyde |
| L202 | 2-(allyloxy)benzaldehyde |
| L206 | 2,4-dimethoxybenzaldehyde |
| L208 | 4-methylbenzaldehyde |
| L209 | 3,5-dimethoxybenzaldehyde |
| L210 | 2-hydroxy-5-methoxybenzaldehyde |
| L218 | 2-(benzyloxy)benzaldehyde |
| L219 | methyl 4-formylbenzoate |
| L220 | 2,5-dichloro-3-hydroxy-4-methoxybenzaldehyde |
| L223 | 2-(benzyloxy)-4,5-dimethoxybenzaldehyde |

TABLE 2-continued

Aldehyde building blocks for BDN, BDNCA, BDNAC libraries

| ID | Structure |
|---|---|
| L228 | (5-bromo-2,3-dimethoxybenzaldehyde) |
| L231 | (benzo[d][1,3]dioxole-4-carbaldehyde) |
| L236 | (5-methylthiophene-2-carbaldehyde) |
| L237 | (4-iodobenzaldehyde) |
| L238 | (5-(hydroxymethyl)furan-2-carbaldehyde) |
| L239 | (5-fluoro-2-methoxybenzaldehyde) |
| L240 | (2-(difluoromethoxy)benzaldehyde) |
| L257 | (4-(bis(2-hydroxyethyl)amino)benzaldehyde) |
| L259 | (3-bromo-4,5-dimethoxybenzaldehyde) |
| L260 | (3-bromo-4-methoxybenzaldehyde) |

TABLE 2-continued

Aldehyde building blocks for BDN, BDNCA, BDNAC libraries

| ID | Structure |
|---|---|
| L261 | (2-bromo-3-hydroxy-4-methoxybenzaldehyde) |
| L262 | (5-bromobenzo[d][1,3]dioxole-4-carbaldehyde) |
| L263 | (4-butylbenzaldehyde) |
| L267 | (2-bromo-4-methylbenzaldehyde) |
| L268 | (4-(2-bromoethoxy)-3-methoxybenzaldehyde) |
| L241 | (3,5-dibromo-2-methoxybenzaldehyde) |
| L242 | (3-iodo-4,5-dimethoxybenzaldehyde) |
| L243 | (2,6-dimethylbenzaldehyde) |
| L245 | (2-fluoro-5-methoxybenzaldehyde) |
| L246 | (6-chloro-2-fluoro-3-methylbenzaldehyde) |
| L249 | (3-fluoro-4-methylbenzaldehyde) |

TABLE 2-continued
Aldehyde building blocks for BDN, BDNCA, BDNAC libraries
| ID | Structure |
|---|---|
| L250 | 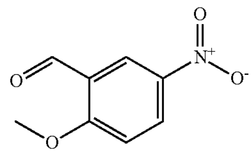 |
| L251 | 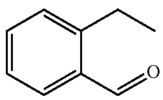 |
| L252 | 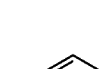 |
| L274 | 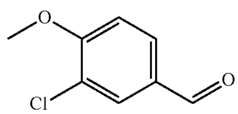 |
| L275 | 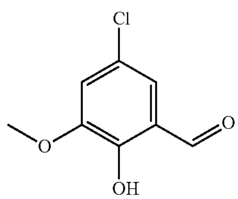 |
| L277 | 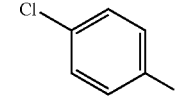 |
| L281 | 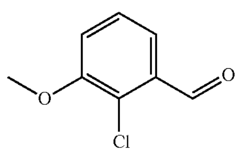 |
| L282 | 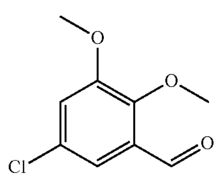 |
| L283 | 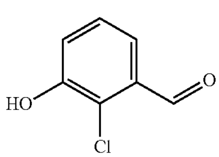 |
| L284 | 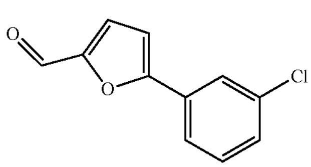 [SMILES: O=Cc1ccc(-c2cccc(Cl)c2)o1] |
| L285 | 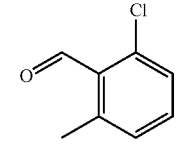 |
| L289 | 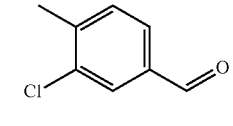 |
| L254 | 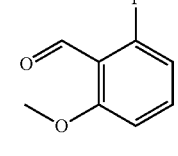 |
| L255 | 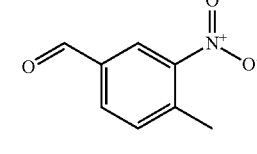 |
| L256 | 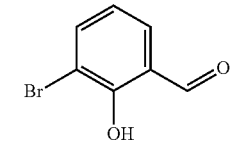 |
| L298 | 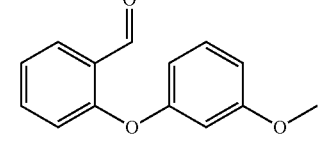 |
| L299 | 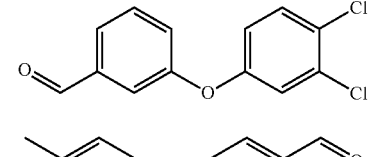 |
| L300 | 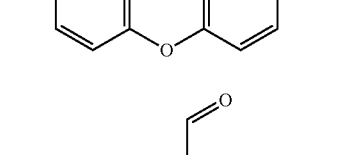 |
| L301 | 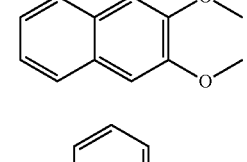 |
| L303 | 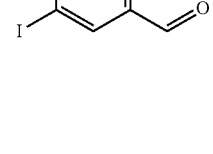 |

TABLE 2-continued

Aldehyde building blocks for BDN, BDNCA, BDNAC libraries

| ID | Structure |
|---|---|
| L304 | 4,4'-oxybis(benzaldehyde) |
| L290 | 4-(3-chlorophenoxy)benzaldehyde |
| L292 | 3-chloro-2-hydroxybenzaldehyde |
| L294 | 3-chloro-4,5-dimethoxybenzaldehyde |
| L325 | 3,5-di-tert-butyl-2-methoxybenzaldehyde |
| L326 | 4-(difluoromethoxy)benzaldehyde |
| L331 | 3,5-bis(benzyloxy)benzaldehyde |
| L332 | 2,2-difluorobenzo[d][1,3]dioxole-5-carbaldehyde |
| L333 | 2-(methylthio)benzaldehyde |
| L335 | 4-methoxy-3-methylbenzaldehyde |
| L305 | 2-fluoro-4,5-dimethoxybenzaldehyde |
| L307 | 3-hydroxy-4,5-dimethoxybenzaldehyde |
| L308 | 3-(3,5-dichlorophenoxy)benzaldehyde |
| L310 | 4-methoxy-2,3-dimethylbenzaldehyde |
| L311 | 4-fluoro-3-phenoxybenzaldehyde |
| L314 | 2-fluoro-3-methoxybenzaldehyde |
| L315 | 2-hydroxy-3-nitrobenzaldehyde |
| L316 | 2,4-diethoxybenzaldehyde |
| L317 | 2,3-diethoxybenzaldehyde |
| L336 | 2-ethoxybenzaldehyde |
| L340 | 10-methylanthracene-9-carbaldehyde |

TABLE 2-continued

Aldehyde building blocks for BDN, BDNCA, BDNAC libraries

| ID | Structure |
|---|---|
| L341 | 2-(4-fluorophenoxy)benzaldehyde |
| L343 | 4,5-dimethyl-2-formylbenzene (2,4,5-trimethylbenzaldehyde) |
| L345 | 3-(1,1,2,2-tetrafluoroethoxy)benzaldehyde |
| L346 | 2-hydroxy-5-(trifluoromethoxy)benzaldehyde |
| L347 | 2,3-dimethoxy-4-methylbenzaldehyde... (2,4-dimethoxy-3-methylbenzaldehyde) |
| L349 | 2,3-dimethylbenzaldehyde |
| L350 | 4-methoxy-3-nitrobenzaldehyde |
| L318 | 5-fluoro-2-hydroxybenzaldehyde |
| L319 | 5-phenylfuran-2-carbaldehyde |
| L320 | 2-ethoxy-3-methoxybenzaldehyde |
| L322 | 4-(4-fluorophenoxy)benzaldehyde |
| L323 | 3-ethoxybenzaldehyde |
| L368 | benzofuran-2-carbaldehyde |
| L370 | 2,4-dimethylbenzaldehyde |
| L371 | 5-(4-chlorophenyl)furan-2-carbaldehyde |
| L372 | 2-chloro-3,4-dimethoxybenzaldehyde |
| L353 | 1H-imidazole-2-carbaldehyde |
| L359 | 2-fluoro-4-methoxybenzaldehyde |
| L363 | 4-((trifluoromethyl)thio)benzaldehyde |
| L365 | 2-(trifluoromethoxy)benzaldehyde |
| L366 | 2-hydroxy-4,6-dimethoxybenzaldehyde |
| L417 | (E)-3-(furan-2-yl)acrylaldehyde |

TABLE 2-continued

Aldehyde building blocks for BDN, BDNCA, BDNAC libraries

| ID | Structure |
|---|---|
| L421 | 3-phenylpropynal |
| L423 | thiophene-2-carbaldehyde |
| L425 | 2'-fluoro-[1,1'-biphenyl]-4-carbaldehyde |
| L375 | 1H-indole-3-carbaldehyde |
| L376 | 2-ethyl-4-ethylhepta-2,6-dienal |
| L377 | 4-(dimethylamino)-1-naphthaldehyde |
| L378 | 4-((4-fluorobenzyl)oxy)benzaldehyde |
| L384 | 2-iodobenzaldehyde |
| L392 | 3,5-dichlorobenzaldehyde |
| L393 | 5-(2-chlorophenyl)furan-2-carbaldehyde |
| L396 | 2,3-dibromo-4-hydroxy-5-methoxybenzaldehyde |
| L397 | 3-ethoxy-4-hydroxybenzaldehyde |
| L427 | 5-(4-nitrophenyl)furan-2-carbaldehyde |
| L428 | 5-(4-bromophenyl)furan-2-carbaldehyde |
| L429 | 4-ethoxybenzaldehyde |
| L430 | 1,3,5-trimethyl-1H-pyrazole-4-carbaldehyde |
| L431 | 3-formylbenzoic acid |
| L433 | quinoline-8-carbaldehyde |

TABLE 2-continued

Aldehyde building blocks for BDN, BDNCA, BDNAC libraries

| ID | Structure |
|---|---|
| L435 | 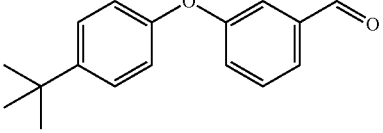 |
| L437 | 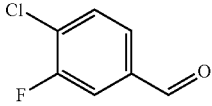 |
| L440 | 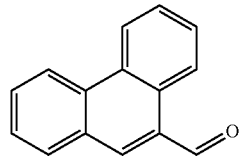 [SMILES: O=Cc1cc2ccccc2c2ccccc12] |
| L401 | 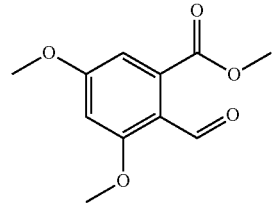 |
| L403 | 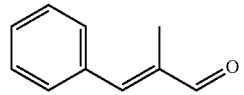 |

TABLE 2-continued

Aldehyde building blocks for BDN, BDNCA, BDNAC libraries

| ID | Structure |
|---|---|
| L404 | 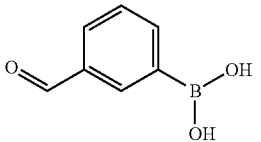 [SMILES: O=Cc1cccc(B(O)O)c1] |
| L405 | 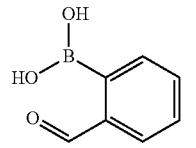 [SMILES: O=Cc1ccccc1B(O)O] |
| L407 | 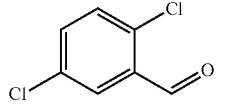 |
| L409 | 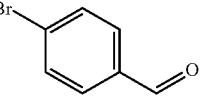 |
| L414 | 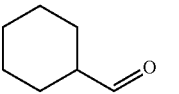 |
| L458 | 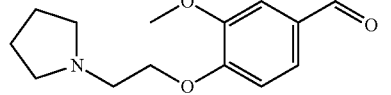 |

TABLE 3

Optical properties of BDNCA library, BDN series does not have fluorescent emission, BDNAC library has same properties as BDNCA.

| BDNCA Code | | | | | Qunt. | | |
|---|---|---|---|---|---|---|---|
| Plate | Code | Well | Abs | Flu | Yield | ε | Flu-Abs |
| BDNCA-1 | BDNCA-1 | BDNCA1-A2 | 564 | 602 | 0.14 | 91,442 | 38 |
| | BDNCA-2 | BDNCA1-A3 | 613 | weak | weak | 27,735 | |
| | BDNCA-3 | BDNCA1-A4 | 605 | weak | weak | 73,593 | |
| | BDNCA-4 | BDNCA1-A5 | 570 | 611 | 0.18 | 79,908 | 41 |
| | BDNCA-5 | BDNCA1-A6 | 566 | 589 | 0.09 | 39,542 | 23 |
| | BDNCA-6 | BDNCA1-A7 | 536 | weak | weak | 41,465 | |
| | BDNCA-7 | BDNCA1-A8 | 570 | 616 | 0.19 | 87,872 | 46 |
| | BDNCA-8 | BDNCA1-A9 | 562 | 582 | 0.04 | 29,108 | 20 |
| | BDNCA-9 | BDNCA1-A10 | 556 | 575 | 0.10 | 47,780 | 19 |
| | BDNCA-12 | BDNCA1-A11 | 557 | 576 | 0.10 | 49,428 | 19 |
| | BDNCA-14 | BDNCA1-B2 | 599 | | | 35,149 | |
| | BDNCA-16 | BDNCA1-B3 | 562 | 585 | 0.13 | 55,469 | 23 |
| | BDNCA-17 | BDNCA1-B4 | 627 | weak | weak | 52,998 | |

TABLE 3-continued

Optical properties of BDNCA library, BDN series does not have fluorescent emission, BDNAC library has same properties as BDNCA.

| BDNCA Code | | | | | Qunt. | | |
|---|---|---|---|---|---|---|---|
| Plate | Code | Well | Abs | Flu | Yield | ε | Flu-Abs |
| | BDNCA-18 | BDNCA1-B5 | 569 | 611 | 0.08 | 31,304 | 42 |
| | BDNCA-19 | BDNCA1-B6 | 558 | 580 | 0.13 | 61,236 | 22 |
| | BDNCA-22 | BDNCA1-B7 | 568 | 591 | 0.02 | 21,968 | 23 |
| | BDNCA-25 | BDNCA1-B8 | 566 | 594 | 0.09 | 32,952 | 28 |
| | BDNCA-30 | BDNCA1-B9 | 602 | weak | weak | 15,652 | |
| | BDNCA-32 | BDNCA1-B10 | 583 | 649 | 0.06 | 27,735 | 66 |
| | BDNCA-34 | BDNCA1-B11 | 551 | 597 | 0.14 | 42,288 | 46 |
| | BDNCA-36 | BDNCA1-C2 | 572 | 610 | 0.08 | 30,755 | 38 |
| | BDNCA-38 | BDNCA1-C3 | 568 | weak | weak | 23,890 | |
| | BDNCA-40 | BDNCA1-C4 | 556 | 579 | 0.12 | 61,785 | 23 |
| | BDNCA-42 | BDNCA1-C5 | 556 | 577 | 0.08 | 54,645 | 21 |
| | BDNCA-43 | BDNCA1-C6 | 566 | 596 | 0.03 | 25,812 | 30 |
| | BDNCA-44 | BDNCA1-C7 | 580 | weak | weak | 12,632 | |
| | BDNCA-45 | BDNCA1-C8 | 566 | 598 | 0.13 | 82,929 | 32 |
| | BDNCA-46 | BDNCA1-C9 | 566 | 598 | 0.10 | 42,563 | 32 |
| | BDNCA-48 | BDNCA1-C10 | 566 | 597 | 0.07 | 44,211 | 31 |
| | BDNCA-49 | BDNCA1-C11 | 564 | 581 | 0.03 | 20,046 | 17 |
| | BDNCA-51 | BDNCA1-D2 | 561 | 582 | 0.05 | 21,419 | 21 |
| | BDNCA-53 | BDNCA1-D3 | 570 | 621 | 0.06 | 31,579 | 51 |
| | BDNCA-54 | BDNCA1-D4 | 562 | 581 | 0.07 | 38,169 | 19 |
| | BDNCA-61 | BDNCA1-D5 | 581 | 627 | 0.08 | 33,776 | 46 |
| | BDNCA-62 | BDNCA1-D6 | 570 | 618 | 0.08 | 38,169 | 48 |
| | BDNCA-63 | BDNCA1-D7 | 572 | 623 | 0.07 | 35,149 | 51 |
| | BDNCA-65 | BDNCA1-D8 | 593 | 630 | 0.04 | 30,755 | 37 |
| | BDNCA-67 | BDNCA1-D9 | 542 | 582 | 0.12 | 36,522 | 40 |
| | BDNCA-68 | BDNCA1-D10 | 553 | 573 | 0.05 | 27,735 | 20 |
| | BDNCA-69 | BDNCA1-D11 | 577 | 610 | 0.09 | 40,641 | 33 |
| | BDNCA-70 | BDNCA1-E2 | 587 | 677 | 0.04 | 29,931 | 90 |
| | BDNCA-72 | BDNCA1-E3 | 573 | 618 | 0.02 | 17,849 | 45 |
| | BDNCA-73 | BDNCA1-E4 | 564 | 585 | 0.04 | 27,185 | 21 |
| | BDNCA-75 | BDNCA1-E5 | 562 | 600 | 0.09 | 35,973 | 38 |
| | BDNCA-76 | BDNCA1-E6 | 574 | 602 | 0.07 | 27,460 | 28 |
| | BDNCA-77 | BDNCA1-E7 | 559 | 581 | 0.09 | 45,034 | 22 |
| | BDNCA-78 | BDNCA1-E8 | 596 | weak | weak | 37,071 | |
| | BDNCA-82 | BDNCA1-E9 | 582 | 632 | 0.04 | 18,398 | 50 |
| | BDNCA-83 | BDNCA1-E10 | 557 | 577 | 0.12 | 40,366 | 20 |

TABLE 3-continued

Optical properties of BDNCA library, BDN series does not have fluorescent emission, BDNAC library has same properties as BDNCA.

| Plate | BDNCA Code | Well | Abs | Flu | Qunt. Yield | ε | Flu-Abs |
|---|---|---|---|---|---|---|---|
| | BDNCA-88 | BDNCA1-E11 | 566 | 584 | 0.11 | 27,185 | 18 |
| | BDNCA-89 | BDNCA1-F2 | 580 | 634 | 0.08 | 33,501 | 54 |
| | BDNCA-90 | BDNCA1-F3 | 563 | 593 | 0.04 | 20,046 | 30 |
| | BDNCA-91 | BDNCA1-F4 | 559 | weak | weak | 34,050 | |
| | BDNCA-92 | BDNCA1-F5 | 555 | 579 | 0.01 | 15,652 | 24 |
| | BDNCA-93 | BDNCA1-F6 | 594 | weak | weak | 16,476 | |
| | BDNCA-94 | BDNCA1-F7 | 548 | 662 | 0.02 | 23,890 | 114 |
| | BDNCA-97 | BDNCA1-F8 | 563 | 575 | 0.01 | 24,989 | 12 |
| | BDNCA-103 | BDNCA1-F9 | 598 | 680 | 0.04 | 28,558 | 82 |
| | BDNCA-107 | BDNCA1-F10 | 624 | weak | weak | 56,018 | |
| | BDNCA-108 | BDNCA1-F11 | 549 | 582 | 0.10 | 39,542 | 33 |
| | BDNCA-110 | BDNCA1-G2 | 566 | 596 | 0.16 | 56,568 | 30 |
| | BDNCA-111 | BDNCA1-G3 | 570 | 599 | 0.04 | 18,947 | 29 |
| | BDNCA-128 | BDNCA1-G4 | 559 | 584 | 0.02 | 14,554 | 25 |
| | BDNCA-131 | BDNCA1-G5 | 643 | weak | weak | 18,124 | |
| | BDNCA-132 | BDNCA1-G6 | 569 | 599 | 0.02 | 36,796 | 30 |
| | BDNCA-134 | BDNCA1-G7 | 566 | weak | weak | 12,082 | |
| | BDNCA-135 | BDNCA1-G8 | 577 | 618 | 0.07 | 37,346 | 41 |
| | BDNCA-137 | BDNCA1-G9 | 564 | 584 | 0.10 | 43,387 | 20 |
| | BDNCA-139 | BDNCA1-G10 | 568 | 607 | 0.09 | 35,423 | 39 |
| | BDNCA-140 | BDNCA1-G11 | 566 | 598 | 0.07 | 27,185 | 32 |
| | BDNCA-143 | BDNCA1-H2 | 555 | 577 | 0.13 | 50,801 | 22 |
| | BDNCA-144 | BDNCA1-H3 | 585 | weak | weak | 62,609 | |
| | BDNCA-147 | BDNCA1-H4 | 557 | 578 | 0.07 | 23,616 | 21 |
| | BDNCA-164 | BDNCA1-H5 | 570 | 615 | 0.07 | 31,030 | 45 |
| | BDNCA-177 | BDNCA1-H6 | 558 | 581 | 0.15 | 73,867 | 23 |
| | BDNCA-178 | BDNCA1-H7 | 563 | 589 | 0.09 | 61,785 | 26 |
| | BDNCA-185 | BDNCA1-H8 | 581 | 646 | 0.06 | 29,931 | 65 |
| | BDNCA-186 | BDNCA1-H9 | 556 | 576 | 0.14 | 61,510 | 20 |
| | BDNCA-190 | BDNCA1-H10 | 564 | 589 | 0.02 | 17,025 | 25 |
| | BDNCA-192 | BDNCA1-H11 | 577 | 630 | 0.03 | 21,693 | 53 |
| BDNCA-II | BDNCA-195 | BDNCA2-A2 | 605 | 681 | 0.01 | 21,968 | |
| | BDNCA-101 | BDNCA2-A3 | 562 | 589 | 0.20 | 89,245 | 27 |
| | BDNCA-100 | BDNCA2-A4 | 574 | 597 | 0.10 | 48,879 | 23 |
| | BDNCA-20 | BDNCA2-A5 | 556 | 576 | 0.11 | 51,625 | 20 |
| | BDNCA-202 | BDNCA2-A6 | 561 | 585 | 0.13 | 57,666 | 24 |

TABLE 3-continued

Optical properties of BDNCA library, BDN series does not have fluorescent emission, BDNAC library has same properties as BDNCA.

| BDNCA Code | | | | | Qunt. | | |
|---|---|---|---|---|---|---|---|
| Plate | Code | Well | Abs | Flu | Yield | ε | Flu-Abs |
| | BDNCA-231 | BDNCA2-A7 | 559 | 578 | 0.04 | 33,227 | 19 |
| | BDNCA-198 | BDNCA2-A8 | 561 | 587 | 0.15 | 76,064 | 26 |
| | BDNCA-96 | BDNCA2-A9 | 622 | weak | weak | 50,801 | |
| | BDNCA-218 | BDNCA2-A10 | 561 | 586 | 0.14 | 61,785 | 25 |
| | BDNCA-15 | BDNCA2-A11 | 560 | 578 | 0.13 | 49,977 | 18 |
| | BDNCA-179 | BDNCA2-B2 | 566 | 589 | 0.14 | 52,998 | 23 |
| | BDNCA-199 | BDNCA2-B3 | 563 | 583 | 0.15 | 59,314 | 20 |
| | BDNCA-180 | BDNCA2-B4 | 568 | 589 | 0.09 | 50,252 | 21 |
| | BDNCA-209 | BDNCA2-B5 | 556 | 576 | 0.12 | 62,334 | 20 |
| | BDNCA-219 | BDNCA2-B6 | 560 | 581 | 0.16 | 73,043 | 21 |
| | BDNCA-220 | BDNCA2-B7 | 559 | 583 | 0.01 | 40,915 | 24 |
| | BDNCA-206 | BDNCA2-B8 | 574 | 618 | 0.13 | 44,485 | 44 |
| | BDNCA-126 | BDNCA2-B9 | 563 | 578 | 0.01 | 37,071 | 15 |
| | BDNCA-95 | BDNCA2-B10 | 574 | 580 | 0.01 | 31,579 | 6 |
| | BDNCA-29 | BDNCA2-B11 | 567 | 597 | 0.01 | 25,812 | 30 |
| | BDNCA-52 | BDNCA2-C2 | 556 | 580 | 0.05 | 36,247 | 24 |
| | BDNCA-237 | BDNCA2-C3 | 560 | 579 | 0.13 | 70,572 | 19 |
| | BDNCA-228 | BDNCA2-C4 | 558 | 577 | 0.13 | 63,707 | 19 |
| | BDNCA-236 | BDNCA2-C5 | 577 | 608 | 0.11 | 72,220 | 31 |
| | BDNCA-121 | BDNCA2-C6 | 564 | 585 | 0.06 | 39,817 | 21 |
| | BDNCA-117 | BDNCA2-C7 | 559 | 580 | 0.05 | 41,739 | 21 |
| | BDNCA-105 | BDNCA2-C8 | 556 | 575 | 0.06 | 38,719 | 19 |
| | BDNCA-208 | BDNCA2-C9 | 558 | 581 | 0.12 | 64,805 | 23 |
| | BDNCA-27 | BDNCA2-C10 | 554 | 577 | 0.11 | 73,318 | 23 |
| | BDNCA-114 | BDNCA2-C11 | 608 | weak | weak | 42,288 | |
| | BDNCA-223 | BDNCA2-D2 | 583 | weak | weak | 59,863 | |
| | BDNCA-11 | BDNCA2-D3 | 555 | 573 | 0.12 | 64,531 | 18 |
| | BDNCA-23 | BDNCA2-D4 | 553 | 573 | 0.09 | 56,842 | 20 |
| | BDNCA-37 | BDNCA2-D5 | 567 | 600 | 0.14 | 71,121 | 33 |
| | BDNCA-191 | BDNCA2-D6 | 556 | 574 | 0.06 | 24,714 | 18 |
| | BDNCA-238 | BDNCA2-D7 | 575 | 608 | 0.05 | 40,366 | 33 |
| | BDNCA-85 | BDNCA2-D8 | 583 | 614 | 0.08 | 49,977 | 31 |
| | BDNCA-13 | BDNCA2-D9 | 579 | weak | weak | 13,455 | |
| | BDNCA-163 | BDNCA2-D10 | 566 | 595 | 0.04 | 24,165 | 29 |
| | BDNCA-182 | BDNCA2-D11 | 557 | 575 | 0.08 | 37,620 | 18 |
| | BDNCA-153 | BDNCA2-E2 | 569 | 606 | 0.05 | 23,341 | 37 |

TABLE 3-continued

Optical properties of BDNCA library, BDN series does not have fluorescent emission, BDNAC library has same properties as BDNCA.

| Plate | BDNCA Code Code | Well | Abs | Flu | Qunt. Yield | ε | Flu-Abs |
|---|---|---|---|---|---|---|---|
| | BDNCA-57 | BDNCA2-E3 | 561 | 577 | 0.02 | 23,066 | 16 |
| | BDNCA-71 | BDNCA2-E4 | 550 | 570 | 0.05 | 43,661 | 20 |
| | BDNCA-239 | BDNCA2-E5 | 561 | 585 | 0.12 | 69,474 | 24 |
| | BDNCA-240 | BDNCA2-E6 | 554 | 573 | 0.08 | 47,506 | 19 |
| | BDNCA-241 | BDNCA2-E7 | 558 | 578 | 0.09 | 48,879 | 20 |
| | BDNCA-242 | BDNCA2-E8 | 561 | 586 | 0.14 | 70,847 | 25 |
| | BDNCA-243 | BDNCA2-E9 | 545 | 575 | 0.11 | 47,506 | 30 |
| | BDNCA-245 | BDNCA2-E10 | 556 | 575 | 0.11 | 70,023 | 19 |
| | BDNCA-246 | BDNCA2-E11 | 554 | 573 | 0.09 | 43,387 | 19 |
| | BDNCA-247 | BDNCA2-F2 | 574 | 611 | 0.18 | 64,256 | 37 |
| | BDNCA-249 | BDNCA2-F3 | 556 | 577 | 0.12 | 71,945 | 21 |
| | BDNCA-250 | BDNCA2-F4 | 559 | 581 | 0.12 | 53,547 | 22 |
| | BDNCA-251 | BDNCA2-F5 | 555 | 578 | 0.11 | 54,096 | 23 |
| | BDNCA-252 | BDNCA2-F6 | 556 | 576 | 0.08 | 57,666 | 20 |
| | BDNCA-254 | BDNCA2-F7 | 559 | 581 | 0.09 | 56,018 | 22 |
| | BDNCA-255 | BDNCA2-F8 | 556 | 575 | 0.10 | 62,059 | 19 |
| | BDNCA-256 | BDNCA2-F9 | 561 | 582 | 0.04 | 52,449 | 21 |
| | BDNCA-257 | BDNCA2-F10 | 623 | weak | weak | 52,174 | |
| | BDNCA-259 | BDNCA2-F11 | 561 | 582 | 0.11 | 49,428 | 21 |
| | BDNCA-260 | BDNCA2-G2 | 564 | 591 | 0.19 | 86,499 | 27 |
| | BDNCA-261 | BDNCA2-G3 | 567 | 596 | 0.01 | 49,703 | 29 |
| | BDNCA-262 | BDNCA2-G4 | 561 | 582 | 0.07 | 68,924 | 21 |
| | BDNCA-263 | BDNCA2-G5 | 559 | 582 | 0.17 | 124,394 | 23 |
| | BDNCA-267 | BDNCA2-G6 | 558 | 579 | 0.09 | 45,034 | 21 |
| | BDNCA-268 | BDNCA2-G7 | 569 | 609 | 0.12 | 54,371 | 40 |
| | BDNCA-274 | BDNCA2-G8 | 563 | 590 | 0.15 | 71,670 | 27 |
| | BDNCA-275 | BDNCA2-G9 | 563 | 585 | 0.01 | 60,686 | 22 |
| | BDNCA-277 | BDNCA2-G10 | 561 | 585 | 0.15 | 65,080 | 24 |
| | BDNCA-281 | BDNCA2-G11 | 556 | 576 | 0.14 | 79,908 | 20 |
| | BDNCA-282 | BDNCA2-H2 | 557 | 577 | 0.12 | 52,723 | 20 |
| | BDNCA-283 | BDNCA2-H3 | 556 | 574 | 0.05 | 27,460 | 18 |
| | BDNCA-284 | BDNCA2-H4 | 595 | 637 | 0.04 | 31,579 | 42 |
| | BDNCA-285 | BDNCA2-H5 | 544 | 571 | 0.12 | 44,211 | 27 |
| | BDNCA-289 | BDNCA2-H6 | 560 | 586 | 0.16 | 60,686 | 26 |
| | BDNCA-290 | BDNCA2-H7 | 557 | 577 | 0.14 | 65,629 | 20 |
| | BDNCA-292 | BDNCA2-H8 | 559 | 574 | 0.01 | 19,771 | 15 |

TABLE 3-continued

Optical properties of BDNCA library, BDN series does not have fluorescent emission, BDNAC library has same properties as BDNCA.

| Plate | BDNCA Code | Well | Abs | Flu | Qunt. Yield | ε | Flu-Abs |
|---|---|---|---|---|---|---|---|
| | BDNCA-294 | BDNCA2-H9 | 560 | 581 | 0.14 | 63,158 | 21 |
| | BDNCA-298 | BDNCA2-H10 | 558 | 581 | 0.14 | 67,277 | 23 |
| | BDNCA-299 | BDNCA2-H11 | 556 | 575 | 0.09 | 49,703 | 19 |
| BDNCA-III | BDNCA-300 | BDNCA3-A2 | 563 | 590 | 0.21 | 102,151 | 27 |
| | BDNCA-301 | BDNCA3-A3 | 567 | 603 | 0.24 | 85,950 | 36 |
| | BDNCA-302 | BDNCA3-A4 | 553 | 576 | 0.15 | 43,112 | 23 |
| | BDNCA-303 | BDNCA3-A5 | 556 | 575 | 0.12 | 70,847 | 19 |
| | BDNCA-304 | BDNCA3-A6 | 561 | 586 | 0.02 | 18,673 | 25 |
| | BDNCA-305 | BDNCA3-A7 | 568 | 606 | 0.22 | 153,227 | 38 |
| | BDNCA-307 | BDNCA3-A8 | 561 | 595 | 0.01 | 22,792 | 34 |
| | BDNCA-308 | BDNCA3-A9 | 555 | 575 | 0.10 | 63,432 | 20 |
| | BDNCA-310 | BDNCA3-A10 | 566 | 613 | 0.11 | 38,444 | 47 |
| | BDNCA-311 | BDNCA3-A11 | 555 | 575 | 0.09 | 57,117 | 20 |
| | BDNCA-314 | BDNCA3-B3 | 554 | 575 | 0.11 | 52,998 | 21 |
| | BDNCA-315 | BDNCA3-B4 | 655 | weak | weak | 15,652 | |
| | BDNCA-316 | BDNCA3-B5 | 575 | 621 | 0.09 | 32,677 | 46 |
| | BDNCA-317 | BDNCA3-B6 | 557 | 579 | 0.08 | 45,858 | 22 |
| | BDNCA-318 | BDNCA3-B7 | 564 | 589 | 0.02 | 18,398 | 25 |
| | BDNCA-319 | BDNCA3-B8 | 598 | 656 | 0.05 | 54,096 | 58 |
| | BDNCA-320 | BDNCA3-B9 | 557 | 581 | 0.10 | 59,588 | 24 |
| | BDNCA-322 | BDNCA3-B10 | 561 | 588 | 0.14 | 67,826 | 27 |
| | BDNCA-323 | BDNCA3-B11 | 556 | 578 | 0.10 | 60,137 | 22 |
| | BDNCA-325 | BDNCA3-C2 | 558 | 581 | 0.13 | 52,723 | 23 |
| | BDNCA-326 | BDNCA3-C3 | 556 | 576 | 0.08 | 40,915 | 20 |
| | BDNCA-331 | BDNCA3-C4 | 557 | 576 | 0.10 | 48,330 | 19 |
| | BDNCA-332 | BDNCA3-C5 | 556 | 575 | 0.05 | 27,735 | 19 |
| | BDNCA-333 | BDNCA3-C6 | 560 | 586 | 0.12 | 63,707 | 26 |
| | BDNCA-335 | BDNCA3-C7 | 569 | 602 | 0.08 | 41,739 | 33 |
| | BDNCA-336 | BDNCA3-C8 | 562 | 585 | 0.12 | 63,982 | 23 |
| | BDNCA-340 | BDNCA3-C9 | 532 | 549 | 0.04 | 36,247 | 17 |
| | BDNCA-341 | BDNCA3-C10 | 558 | 580 | 0.10 | 58,764 | 22 |
| | BDNCA-343 | BDNCA3-C11 | 562 | 588 | 0.06 | 28,284 | 26 |
| | BDNCA-345 | BDNCA3-D2 | 621 | weak | weak | 12,082 | |
| | BDNCA-346 | BDNCA3-D3 | 561 | 584 | 0.02 | 16,476 | 23 |
| | BDNCA-347 | BDNCA3-D4 | 569 | 604 | 0.08 | 34,874 | 35 |
| | BDNCA-349 | BDNCA3-D5 | 556 | 578 | 0.03 | 36,247 | 22 |

TABLE 3-continued

Optical properties of BDNCA library, BDN series does not have fluorescent emission, BDNAC library has same properties as BDNCA.

| BDNCA Code | | | | | Qunt. | | |
|---|---|---|---|---|---|---|---|
| Plate | Code | Well | Abs | Flu | Yield | ε | Flu-Abs |
| | BDNCA-350 | BDNCA3-D6 | 560 | 581 | 0.07 | 34,874 | 21 |
| | BDNCA-353 | BDNCA3-D7 | 570 | 614 | 0.01 | 15,652 | 44 |
| | BDNCA-359 | BDNCA3-D8 | 564 | 588 | 0.04 | 26,636 | 24 |
| | BDNCA-363 | BDNCA3-D9 | 558 | 576 | 0.08 | 41,190 | 18 |
| | BDNCA-365 | BDNCA3-D10 | 553 | 569 | 0.07 | 45,584 | 16 |
| | BDNCA-366 | BDNCA3-D11 | 579 | 629 | 0.02 | 38,444 | 50 |
| | BDNCA-368 | BDNCA3-E2 | 578 | 601 | 0.03 | 21,968 | 23 |
| | BDNCA-370 | BDNCA3-E3 | 507 | 585 | 0.08 | 34,050 | 78 |
| | BDNCA-371 | BDNCA3-E4 | 596 | 647 | 0.03 | 29,931 | 51 |
| | BDNCA-372 | BDNCA3-E5 | 565 | 594 | 0.13 | 69,474 | 29 |
| | BDNCA-375 | BDNCA3-E6 | 591 | 654 | 0.02 | 21,968 | 63 |
| | BDNCA-376 | BDNCA3-E7 | 552 | 575 | 0.09 | 84,027 | 23 |
| | BDNCA-377 | BDNCA3-E8 | 590 | weak | weak | 58,215 | |
| | BDNCA-378 | BDNCA3-E9 | 566 | 597 | 0.16 | 92,540 | 31 |
| | BDNCA-384 | BDNCA3-E10 | 555 | 578 | 0.11 | 60,686 | 23 |
| | BDNCA-392 | BDNCA3-E11 | 555 | 573 | 0.09 | 53,822 | 18 |
| | BDNCA-393 | BDNCA3-F2 | 591 | 629 | 0.04 | 26,636 | 38 |
| | BDNCA-396 | BDNCA3-F3 | 507 | 531 | 0.01 | 16,476 | 24 |
| | BDNCA-397 | BDNCA3-F4 | 573 | 613 | 0.01 | 38,444 | 40 |
| | BDNCA-401 | BDNCA3-F5 | 569 | 604 | 0.11 | 39,817 | 35 |
| | BDNCA-403 | BDNCA3-F6 | 564 | 598 | 0.08 | 43,661 | 34 |
| | BDNCA-404 | BDNCA3-F7 | 556 | 574 | 0.03 | 18,124 | 18 |
| | BDNCA-405 | BDNCA3-F8 | 558 | 582 | 0.04 | 19,771 | 24 |
| | BDNCA-407 | BDNCA3-F9 | 555 | 575 | 0.07 | 42,288 | 20 |
| | BDNCA-409 | BDNCA3-F10 | 557 | 577 | 0.14 | 87,597 | 20 |
| | BDNCA-414 | BDNCA3-F11 | 524 | 547 | 0.09 | 49,428 | 23 |
| | BDNCA-417 | BDNCA3-G3 | 519 | weak | weak | 13,730 | |
| | BDNCA-421 | BDNCA3-G4 | 526 | weak | weak | 24,439 | |
| | BDNCA-423 | BDNCA3-G5 | 569 | 594 | 0.10 | 61,510 | 25 |
| | BDNCA-425 | BDNCA3-G6 | 562 | 583 | 0.11 | 46,957 | 21 |
| | BDNCA-427 | BDNCA3-G7 | 602 | 630 | 0.03 | 43,112 | 28 |
| | BDNCA-428 | BDNCA3-G8 | 506 | 657 | 0.02 | 17,025 | 151 |
| | BDNCA-429 | BDNCA3-G9 | 566 | 599 | 0.14 | 64,531 | 33 |
| | BDNCA-430 | BDNCA3-G10 | 567 | 601 | 0.09 | 37,895 | 34 |
| | BDNCA-431 | BDNCA3-G11 | 554 | 573 | 0.04 | 19,497 | 19 |
| | BDNCA-433 | BDNCA3-H2 | 564 | 587 | 0.11 | 43,387 | 23 |

TABLE 3-continued

Optical properties of BDNCA library, BDN series does not have
fluorescent emission, BDNAC library has same properties as BDNCA.

| Plate | BDNCA Code Code | Well | Abs | Flu | Qunt. Yield | ε | Flu-Abs |
|---|---|---|---|---|---|---|---|
| | BDNCA-435 | BDNCA3-H3 | 556 | 576 | 0.13 | 61,510 | 20 |
| | BDNCA-437 | BDNCA3-H4 | 556 | 575 | 0.09 | 47,506 | 19 |
| | BDNCA-440 | BDNCA3-H6 | 565 | 602 | 0.17 | 43,661 | 37 |
| | BDNCA-109 | BDNCA3-H7 | 564 | 587 | 0.04 | 23,341 | 23 |
| | BDNCA-210 | BDNCA3-H8 | 566 | 581 | 0.02 | 32,952 | 15 |
| | BDNCA-41 | BDNCA3-H9 | 565 | 594 | 0.13 | 47,780 | 29 |
| | BDNCA-458 | BDNCA3-H10 | 569 | 608 | 0.06 | 25,538 | 39 |
| | BDNCA-0 | BDNCA3-H11 | 495 | 530 | 0.06 | 40,641 | 35 |

Example 2

Pancreatic Islet Imaging Probe Development

Pancreatic islets imaging is an emerging area in diabetes research, with most published studies describing either in vitro or ex vivo attempts to visualize pancreatic cells using various imaging techniques[1, 2]. Imaging techniques that accurately distinguish viable pancreatic islets enable better understanding of the critical factors involved in diabetic research in both clinical and experimental medicine[3, 4]. To conventionally identify pancreatic islets, it is necessary to perform immunostaining on pancreas sections directly, to induce transgenic mice expressing reporter genes[5] or to introduce bioluminescent genes[6, 7] linked to their promoters. Such methods mostly serve as corroborative optical imaging tools and they are also not applicable for direct islets staining for further advancement of diabetes diagnosis research. Optical imaging techniques using fluorescence have several advantages such as detectability, efficiency and applicability in bioimaging probe development. Hence, using combinatorial chemistry, we have in the past developed optical imaging probes based on the Diversity Oriented Fluorescence Library (DOFL) composed of thousands of intrinsically fluorescent small molecules and successfully applied them to detect specific biomolecules[8] or cells (muscle cell[9] and pluripotent stem cells[10]). In addition, we also discovered the glucagon imaging probe, GY (Glucagon Yellow) which can stain live alpha cells[11].

To discover pancreatic islet selective probes, we expanded the other two types of BODIPY library generated from the original GY (Glucagon Yellow) structure. We started with high throughput cell-based screening using mouse acinar cells composed of exocrine tissue, mouse Alpha TC-1 cells and Beta TC-6 cells composed of endocrine pancreas islets. Those three different types of cells were prepared side by side in 384-well plates and incubated with 1 μM of BODIPY compounds for different incubation times ranging from 1 hr to 48 hours. The fluorescence images were acquired on an automated imaging microscope system ImageXpress Micro™. The fluorescence intensity of the stained cells was analyzed using MetaXpress® image processing software. Based on the calculated intensity and manual confirmation, we selected 3 prospective compounds (BDNCA5, BDNCA16 and BDNCA325) that stained either both alpha cells and beta cells or beta cells only as compared with acinar cells. Surprisingly, only one compound, BDNCA-325 (FIG. 1a) showed selectivity in staining the beta TC-6 cells (FIG. 1b).

Next, we further evaluated the 3 compounds in vitro by adding the compounds on cryo-pancreatic sections. It was performed by washing the pancreas sections with PBS before incubating the stained sections with 1 μM of compound for one day at room temperature. The next day, the sections were washed with PBS buffer to remove nonspecific staining. All the three compounds stained the pancreatic islets specifically and the staining was also confirmed by immunostaining with an insulin antibody. The promising fact that these compounds were able to detect pancreatic islets in vitro, suggested the possibility that they can be applied in vivo.

Based on this, we injected the compounds intravenously into the mouse to determine if the staining pattern was similar to that observed in vitro. Each of the 3 compounds was administrated into the mouse separately for one hour before dissection. The cryo-pancreas sections were washed once in PBS before observation. Unlike the previously examined results, the compounds stained the whole pancreas tissue nonspecifically (Data not shown).

Figure 2:
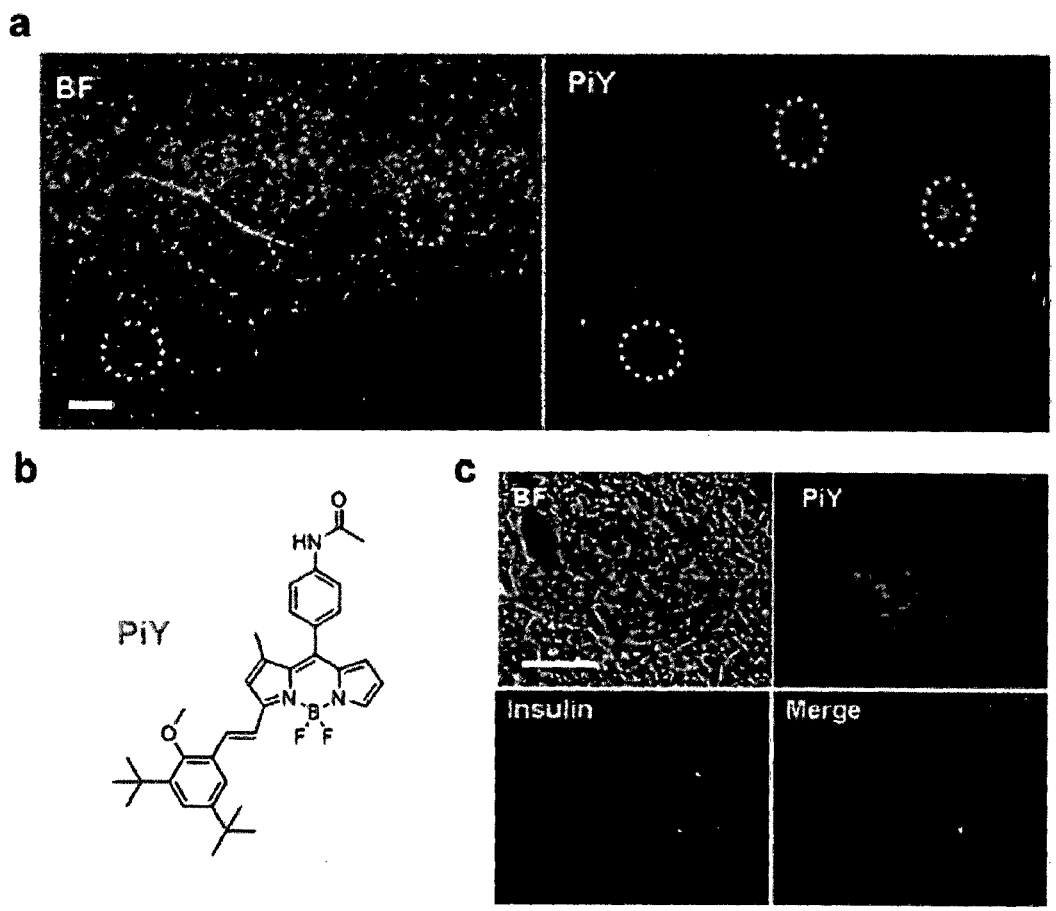
FIGS. 2a-2c show images of visualization of pancreatic islets by PiY in vivo staining.

To develop selective pancreatic islet staining compounds for in vivo conditions, we synthesized several derivatives of the original beta cell selective compound BDNCA325 by changing the reactive groups. The modified compound which was named PiY was synthesized, removing the alpha-chloro part which can bring out nonspecific staining by covalent binding in vivo (FIG. 2a). This PiY compound was tested in vivo to determine if it shows selectivity to pancreatic islets. The optimum time required for the staining of the islets was also investigated in a time dependent manner by injecting the compound at different time points, from 0.5 hr to 4 hrs. It was clearly monitored that the dye slowly starts to invade the exocrine at around two hours to four hours incubation. 0.5 hour to 1 hour incubation was also sufficient to allow visualization of stained islets without any nonspecific staining (FIG. 2a) Moreover, it was possible to observe the islets at low magnification using the fluorescent microscope after one hour incubation with the compound (FIG.

2b). Immunostaining revealed co-localization of BDNAC325 stained islets with both insulin and glucagon antibodies (FIG. 2c).

Eventually these findings resulted in the discovery of the pancreatic islet probe known as "PiY(BDNAC325)", (Pancreatic islet Yellow) ($\lambda$ex/$\lambda$em=558/585 nm) Extinction coefficient=27700; Quantum yield=0.05) which distinguished pancreatic islets from surrounding exocrine tissues in vivo conditions. To compare PiY with other compounds, we investigated the Newport Green™ DCF diacetate[12], a commercially available fluorescent compound for human pancreatic islets, to see if it stains mouse pancreatic islets in vivo. This reference compound had no selectivity for mouse pancreatic islet after injection, although the Newport Green™ DCF diacetate could moderately stain pancreatic islet in vitro. PiY staining as detected in vivo can serve as a platform to improve conventionally available imaging techniques as mentioned previously.

To induce the PiY into mice, it was dissolved in 1% of PEG-4600 and 0.1% of tween-20 from 1 mM of DMSO stock solution. Thus, we considered the effect of both PiY and the solvent on insulin secretion. The stained islets were isolated from pancreas after one hour administration and followed on culture condition. It was noted that both PiY and solvent as described above interfered in neither basal nor secretary insulin regardless of glucose stimulation (FIG. 2d). Therefore PiY can be used as imaging tool for pancreas islets in vivo without hampering the functional effect of insulin secretions involved in diabetic disease.

Figure 3:
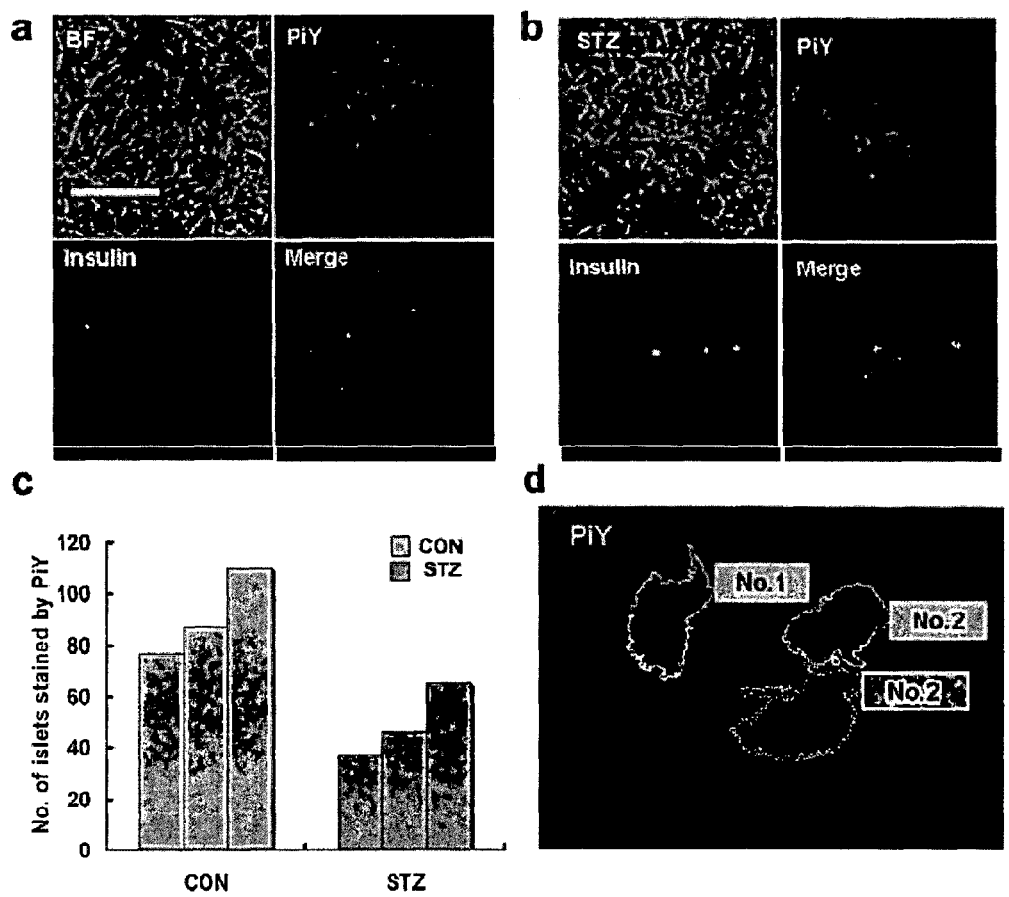
FIGS. 3a-3d show the development of PiY using streptozotocin-induced diabetic mouse model.

For further application, we employed PiY into streptozotocin (STZ) induced type 1 diabetic mouse model to observe healthy pancreatic islets staining vs. diabetic islets. First of all, we pretested to verify whether PiY is able to affect blood glucose level change, not streptozotocin. As expected, there were no detectable changes, for at least a month, for either blood glucose level or body weight at high dosage (up to 150 μM). Using the STZ model of type 1 diabetes, we observed that unhealthy islets from STZ induced mouse had only a few PiY stained islet composed cells (FIG. 3a). To confirm PiY staining, pancreas sections were immunostained with insulin antibody and the obtained images correlated with PiY staining (FIG. 3b). Moreover, we managed to statistically analyze the stained islets by measuring sum intensity and by counting the (islet) number. To start with, we set up 3 groups of STZ and control mice respectively depending on blood glucose level of STZ mouse before PiY injection, to collect the statistical data. The glucose level of STZ mouse of group 1 was over 20 mM. For group 2, it was between 15-18 mM and for group 3, it was around 12-15 mM. The glucose level of control mice were detected more or less 10 mM in all three groups. 50 μM of PiY was administrated into mouse tail vain for 1 hour and the section was prepared as described previously. Staining of islets was observed. We were also able to calculate the intensity in control vs. diabetic model by annotation and measurement program which can detect fluorescence of specified area automatically. The intensity of healthy islets was perceived over two times brighter than diabetic islets in all three groups. In addition, a total number of healthy islets were counted higher than STZ induced diabetic mice. Therefore PiY enables differentiation of healthy islet vs. diabetic islet by staining healthy islets specifically.

Example 3

Microglia Cells Imaging Probe

Microglia cells are immune cells of the brain that are responsible for day-to-day surveillance and maintenance of neural function. They are derived from hematopoietic precursors during early embryogenesis and constitute approximately 5-10% of the neural cell population.[13] Microglia cells are distributed ubiquitously throughout the brain and are characterized by a ramified cellular phenotype in the absence of stimulation.[14] These cells respond dynamically to cellular damage or invading pathogen stimulus by proliferation and migration towards the afflicted regions. This may occur in response to chemokine stimulus or through pattern recognition receptors such as Toll-like receptor 4 (TLR4) which recognize pathogen components such as bacterial LPS.[15] On the recognizing these signals, the microglia secrete potent and potentially cytotoxic cytokines such as interleukin-6 (IL-6) and tumour necrosis factor-$\alpha$ (TNF-$\alpha$). These cytokines play a role in activating a downstream inflammatory cascade, which in a healthy immune system facilitates the clearance of potential pathogens. However, excessive microglia activity has also been associated the pathogenesis of neuroinflammatory diseases.[16] As a result, microglia localization and activity within the brain are of significant interest to those wishing to study their general function and involvement in disease.

The cellular organization of the brain is complex and its tight cellular junctions form the infamous blood-brain-barrier (BBB) thus making drug access possible only for select small molecules. Microglia cells, in particular, are challenging subjects to study due to their relatively low numbers in the brain (5-10%) and slow growth in vitro (3). As a result, primary cultures of microglia are often tedious to prepare to sufficient purity and scale and have a low yield.[17] Current methods of labeling microglia in an in vitro setting are predominantly antibody mediated—with the cell surface markers Iba1, CD11b and CX3CR3 being some of the more common targets. This usually involves the expensive and time-consuming process of acquiring and labeling the cells with the relevant antibodies. More recently, conjugation of the above markers to fluorescent proteins such as EGFP has become popular for live cell imaging purposes. However, the process of generating these transgenic animals is tedious and lengthy thereby making the labeling of these cells by this means a challenging process. Thus the development of new easy-to-use fluorescent probes capable of directly labeling live cells would be an invaluable tool for microglia tracking and in vitro and in vivo imaging purposes. A significant number of microglia-targeted probes have been developed to work in an in vivo setting. Most of these probes are ligands of the 18 kDa translocator protein, also known as the peripheral benzodiazepine receptor (PBR).[18] An example is the popular PET probe, 11C-(R)-PK11195 that is a PBR selective ligand. PBR has been found to be expressed on the outer mitochondrial membrane of activated microglia and the signal derived from the administration of the 11C-(R)-PK 11195 probe is generally interpreted to be indicative of the presence of inflammation and neurodegeneration in the brain.[18] However, the use of such radioligand probes has been plagued with problems such as a low target to background ratio and limited target delivery.[19] There has also been some debate as to what extent PK11195 signal can be attributed to activated microglia. As such, there is still a continued drive for the development of more microglia specific probes to extend the scope of in vitro and in vivo studies.

Chemical biology is an emerging new field that applies the diversity of chemical structures for targeted biological applications.[20] The objective of our study was to identify neural cell type specific fluorescent probes from our Diversity Oriented Fluorescence Library (DOFL) for application in cellular imaging systems. In this case, we identified a fluorescent probe that is specific for primary microglia from a high throughput in vitro culture screening system. Using fluorescence microscopy and flow cytometry analysis, we were able to demonstrate that these probes were selective for primary microglia in primary neural cell cultures and exhibited similar specificity for microglia-derived cell lines. Cytotoxicity and functional assays also showed that these cells remained viable in the presence of staining and retained their ability to express their relevant cytokines and cellular mediators in response to stimulation. Lastly, the efficacy and utility of our small molecule fluorescent probes may also be demonstrated by their use in numerous cellular images applications such as cellular detection and tracking with the potential for further development as in vivo imaging probes.

BDNCA164 (BDNCA1 H5) Exhibit Specificity for Primary Microglia Cells.

Figure 4:
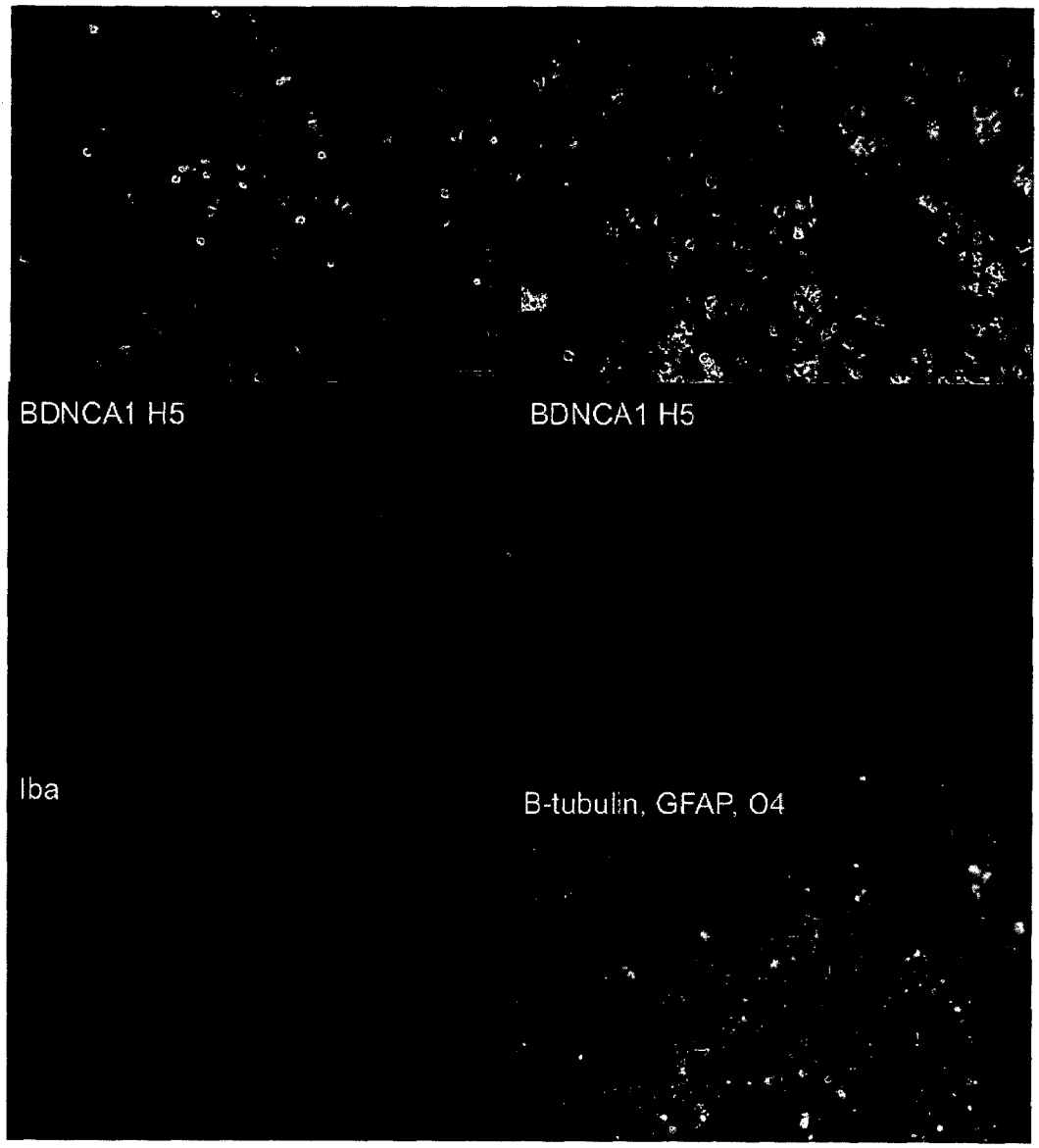
FIG. 4 shows live primary microglia enriched cultures and neuron enriched neural cultures, stained with 500 nM of BDNCA1 H5 and imaged using a Texas red filter. This was followed by fixation and immunostaining for the microglia cell surface marker, Iba (green) and the corresponding neuron (β-tubulin), astrocyte (GFAP) and oligodendrocyte (O4) markers.

Stained cells were subsequently immunostained for Iba1, a known surface marker for microglia to confirm for cell type specificity (FIG. 4). Microglia cells in the brain are also known to constitutively express the chemokine receptor, CX3CR1 that is a cell surface marker. To test for specificity and further rule out that the compounds may be staining other neural cell types, 500 nM of compound was applied to cultures of mixed primary neural cell cultures derived from CX3CR1-GFP transgenic mice and checked for GFP and compound co-localization.

Figure 5:
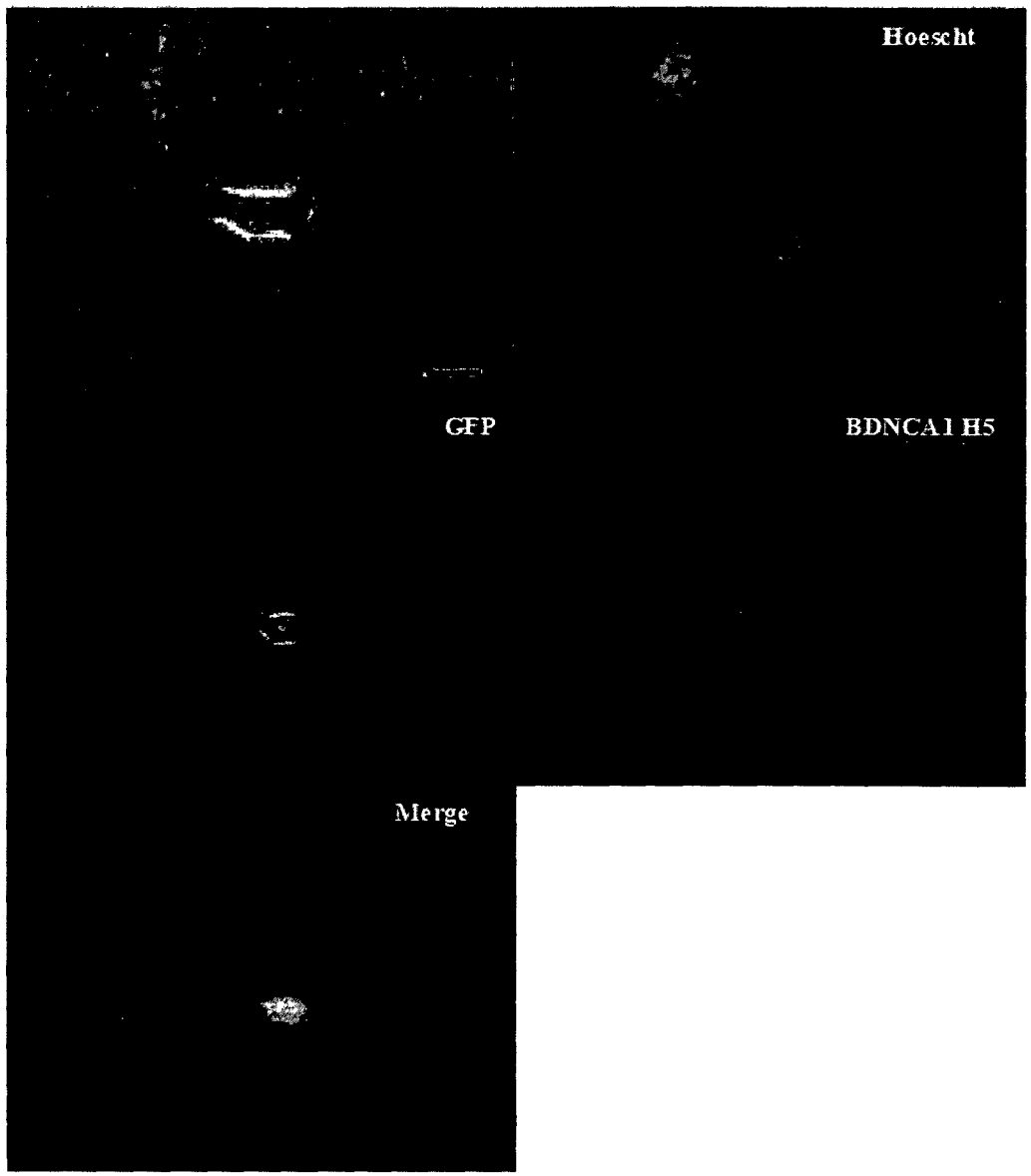
FIG. 5 shows primary microglia from mixed primary neural cell cultures derived from CX3CR1-GFP transgenic mice, stained with 500 nM of BDNCA1 H5 respectively (red). Hoescht staining was used for the labeling of cellular nuclei (Blue).
Figure 6:
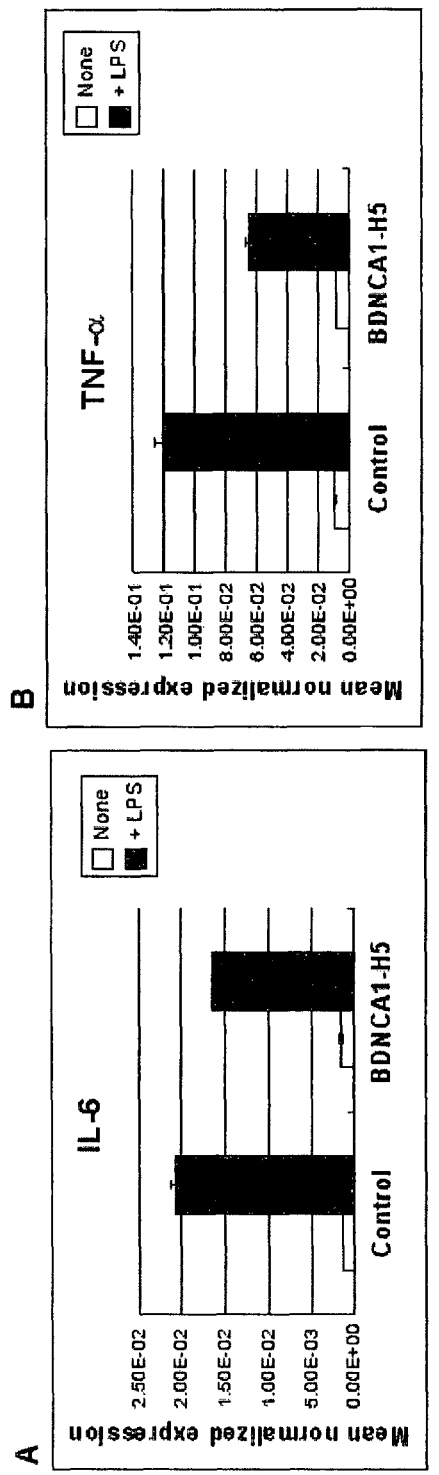
FIGS. 6A and B show cytokine expression of compound-treated BV2 microglia. BV2 cells were pretreated for 1 h with 500 nM of compound before addition of 100 ng/ml of LPS in fresh media. After 6 hours, total RNA was isolated from the cells and cytokine expression levels of IL-6 and TNF-α were measured by RT-PCR.

Our compounds appear to localize within the cytoplasm of the microglia excluding the nucleus, appearing as bright circular dots with a dark centre. To further confirm the specificity of our compounds for microglia in heterogeneous neural cell systems, we used flow cytometry analysis to confirm that our compound signal coincides with GFP positive microglia in mixtures of primary neural cells derived from CX3CR1-GFP transgenic mice (FIG. 5). The signal from GFP-Texas Red double positive microglia cells increased in a dose dependent manner (data not shown) although higher concentrations gave rise to more non-specific staining depending on the incubation duration. To prove that primary microglia were still distinguishable from primary neural cells in the absence of the CX3CR1-GFP marker, neural cells derived from normal FVB/N mice were also stained and analyzed via flow cytometry (FIG. 6).

Compound Specificity is Conserved in the BV2 Microglia Cell Line.

Figure 7:
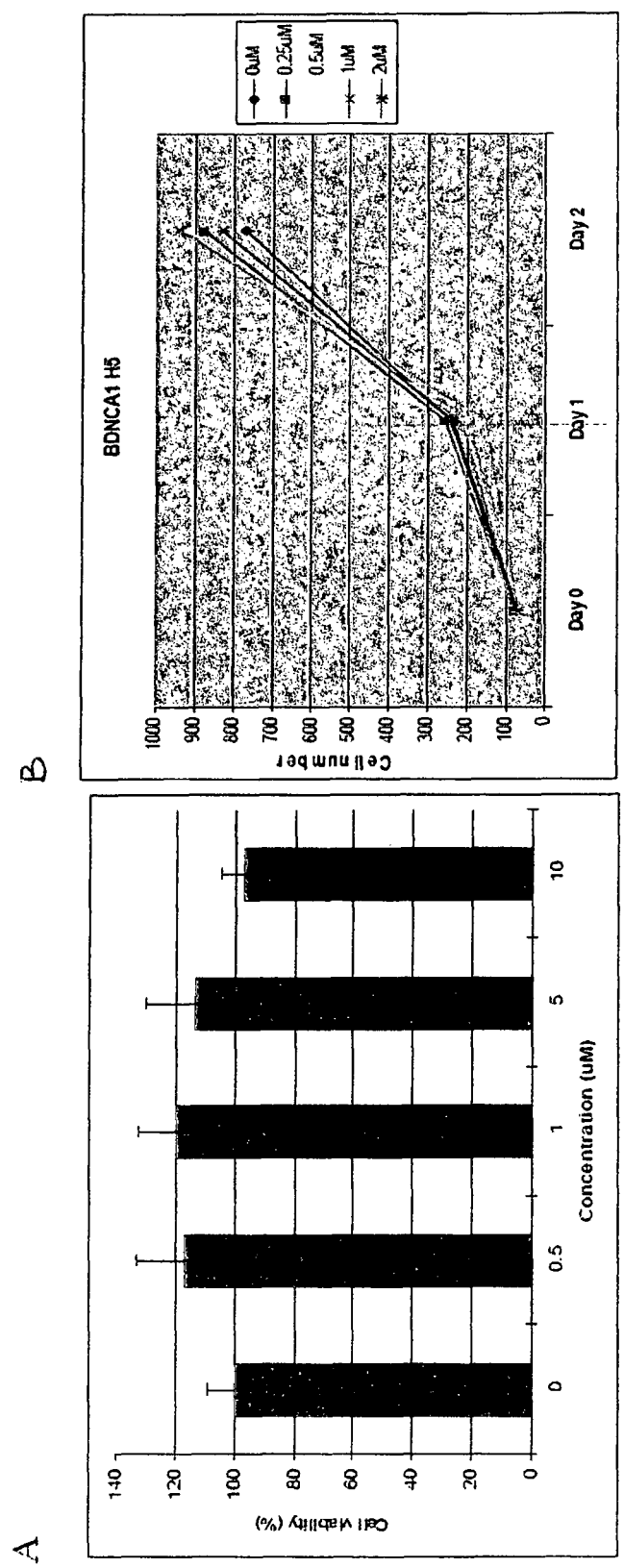
FIGS. 7A and 7B show results of an MTS assay used to assess cell viability after compound staining in cytotoxicity testing.

Our fluorescent compounds were developed using primary neural cells based on the premise that primary cells would reflect the cells in their true native state and represent a reliable benchmark for specificity testing. Cell lines, while highly prolific have been known to spontaneously incur genomic or functional changes that may not reflect their true state.[21] Thus given the specificity of our compounds for primary microglia, we were interested to see if this was also conserved in primary microglia-derived cell lines. To demonstrate this, we used the primary microglia-derived retrovirus transformed cell line, BV-2 in co-culture with mouse embryonic fibroblasts. Compound stained BV-2 cells were clearly distinguishable in co-culture with MEF and showed a similar staining pattern (largely cytoplasmic) with the primary derived microglia thus demonstrating that the specificity of compound towards primary microglia is conserved in primary microglia-derived cell lines. Compound stained microglia retain viability and functional response A central concern in the use of live cell probes is their potential to interfere with normal cellular function, which would be undesirable for downstream applications. Using the MTS assay at a 24 h time point, we can show that both probes are not cytotoxic at their concentrations and durations used (500 nM, 1 hour) and concentrations above this induce only minimal cytotoxicity that are unlikely to affect the cells at our given time points (FIG. 7A). Cell proliferation studies also showed that cells retain their ability to proliferate in vitro in the presence of the compounds with no detrimental effect (FIG. 7B).

The ability of microglia to release nitric oxide in response to stimulation is an important immune defense, which facilitates the removal of potentially harmful pathogens. Here, we show using the Griess assay for nitrate detection that compound stained microglia retain their ability to produce nitric oxide in response to lipopolysaccharide (LPS) and IFN-γ stimulus and that these levels of nitric oxide production are comparable to LPS or IFN-γ stimulation alone. The incubation of microglia with the compounds alone also does not induce significant nitric oxide release as compared to the LPS stimulated controls thus emphasizing the benign effects of the probes on microglia function. This facilitates their use in labeling processes that may require a functional response further downstream.

Cellular Labeling does not Significantly Affect Cytokine Expression.

Figure 8:
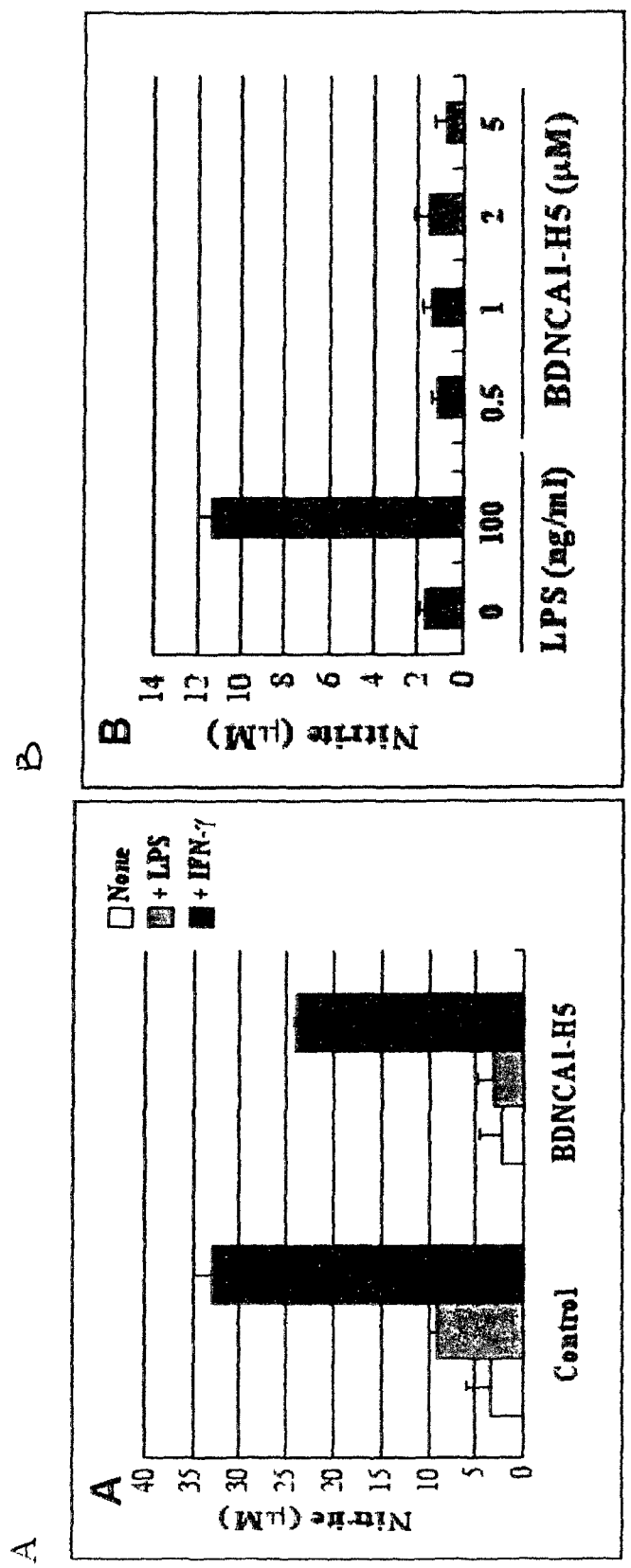
FIG. 8A shows nitric oxide production of compound and LPS/IFN-γ treated microglia. BV2 cells were pretreated for 1 h with 500 nM of compound before addition of 100 ng/nl of LPS or 20 U/ml (20 ng/ml) of IFN-γ in fresh media. Cells were further incubated for 24 h. Nitric oxide production was subsequently measured by the Griess assay and concentrations determined by comparison to a standard curve.
In FIG. 8B, compounds were accessed for potential activating effects on the microglia by measuring nitric oxide production. BV2 cells were pretreated for 1 h with each compound (0.5-5 μM). LPS treated BV2 cells were used as a positive control. After incubation for 24 h, nitric oxide production was measured using the Griess assay and concentrations determined by comparison to a standard curve.
Figure 9:
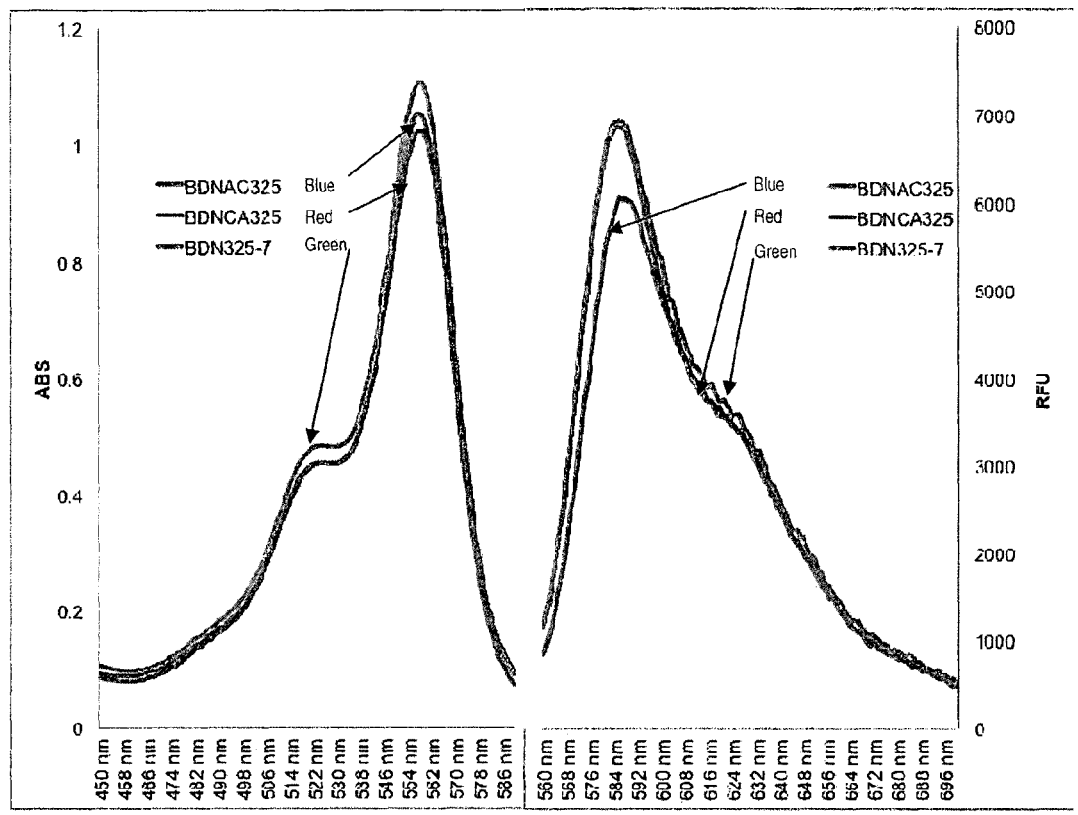
FIG. 9 shows absorption and emission spectra of BDNAC325, BDN 325-7 and BDNCA325, which were measured at the concentration of 200 μM in DMSO.

In addition to nitric oxide release, the cytokine cascade is another important mechanism for counteracting pathogen attack. Bacteria-derived cellular components such as LPS and IFN-γ are known microglia activating agents that induce microglia expression and secretion of pro-inflammatory cytokines such as IL-6 and TNF-α by the activation of Toll-like receptor 4 (TLR4) signaling molecules on the cell surface.[15] Labeling of microglia cells with our fluorescent probes followed by LPS activation and measurement of cytokine expression by real time PCR showed that cytokine expression in response to LPS is not significantly impaired by compound staining (FIG. 8A). Similarly, incubation with the compounds alone did not induce any significant increase in cytokine expression thus indicating that the compounds do not display any activating effects (FIG. 8B).

Compounds were accessed for potential activating effects on the microglia by measuring nitric oxide production. BV2 cells were pretreated for 1 h with each compound (0.5-5 μM). LPS treated BV2 cells were used as a positive control. After incubation for 24 h, nitric oxide production was measured using the Griess assay and concentrations determined by comparison to a standard curve.

Applications for Microglia-Specific Probes.

Cellular Detection and Tracking.

The role of microglia as immunological 'sentinels' in the brain and their ability to mediate the dual functions of neuroprotection and neuroinflammation make them popular candidates as tools for cellular tracking and detection in vitro or in vivo settings. As highlighted by Saura 2007[22], the presence of contaminating microglia in astroglial cultures can skew experimental results significantly. BDNCA 164 can be applied reversibly as a quick and easy method of accessing the amount of microglia contamination in a culture. Alternatively, as shown in fluorescence activated cell sorting (FACS) may be used to remove contaminating populations of microglia or purify them for subsequent reculture.

BDNCA 164 staining does not succumb to methanol washing and is effective in both serum-containing and serum-free conditions thus making ideal for extended duration cellular tracking. To demonstrate this, we stained primary mixed glial cells derived from CX3CR1-GFP mice with BDNCA 164 and imaged them over a time course of 24 hours. The fluorescent signal from our compound makes it possible to trace the movement of primary microglia cells in a culture with no significant phototoxicity or photobleaching. Depending on the experimental design, this compound can thus be used can be used for more complex tracking of microglia in vitro, such as the detection of their chemoattraction towards a given stimulus.

In vivo Studies and Inflammation Detection.

As demonstrated above, our compounds have mainly been optimized to work in vitro conditions. However it can potentially be applied in vivo conditions as well. Its efficacy both in vitro and in vivo facilitates its further development as an in vivo imaging probe for a wide range of applications. This may be carried out through the incorporation of radioactive isotopes such as $^{18}F$, $^{11}C$ into the compound structure thus making it suitable for detection by PET analysis. Neural systems aside, our probes may also possess some affinity for macrophages in the blood, which derive from a similar hematopoietic lineage as brain microglia (data not shown). This may also be another potential area for probe development for inflammation detection and therapeutic delivery in the future.[23]

Example 4

BDNCA1 H5 is Localized Predominantly in the Mitochondria of Microglia Cells

High magnification imaging and co-staining with MitoTracker Green (Invitrogen) shows that a majority of the dye staining is localized in the mitochondria of the cells with some background staining in the cytosol (FIG. 10a). The dye and MitoTracker Green showed good co-staining (Pearson's coefficient=0.93) whereas co-staining with other cell organelle markers (Lysotracker, showed poor co-staining (Pearson's coefficients of 0.47) (FIG. 10b). This strongly suggests that the dye is binding to a target protein present in cell mitochondria.

To further elucidate this, the mitochondrial and cytosolic extracts of BV2 stained cells were isolated and run on SDS-PAGE. Proteins bound by the dye are visible as fluorescent bands under the appropriate excitation and emission wavelengths (FIG. 10c). For BV2 cells, this was visible as a distinct bright band at the 25 kD region that was present in the mitochondrial and not in the cytosol fraction as confirmed by western blotting for COX IV (mitochondrial loading control). This provides further evidence that our target protein is highly expressed in the mitochondria.

Activated Microglia Exhibit Brighter Compound Staining.

We were interested to see if BDNCA 164 (BDNCA1 H5) could also serve as a reporter of cell activation status by discriminating resting and activated microglia by measurement of fluorescence intensity. To investigate this, BV2 cells activated by LPS were stained with BDNCA1 H5 and analyzed in parallel with non-activated cells. Both microscope image and flow cytometry data showed that activated microglia are up to 2 times brighter than their non-activated counterparts (FIG. 11a and 11b).

Material and Methods
Chemical Synthesis

All reactions were performed in oven-dried glassware under a positive pressure of nitrogen. Unless otherwise noted, starting materials and solvents were purchased from Aldrich and Acros organics and used without further purification. Analytical TLC was carried out on Merck 60 F254 silica gel plate (0.25 mm layer thickness) and visualization was done with UV light. Column chromatography was performed on Merck 60 silica gel (230-400 mesh). NMR spectra were recorded on a Bruker Avance 300 NMR spectrometer. Chemical shifts are reported as δ in units of parts per million (ppm) and coupling constants are reported as a δ value in Hertz (Hz). Mass of all the compounds was determined by LC-MS of Agilent Technologies with an electrospray ionization source. Spectroscopic measurements were performed on a fluorometer and UV/VIS instrument, Synergy 4 of bioteck company and Gemini XS fluorescence plate reader. The slit width was 1 nm for both excitation and emission. Relative quantum efficiencies were obtained by comparing the areas under the corrected emission spectrum. The following equation was used to calculate quantum yield $$\Phi x = \Phi st (I_x/I_{st})(A_{st}/A_x)(\eta_x^2/\eta_{st}^2)$$

where Φst is the reported quantum yield of the standard, I is the integrated emission spectrum, A is the absorbance at the excitation wavelength, and ηx is the refractive index of the solvents used. The subscript x denotes unknown and st denotes standard. Rhodamine B was used as standard.

Cell Culture

Primary neural cultures were generated from the whole brains of P1-3 FVB/N mice by trypsinization and trituration methods in accordance with the animal handling regulations of our institution. Briefly, fresh brains were incubated with 0.25% trypsin for 1 hour at 37° C., followed by neutralization with Fetal Bovine Serum (FBS). A single cell suspension was generated by sequential trituration using pipette tips of decreasing diameter. Finally, the cell suspension was filtered using a 40-micron strainer. Cells were grown in DMEM/F12 (Gibco) with 10% FBS and 1% penicillin-streptomycin (Gibco). BV2 and MEF cells were cultured in DMEM/F12+2% FBS and DMEM+20% FBS respectively with 1% penicillin streptomycin.

In vitro PiY Staining and Immunohistochemistry

The pancreas was embedded in optimal cutting temperature compound after 4% PFA fixation for 3 hr and was sectioned into 10 μm thick slices. The sections on slides were air-dried at room temperature for 30 min and stored at −20° C. until use. The sections were washed with cold PBS for 5 min gently. 1 uM of PiY was directly applied on sections for over night at room temperature. Next day, the nonspecific staining was removed using cold PBS three times for 10 min and blocked with 2% bovine serum albumin for 1 hr before incubation with a guinea pig polyclonal antibody against Insulin (diluted 1:1000, DAKO) and rabbit monoclonal antibody for Glucagon (diluted 1:50, Cell Signaling) overnight at 4° C. The antibody was visualized by a Cy5-conjugated goat anti-guinea pig secondary antibody and Cy5-conjugated goat anti-rabbit secondary antibody, respectively (diluted 1:500, Invitrogen).

In vivo Staining of PiY

The 1 mM of DMSO stock was dissolved in PBS with 1% of 4600PEG and 0.1% of tween20 to administrate 50 uM of PiY solution into mouse tail vain for one hour. The pancreas sections were washed with PBS for 5 min after dissection. The sections were observed under fluorescent microscopy on TRITC channel and immunostained with insulin antibody as above.

Streptozotocin Administration for Type 1 Diabetic Mouse Model

The streptozotocin was dissolved in Na-Citrate buffer solution immediately prior to injection and administrated into intraperitoneal using 150 mg/kg as a final dosage. An experimental set was made up of three mice for control and STZ, respectively. The blood glucose level was checked every 3 days using blood glucose meter (Lifescan Inc., Milpitas, Calif., USA). Three STZ mice were separated into each group depending on blood glucose level such as group 1 (>20 mmol/l), group 2 (15-18 mmol/l) and group 3 (12-15 mmol/l) including each control mouse. Subsequently 50 uM of PiY was injected into control and STZ mice tail vain and kept alive for 1 hr.

After that stained islets were observed and carried out the immunostaining using insulin antibody as described.

Insulin Secretion Assay

Islets were isolated after injection of 50 uM of PiY for 1 hr and cultured in basal medium: Krebs-Ringer-Hepes (KRH) medium (containing, mM: 130 NaCl, 4.7 KCl, 1.2 KH2PO4, 1.2 MgSO4, and 2.56 CaCl2, 1 mg ml-1 BSA, 20 mM Hepes, pH 7.4) supplemented with 3 mM glucose for 2 h at 37° C. For static incubation experiments, similar-sized islets from a single mouse (3 islets per tube) were first washed with 3 mM glucose-containing KRH medium, placed in eppendorf tube. Basal medium (100 ul) was added and islets were incubated 15 minutes at 37° C. They were then stimulated with 600 ul of 20 mM glucose-containing KRH medium for 15 min after which the incubation medium was collected after 15 min and replaced with fresh 20 mM glucose KRH. Islets were incubated further 15 min and the medium was collected. Insulin concentration was measured using a Mouse insulin ELISA kit (Mercodia). This experiment was conducted as duplicate with each two mice.

Statistical Islet Analysis by PiY

The three serial sections were prepared on slide numbered Slide No 1. Next sections have over 100 µm size gap to avid the same islets overlapped slide by slide. A total 300 sections per mouse were observed to analyze islets intensity and islets number. By using annotation and measurement software, the intensity of stained islets were automatically detected and calculated at the same time. After automatic analysis, the islets number was counted by manually. The data were normalized by STZ value.

High Throughput Screening

Primary neurons and primary astrocyte enriched cultures were generated using the adherence isolation protocol by Jana et al[32]. Primary microglia enriched cultures were generated by adherence methods and harvested using the mild trypsinization method as described by Saura et al[17]. Neuron, astrocyte and microglia enriched cultures were plated on to 384 well plates and incubated with 500 nM of fluorescent compound for 1-2 hours before screening using the ImageXpress high throughput system. Images were scored using intensity and image-based analysis for the identification of hit compounds.

Immunocytochemistry

Hit compounds from screening were subsequently tested in cultures of mixed primary neural cells (i.e. whole brain cultures) for specificity. Due to the phenotypic heterogeneity observed in neural cells, it is necessary to confirm cell type by immunostaining. As such, 'compound bright' cells in mixed cultures were imaged by fluorescence microscopy using the ECLIPSE Ti microscope (Nikon Instruments Inc) on the NIS Elements 3.10 software. Cells were then fixed in 4% paraformaldehyde (Sigma) and immunostained for Iba (Wako). The same cells were then and re-imaged for Iba.

Fluorescence Imaging

CX3CR1-GFP transgenic mouse pups were a kind gift from Dr. Fluorent Ginhoux. Primary neural cultures from these mice were generated as described above. Cells were stained with 500 nM of compound for 1 hour followed by 1 hour of washing in fresh media before image acquisition. Confocal images were generated on an AIR confocal microscope (Nikon Instruments Inc.) using NIS Elements 3.10 software at 100× magnification.

Flow Cytometry

Primary neural cultures were generated from the brains of CX3CR1-GFP mice as described above. Cells were stained with 500 nM of compound for 1 hour and washed with PBS before acquisition on the BD LSR II analyzer. Cells were acquired using the appropriate filters for GFP and Texas Red wavelengths.

Cytotoxicity Assays

Cytoxicity assays were carried out using the MTS reagent kit (Promega) on 24 h compound treated BV-2 microglia cells in accordance with the manufacturer's instructions. Cell proliferation was measured by counting of Hoescht labeled nuclei (Invitrogen) using the ImageXpress high throughput screening system at Days 0, 1 and 2.

Cytokine Expression

BV2 microglia cells were pretreated for 1 h with 500 nM of compound before addition of 100 ng/ml of LPS in fresh media. After 6 hours, total RNA was isolated from the cells using the RNeasy Mini Kit (QIAGEN Inc.) according to the manufacturer's instructions and cytokine expression levels of IL-6 and TNF-α measured by RT-PCR.

Gene Expression for the Cytokines IL-6. TNFα and GAPDH was measured using the Power SYBR® Green RNA-to-CT™ 1-Step Kit (Applied Biosystem) on a StepOne™ Real-Time PCR System (Applied Biosystems). mRNA levels of the above mentioned genes were normalized to GAPDH expression levels using the Q-gene relative expression software tool.

NCBI References for the Below Sequences:
*Mus musculus* glyceraldehyde-3-phosphate dehydrogenase (GAPDH), mRNA
  Accession: NM_008084.2
*Mus musculus* tumor necrosis factor (Tnf), mRNA
  Accession: NM_013693.2
*Mus musculus* interleukin 6 (116), mRNA
  Accession: NM_031168.1

The following primer sequences (5' to 3') were used in this study:

|  |  |
|---|---|
| | SEQ ID. No.: 1 |
| mGAPDH-F1 | AAGGGCTCATGACCACAGTC |
| | SEQ ID. No.: 2 |
| mGAPDH-R1 | GGATGCAGGGATGATGTTCT |
| | SEQ ID. No.: 3 |
| mTNFα-F1 | TAGCCAGGAGGGAGAACAGA |
| | SEQ ID. No.: 4 |
| mTNFα-R1 | TTTTCTGGAGGGAGATGTGG |
| | SEQ ID. No.: 5 |
| mIL-6-F1 | CCGGAGAGGAGACTTCACAG |
| | SEQ ID. No.: 6 |
| mIL-6-R1 | TCCACGATTTCCCAGAGAAC |

Nitric Oxide Production

BV2 cells were pretreated for 1 hour with 500 nM of compound before addition of 100 ng/nl of LPS or 20 U/ml (20 ng/ml) of IFN-γ in fresh media. After incubation for 24 hours, 50 µl of cell culture media was mixed with an equal volume of Griess reagent (Sigma) in a 96 well plate. Light absorbance was measured at 540 nm. Nitric oxide concentration was determined by comparison with a standard curve generated from a titration of sodium nitrite.

Binding and Washing

To assess mode of binding, BV2 microglia were stained with 500 nM of compound in serum free media for one hour.

Cells were subsequently washed for 1 hour with PBS, fresh serum free media, serum containing media (10%) or methanol. They were then imaged by fluorescence microscopy using the ECLIPSE Ti microscope (Nikon Instruments Inc) on the NIS Elements 3.10 software.

Cell Tracking

Cell tracking was carried out on mixed glial cell cultures stained for 1 h with 500 nM of BDNCA1 H5. This was followed by 1 h of washing in serum containing media. Cell media was replaced once more before video acquisition. For cell tracking, videos were acquired on the Biostation IM (Nikon) at 100× magnification for a duration of 24 hours.

REFERENCES

1. Evgenov, N. V. et al. Nature Medicine 55, 2419-2428 (2006).
2. Malaisse, W. J., Louchami, K. & Sener, A. Nat Rev Endocrinol 5, 394-400 (2009).
3. Hörnblad, A. & Ahlgren, U. Islets. 1, 163-164 (2009).
4. Ahlgren, U. & Gotthardt, M. Adv Exp Med Biol. 654, 39-57 (2010).
5. Speier, S. et al. Nature Medicine 14, 578-573 (2008).
6. Chen, X. & Kaufman, D. B. Methods Mol Biol. 574, 75-85 (2009).
7. Yong, J. et al. Diabetes 60, 1383-92 (2011).
8. Kang, N. Y. et al. Chem Soc Rev. 40, 3613-3626 (2011).
9. Kim, Y. K. et al. J Am Chem Soc. 132, 576-579 (2010).
10. Im, C. N. et al. Angew Chem Int Ed Engl. 49, 7497-7500 (2010).
11. Lee, J. S. et al. J Am Chem Soc. 131, 10077-10082 (2009).
12. Lukowiak, B. et al. J Histochem Cytochem. 49, 519-528 (2001)
13. Fate mapping analysis reveals that adult microglia derive from primitive macrophages. Ginhoux F, Greter M, Leboeuf M, Nandi S, See P, Gokhan S, Mehler M F, Conway S J, Ng L G, Stanley E R, Samokhvalov I M, Merad M. Science. 2010 Nov. 5; 330 (6005):841-5.
14. Microglia phenotype diversity. Olah M, Biber K, Vinet J, Boddeke H W. CNS Neurol Disord Drug Targets. 2011 Feb. 1; 10 (1):108-18.
15. A requirement for microglial TLR4 in leukocyte recruitment into brain in response to lipopolysaccharide. Zhou H, Lapointe B M, Clark S R, Zbytnuik L, Kubes P. J Immunol. 2006 Dec. 1; 177(11):8103-10.
16. The Yin and Yang of Microglia. Czeh M, Gressens P, Kaindl A M. Dev Neurosci. 2011 Jul. 15. [Epub ahead of print]
17. High-yield isolation of murine microglia by mild trypsinization. Saura, Josep, Tusell, Josep Maria, Serratosa, Joan. Glia 44 (3): 183-9, 2003 December
18. PET tracers for the peripheral benzodiazepine receptor and uses thereof. Pernilla J. Schweitzerl, Brian A. Fallon, J. John Mann3, 4, 5, 6 and J. S. Dileep Kumar.
19. Towards molecular imaging of multiple sclerosis. Owen D R, Piccini P, Matthews P M. Mult Scler. 2011 March; 17(3):262-72. Epub 2011 Jan. 6. Review.
20. Diversity-driven chemical probe development for biomolecules: beyond hypothesis-driven approach. Kang N Y, Ha H H, Yun S W, Yu Y H, Chang Y T. Chem Soc Rev. 2011 Jul. 20; 40(7):3613-26.
21. J Neurochem. 2008 October; 107(2):557-69. Epub 2008 Sep. 18 Differential migration, LPS-induced cytokine, chemokine, and NO expression in immortalized BV-2 and HAPI cell lines and primary microglial cultures. Horvath R J, Nutile-McMenemy N, Alkaitis M S, Deleo J A.
22. Microglial cells in astroglial cultures: a cautionary note. Josep Saura. J. Neuroinflammation. 2007; 4: 26
23. Molecular imaging of inflammation/infection: nuclear medicine and optical imaging agents and methods. Signore A, Mather S J, Piaggio G, Malviya G, Dierckx R A. Chem Rev. 2010 May 12; 110(5):3112-45.
24. Chembiochem. 2007 Sep. 24; 8(14):1679-87. Styryl-based compounds as potential in vivo imaging agents for beta-amyloid plaques. Li Q, Min J, Ahn Y H, Namm J, Kim E M, Lui R, Kim H Y, Ji Y, Wu H, Wisniewski T, Chang Y T.
25. Cancer Gene Ther. 2007 August; 14(8):724-37. Epub 2007 Jun. 1. Microglia used as vehicles for both inducible thymidine kinase gene therapy and MRI contrast agents for glioma therapy. Ribot E, Bouzier-Sore A K, Bouchaud V, Miraux S, Delville M H, Franconi J M, Voisin P.
26. Microglia and neuroprotection: from in vitro studies to therapeutic applications. Polazzi E, Monti B. Prog Neurobiol. 2010 November; 92(3):293-315. Epub 2010 Jul. 4. Review.
27. J Neuroimmune Pharmacol (2009) 4:227-243. Imaging Microglial Activation During Neuroinflammation and Alzheimer's Disease. Sriram Venneti & Clayton A. Wiley & Julia Kofler.
28. In vivo MR tracking of therapeutic microglia to a human glioma model. Ribot E J, Miraux S, Konsman J P, Bouchaud V, Pourtau L, Delville M H, Franconi J M, Thiaudière E, Voisin P J.
29. IBC 2011, vol. 3, article no. 3, pp. 1-16. Target Identification: A Challenging Step in Forward Chemical Genetics Raj Kumar Das, Animesh Samanta, Krishnakanta Ghosh, Duanting Zhai, Wang Xu, Dongdong Su, Cheryl Leong, Young-Tae Chang.
30. Glia. 2009 Nov. 1; 57(14): 1469-79. Microglia and neuropathic pain. Inoue K, Tsuda M.
31. Brain research reviews 53 (2): 344-54, 2007 February. The origin and cell lineage of microglia: new concepts. Chan, W Y; Kohsaka, S; Rezaie, P.
32. A simplified method for isolating highly purified neurons, oligodendrocytes, astrocytes, and microglia from the same human fetal brain tissue. Jana, Malabendu; Jana, Arundhati, Pal, Utpal, Pahan, Kalipada. Neurochemical research 32 (12): 2015-22, 2007 Dec.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by structural Formula (I) or pharmaceutically acceptable salts thereof:

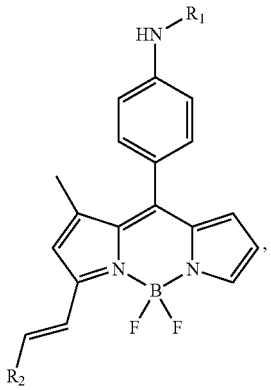

(Formula I)

wherein:

R₁ is hydrogen or -COR₃;

R₂ is (C₆-C₁₆)aryl, (C₃-C₁₀)heteroaryl, (C₁-C₆)alkyl, (C₁-C₆)cycloalkyl, (C₂-C₆)alkenyl, or C≡CH;

R₂ is optionally substituted with 1-5 substituents independently selected from (C₁-C₆)alkyl, halogen, amino, cyano, —COOH, halo(C₁-C₆)alkyl, hydroxy(C₀-C₆) alkyl, (C₆-C₁₀)aryl, (C₃-C₁₀)heteroaryl, halo(C₆-C₁₀) aryl, hydroxy(C₆-C₁₀)aryl, (C₁-C₆)alkoxy, halo(C₁-C₆) alkoxy, (C₆-C₁₆)aryloxy, (C₃-C₈)cycloalkyl, halo(C₆-C₁₀)aryl(C₁-C₆)alkoxy, (C₁-C₆)alkoxy(C₆-C₁₀)aryl (C₁-C₆)alkoxy, nitro, (C₀-C₆)alkyl(C₆-C₁₀)aryl(C₀-C₆) alkoxy, (C₅-C₁₀)heterocycle, —OCHF₂, —OCF₃, —SCF₃, —OBn, cyano(C₁-C₆)alkylene, (C₁-C₆) alkoxyamino, (C₆-C₁₀)aryl(C₂-C₆)alkenyl, (C₂-C₆)alkenyl(C₁-C₆)alkoxy, (C₂-C₆)alkenyl, (C₂-C₆)alkenyl (C₆-C₁₀)aryl, —N((C₀-C₆)alkyl)((C₁-C₆)alkyl), —N((C₁-C₆)alkyleneOH)((C₁-C₆)alkyleneOH), —N((C₀-C₆)alkyl)((C₁-C₆)alkyleneOH), —N((C₁-C₆) alkyleneOCO(C₁-C₆)alkyl)((C₁-C₆)alkyleneOCO(C₁-C₆)alkyl), —NCO(C₁-C₆)alkyl, —NPh₂, —OPh(halogen)₀₋₃, —OPhO(C₁-C₆)alkyl, —OPhO(C₁-C₆)alkyl, —OCO(C₁-C₆)alkyl, —OCO(C₁-C₆)alkoxy, —O(C₁-C₆)alkyl(C₆-C₁₀)aryl, —O(C₂-C₆)alkenyl, —O(C₂-C₆) alkyleneN(CH₃)₂, (C₀-C₆)alkylCOO(C₁-C₆)alkyl, —B(OH)₂ or —S(C₁-C₆)alkyl;

and wherein any of the substituents selected from (C₁-C₆)alkyl, (C₁-C₆)alkoxy, (C₆-C₁₀)aryl, (C₆-C₁₆)aryloxy or (C₅-C₁₀)heteroaryl is further optionally substituted with 1-4 substituents selected from halogen, (C₁-C₆)alkyl, halo(C₁-C₆)alkyl, amino, nitro, cyano, hydroxy(C₀-C₆)alkyl, (C₁-C₆)alkoxy, —COO(C₀-C₆) alkyl, or —CHO; and R₃ is (C₁-C₁₅)alkyl, (C₂-C₁₅)alkenyl, (C₂-C₁₅)alkynyl, (C₆-C₁₀)aryl or (C₅-C₁₀)heteroaryl, wherein R₃ is optionally substituted with 1-4 substituents independently selected from halogen, amino, cyano or hydroxyl.

2. The compound of claim 1, wherein R₂ is (C₆-C₁₀)aryl.

3. The compound of claim 2, wherein R₂ is phenyl, optionally substituted with 1-4 substituents selected from —C(CH₃)₃ and —O—(C₁-C₃)alkyl.

4. The compound of claim 3, wherein the compound is represented by structural Formula (II):

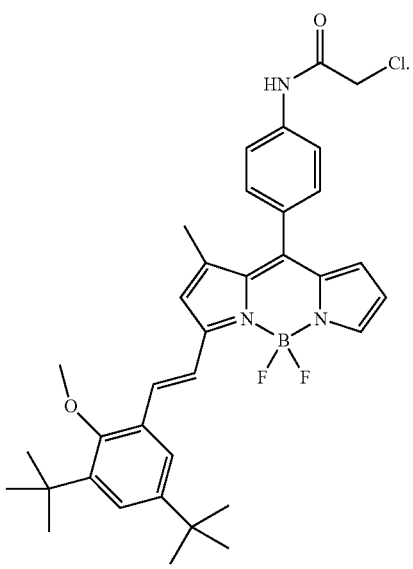

(II)

5. The compound of claim 3, wherein the compound is represented by structural Formula (III):

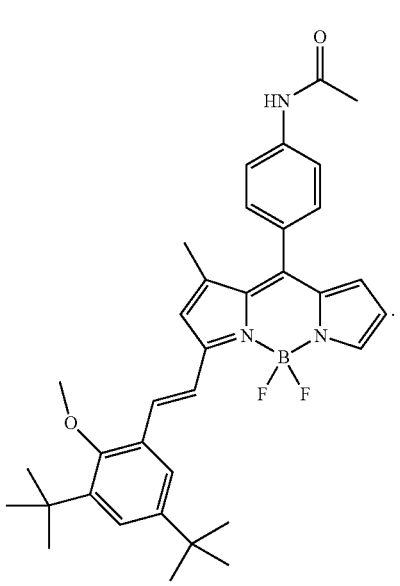

(III)

6. The compound of claim 3, wherein the compound is represented by structural Formula (IV):

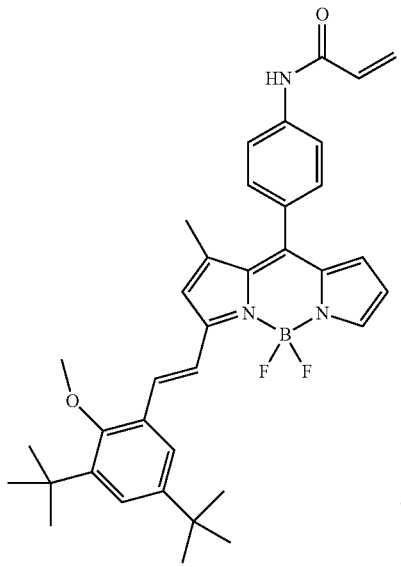

(IV)

7. The compound of claim 3, wherein the compound is represented by structural Formula (V):

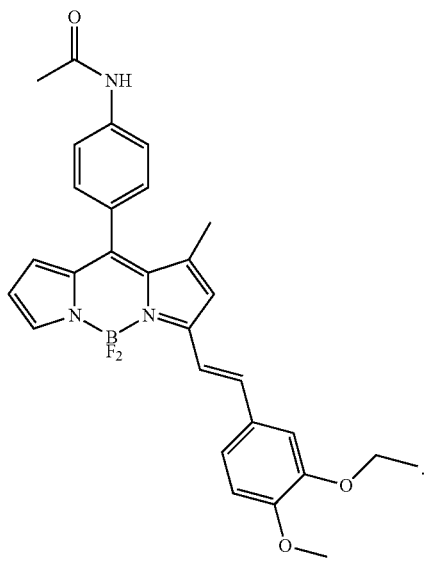

(V)

8. The compound of claim 3, wherein the compound is represented by structural Formula (VI):

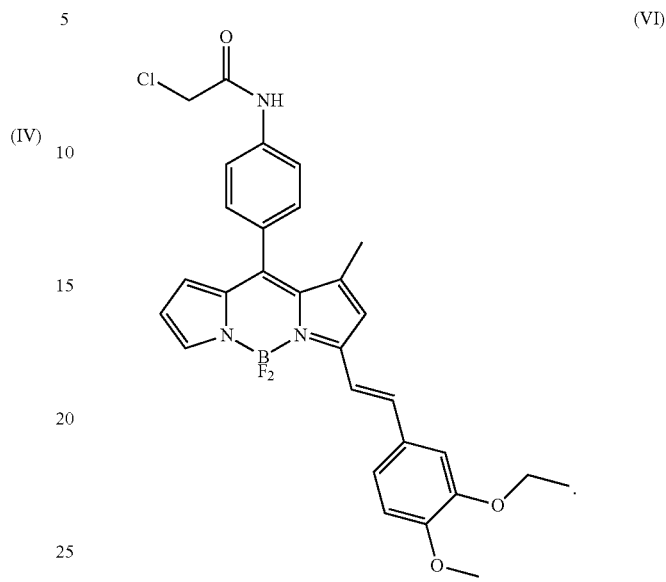

(VI)

9. A pharmaceutical composition comprising one or more pharmaceutically acceptable carriers and/or one or more pharmaceutically acceptable diluents and the compound of claim 1.

10. A method for detecting beta-cells using image based screening, comprising:
   a) contacting a sample comprising cells with a compound of structural Formula (I) or pharmaceutically acceptable salts thereof:

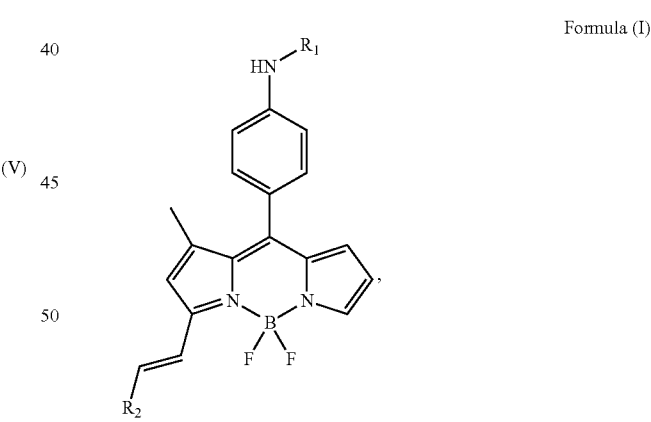

Formula (I)

wherein:
$R_1$ is hydrogen or —$COR_3$;
$R_2$ is ($C_6$-$C_{16}$)aryl, ($C_3$-$C_{10}$)heteroaryl, ($C_1$-$C_6$)alkyl, ($C_1$-$C_6$)cycloalkyl, ($C_2$-$C_6$)alkenyl, or C≡CH;
$R_2$ is optionally substituted with 1-5 substituents independently selected from ($C_1$-$C_6$)alkyl, halogen, amino, cyano, —COOH, halo($C_1$-$C_6$)alkyl, hydroxy($C_0$-$C_6$)alkyl, ($C_6$-$C_{10}$)aryl, ($C_3$-$C_{10}$)heteroaryl, halo($C_6$-$C_{10}$)aryl, hydroxy($C_6$-$C_{10}$)aryl, ($C_1$-$C_6$)alkoxy, halo($C_1$-$C_6$)alkoxy, ($C_6$-$C_{16}$)aryloxy, ($C_3$-$C_8$)cycloalkyl, halo($C_6$-$C_{10}$)aryl($C_1$-$C_6$)alkoxy, ($C_1$-$C_6$)alkoxy($C_6$-$C_{10}$)aryl ($C_1$-$C_6$)alkoxy, nitro, ($C_0$-$C_6$)alkyl($C_6$-$C_{10}$)aryl($C_0$-$C_6$)

alkoxy, $(C_5-C_{10})$heterocycle, $-OCHF_2$, $-OCF_3$, $-SCF_3$, $-OBn$, cyano$(C_1-C_6)$alkylene, $(C_1-C_6)$alkoxyamino, $(C_6-C_{10})$aryl$(C_2-C_6)$alkenyl, $(C_2-C_6)$alkenyl$(C_1-C_6)$alkoxy, $(C_2-C_6)$alkenyl, $(C_2-C_6)$alkenyl$(C_6-C_{10})$aryl, $-N((C_0-C_6)$alkyl$)((C_1-C_6)$alkyl$)$, $-N((C_1-C_6)$alkyleneOH$)((C_1-C_6)$alkyleneOH$)$, $-N((C_0-C_6)$alkyl$)((C_1-C_6)$alkyleneOH$)$, $-N((C_1-C_6)$alkyleneOCO$(C_1-C_6)$alkyl$)((C_1-C_6)$alkyleneOCO$(C_1-C_6)$alkyl$)$, $-NCO(C_1-C_6)$alkyl, $-NPh_2$, $-OPh$(halogen$)_{0-3}$, $-OPhO(C_1-C_6)$alkyl, $-OPhO(C_1-C_6)$alkyl, $-OCO(C_1-C_6)$alkyl, $-OCO(C_1-C_6)$alkoxy, $-O(C_1-C_6)$alkyl$(C_6-C_{10})$aryl, $-O(C_2-C_6)$alkenyl, $-O(C_2-C_6)$alkyleneN$(CH_3)_2$, $(C_0-C_6)$alkylCOO$(C_1-C_6)$alkyl, $-B(OH)_2$ or $-S(C_1-C_6)$alkyl;

and wherein any of the substituents selected from $(C_1-C_6)$alkyl, $(C_1-C_6)$alkoxy, $(C_6-C_{10})$aryl, $(C_6-C_{16})$aryloxy or $(C_5-C_{10})$heteroaryl is further optionally substituted with 1-4 substituents selected from halogen, $(C_1-C_6)$alkyl, halo$(C_1-C_6)$alkyl, amino, nitro, cyano, hydroxy$(C_0-C_6)$alkyl, $(C_1-C_6)$alkoxy, $-COO(C_0-C_6)$alkyl, or $-CHO$; and $R_3$ is $(C_1-C_{15})$alkyl, $(C_2-C_{15})$alkenyl, $(C_2-C_{15})$alkynyl, $(C_6-C_{10})$aryl or $(C_5-C_{10})$heteroaryl, wherein $R_3$ is optionally substituted with 1-4 substituents independently selected from halogen, amino, cyano or hydroxyl;

b) incubating the sample and the compound of step a) together for a period of time sufficient to stain the cells; and c) analyzing the incubated stained cells by spectroscopy to detect a fluorescence signal, wherein the presence of a fluorescence signal is indicative of the presence of the beta cells.

11. A method for detecting microglia cells, comprising:
a) contacting a sample comprising cells with a compound of structural Formula (I) or a pharmaceutically acceptable salt thereof:

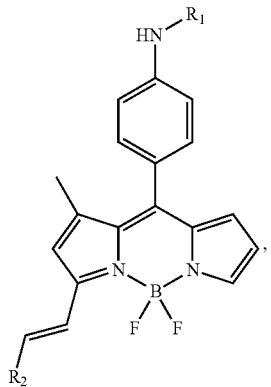

Formula (I)

wherein:
$R_1$ is hydrogen or $-COR_3$;
$R_2$ is $(C_6-C_{16})$aryl, $(C_3-C_{10})$heteroaryl, $(C_1-C_6)$alkyl, $(C_1-C_6)$cycloalkyl, $(C_2-C_6)$alkenyl, or $C\equiv CH$;
$R_2$ is optionally substituted with 1-5 substituents independently selected from $(C_1-C_6)$alkyl, halogen, amino, cyano, $-COOH$, halo$(C_1-C_6)$alkyl, hydroxy$(C_0-C_6)$alkyl, $(C_6-C_{10})$aryl, $(C_3-C_{10})$heteroaryl, halo$(C_6-C_{10})$aryl, hydroxy$(C_6-C_{10})$aryl, $(C_1-C_6)$alkoxy, halo$(C_1-C_6)$alkoxy, $(C_6-C_{16})$aryloxy, $(C_3-C_8)$cycloalkyl, halo$(C_6-C_{10})$aryl$(C_1-C_6)$alkoxy, $(C_1-C_6)$alkoxy$(C_6-C_{10})$aryl$(C_1-C_6)$alkoxy, nitro, $(C_0-C_6)$alkyl$(C_6-C_{10})$aryl$(C_0-C_6)$alkoxy, $(C_5-C_{10})$heterocycle, $-OCHF_2$, $-OCF_3$, $-SCF_3$, $-OBn$, cyano$(C_1-C_6)$alkylene, $(C_1-C_6)$alkoxyamino, $(C_6-C_{10})$aryl$(C_2-C_6)$alkenyl, $(C_2-C_6)$alkenyl$(C_1-C_6)$alkoxy, $(C_2-C_6)$alkenyl, $(C_2-C_6)$alkenyl$(C_6-C_{10})$aryl, $-N((C_0-C_6)$alkyl$)((C_1-C_6)$alkyl$)$, $-N((C_1-C_6)$alkyleneOH$)((C_1-C_6)$alkyleneOH$)$, $-N((C_0-C_6)$alkyl$)((C_1-C_6)$alkyleneOH$)$, $-N((C_1-C_6)$alkyleneOCO$(C_1-C_6)$alkyl$)((C_1-C_6)$alkyleneOCO$(C_1-C_6)$alkyl$)$, $-NCO(C_1-C_6)$alkyl, $-NPh_2$, $-OPh$(halogen$)_{0-3}$, $-OPhO(C_1-C_6)$alkyl, $-OPhO(C_1-C_6)$alkyl, $-OCO(C_1-C_6)$alkyl, $-OCO(C_1-C_6)$alkoxy, $-O(C_1-C_6)$alkyl$(C_6-C_{10})$aryl, $-O(C_2-C_6)$alkenyl, $-O(C_2-C_6)$alkyleneN$(CH_3)_2$, $(C_0-C_6)$alkylCOO$(C_1-C_6)$alkyl, $-B(OH)_2$ or $-S(C_1-C_6)$alkyl;

and wherein any of the substituents selected from $(C_1-C_6)$alkyl, $(C_1-C_6)$alkoxy, $(C_6-C_{10})$aryl, $(C_6-C_{16})$aryloxy or $(C_5-C_{10})$heteroaryl is further optionally substituted with 1-4 substituents selected from halogen, $(C_1-C_6)$alkyl, halo$(C_1-C_6)$alkyl, amino, nitro, cyano, hydroxy$(C_0-C_6)$alkyl, $(C_1-C_6)$alkoxy, $-COO(C_0-C_6)$alkyl, or $-CHO$; and $R_3$ is $(C_1-C_{15})$alkyl, $(C_2-C_{15})$alkenyl, $(C_2-C_{15})$alkynyl, $(C_6-C_{10})$aryl or $(C_5-C_{10})$heteroaryl, wherein $R_3$ is optionally substituted with 1-4 substituents independently selected from halogen, amino, cyano or hydroxyl;

b) incubating the sample and compound of step a) together for a period of time sufficient to stain the cells; and c) analyzing the incubated stained cells by spectroscopy to detect a fluorescence signal, wherein the presence of a fluorescence signal is indicative of the presence of microglia cells.

12. The method of claim 11, wherein the compound of Formula (I) is a compound of Formula (VI):

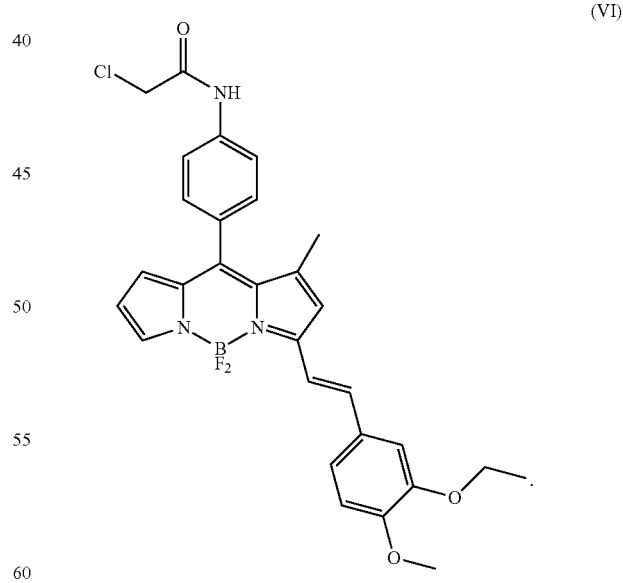

(VI)

13. The method of claim 11, wherein the method further distinguishes activated microglia cells from resting microglia cells by fluorescence intensity.

14. A method for fluorescence imaging of pancreatic islet cells to determine health status of the pancreatic islet cells, comprising:

a) contacting the pancreatic islet cells with a compound of structural Formula (I) or pharmaceutically acceptable salts thereof of claim 1;

b) incubating the cells and compound of step a) together for a period of time sufficient for to stain the cells;

c) analyzing the incubated stained pancreatic islet cells by spectroscopy to detect a fluorescence signal; and d) comparing the signal from step c) to a fluorescence signal from reference sample of healthy pancreatic islet cells, to determine health status of the pancreatic islet cells.

15. The method of claim 14, wherein the compound of Formula (I) has the structure of Formula (III):

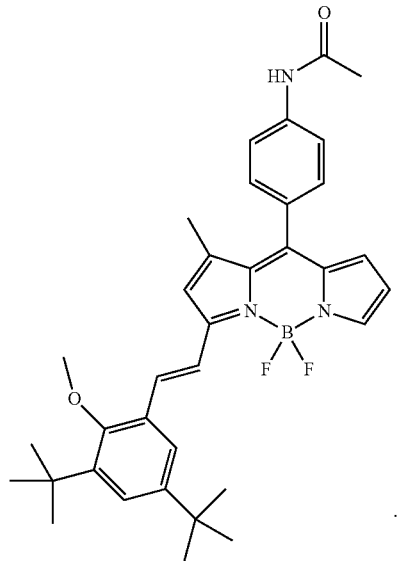

(III)

16. The method of claim 10, wherein the fluorescence signal is measured by fluorometer, UV/VIS spectrometer, Gemini XS fluorescence plate reader, a flow cytometry or a confocal microscope.

17. The method of claim 10, wherein the method is applied in vivo.

18. The method of claim 10, wherein the method is applied in vitro.

19. A method for a solid-phase synthesis of a compound of structural Formula (I) or a pharmaceutically acceptable salt thereof of claim 1, the method comprising:

(a) reacting a compound of structural Formula (VII): wherein the solid support resin is a 2-chlorotrityl polystyrene resin

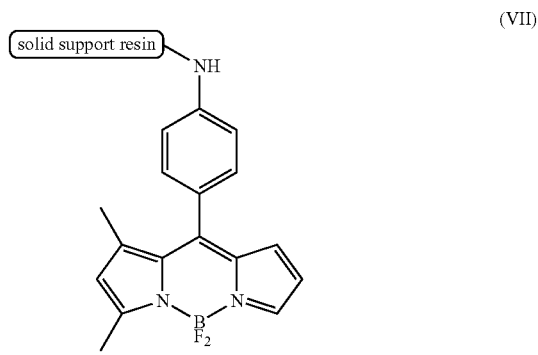

(VII)

with a base and an aldehyde, such that the activated $C_3$-methyl group of Formula (VII) is modified in a solid-phase Knoevenagel-type reaction to produce a compound of Formula VIII:

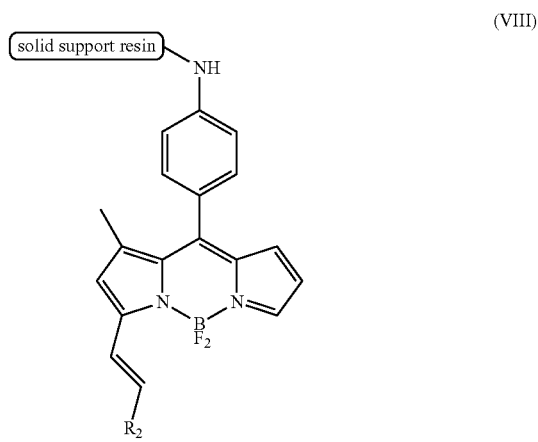

(VIII)

wherein $R_2$ is defined as above;

b) removing the solid support resin from the compound of structural Formula (VIII) produced in step (a) to generate a BODIPY structure of Formula (IX):

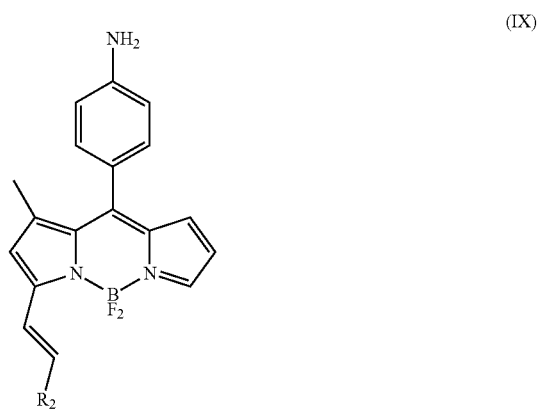

(IX)

wherein $R_2$ is defined as above; and c) optionally reacting the compound of structural Formula (IX) with an acid chloride of the formula $R_1(CO)Cl$ to generate a compound of structural Formula (I), wherein $R_1$ is defined as above.

20. The method of claim 19, wherein the compound is represented by a) structural Formula (II):
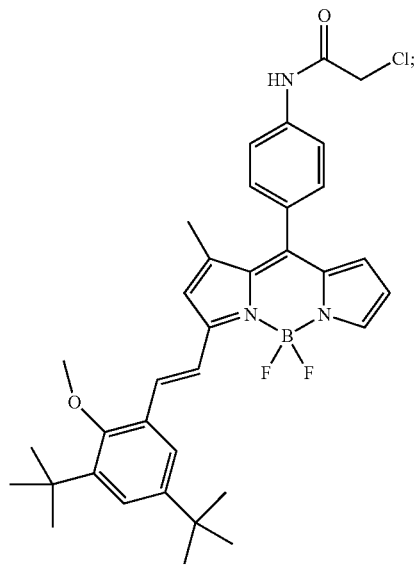
b) structural Formula (III):
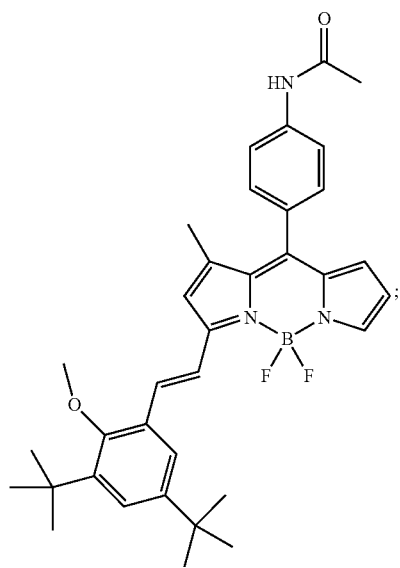
c) structural Formula (IV):
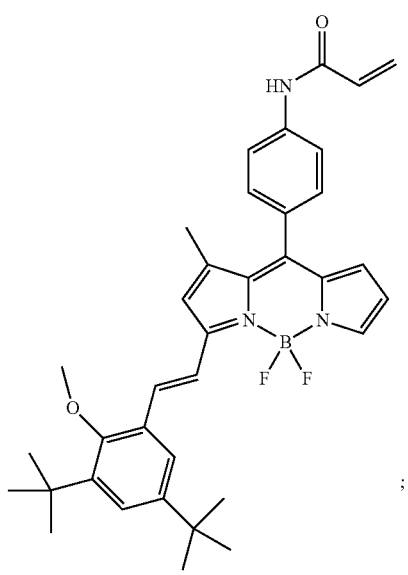
d) structural Formula (V):
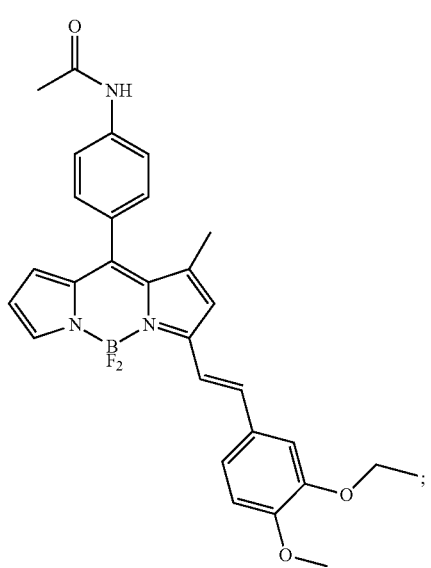

or
e) structural Formula (VI):
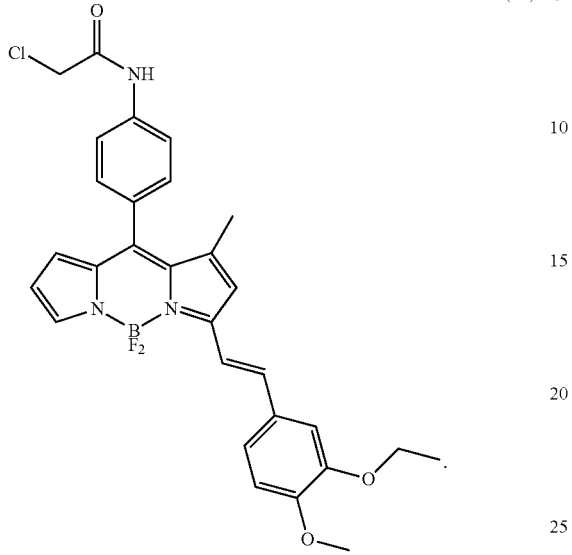
(VI)
* * * * *